(12) United States Patent
Feldmann et al.

(10) Patent No.: US 8,193,409 B2
(45) Date of Patent: Jun. 5, 2012

(54) NUCLEOTIDE SEQUENCES AND POLYPEPTIDES ENCODED THEREBY USEFUL FOR INCREASING PLANT SIZE AND INCREASING THE NUMBER AND SIZE OF LEAVES

(75) Inventors: Kenneth Feldmann, Newbury Park, CA (US); Roger Pennell, Malibu, CA (US); Shing Kwok, Woodland Hills, CA (US); Van-Dinh Dang, Oak Park, CA (US); Hongyu Zhang, Thousand Oaks, CA (US)

(73) Assignee: Ceres, Inc., Thousand Oaks, CA (US)

( * ) Notice: Subject to any disclaimer, the term of this patent is extended or adjusted under 35 U.S.C. 154(b) by 1419 days.

(21) Appl. No.: 10/572,827

(22) PCT Filed: Aug. 18, 2003

(86) PCT No.: PCT/US03/25997
§ 371 (c)(1),
(2), (4) Date: Mar. 7, 2007

(87) PCT Pub. No.: WO2005/019462
PCT Pub. Date: Mar. 3, 2005

(65) Prior Publication Data
US 2007/0250962 A1    Oct. 25, 2007

(51) Int. Cl.
 *C12N 15/82* (2006.01)
 *C12N 5/04* (2006.01)
 *A01H 5/00* (2006.01)
 *A01H 5/10* (2006.01)
(52) U.S. Cl. ......... 800/278; 800/290; 800/298; 435/419
(58) Field of Classification Search ............... None
See application file for complete search history.

(56) References Cited

U.S. PATENT DOCUMENTS

| 6,696,623 | B1 | 2/2004 | Doerner et al. |
| 2001/0049831 | A1* | 12/2001 | Weigel ................. 800/295 |
| 2003/0150026 | A1 | 8/2003 | Chory et al. |

FOREIGN PATENT DOCUMENTS

| EP | 1033405 A2 * | 2/2000 |
| EP | 1 035 405 A2 | 9/2000 |
| WO | WO-98/03631 | 1/1998 |
| WO | WO-01/33945 | 5/2001 |

OTHER PUBLICATIONS

Genoplante (Jul. 2003 NCBI Accession No. CD956065).*
Kano-Murakami et al (1993, FEBS 334:365-368).*
Database Geneseq [Online] Oct. 17, 2000, "*Arabidopsis thaliani* DNA fragment SEQ ID No: 639.", Database accession No. AAC32784.
NCBI database for nucleotide sequences, National Center for Biotechnology Information Nation Library of Medicine, NIH (Bethesda, MD, USA) Whitelaw, C. Accession No. CC631538, Jun. 2003.
Database EMBL [Online] Aug. 20, 2003, "*Arabidopsis thaliani* clone 8161 mRNA.", Database accession No. AY088585.
Database EMBL [Online] Nov. 20, 2002, "ie28f09.g1WGS-ZmayzF (JM107 adapted methyl filtered) Zea mays genomic clone ie28f09 5', DNA sequence." XP002408440, retrieved from EBI accession No. EMPRO:BZ365739, Database accession No. BZ365739.

* cited by examiner

*Primary Examiner* — Stuart F. Baum
(74) *Attorney, Agent, or Firm* — Birch, Stewart, Kolasch & Birch, LLP

(57) ABSTRACT

Isolated polynucleotides and polypeptides encoded thereby are described, together with the use of those products for making transgenic plants that are characterized by increased size, have an increased number and size of rosette leaves and are late-flowering.

9 Claims, 1 Drawing Sheet

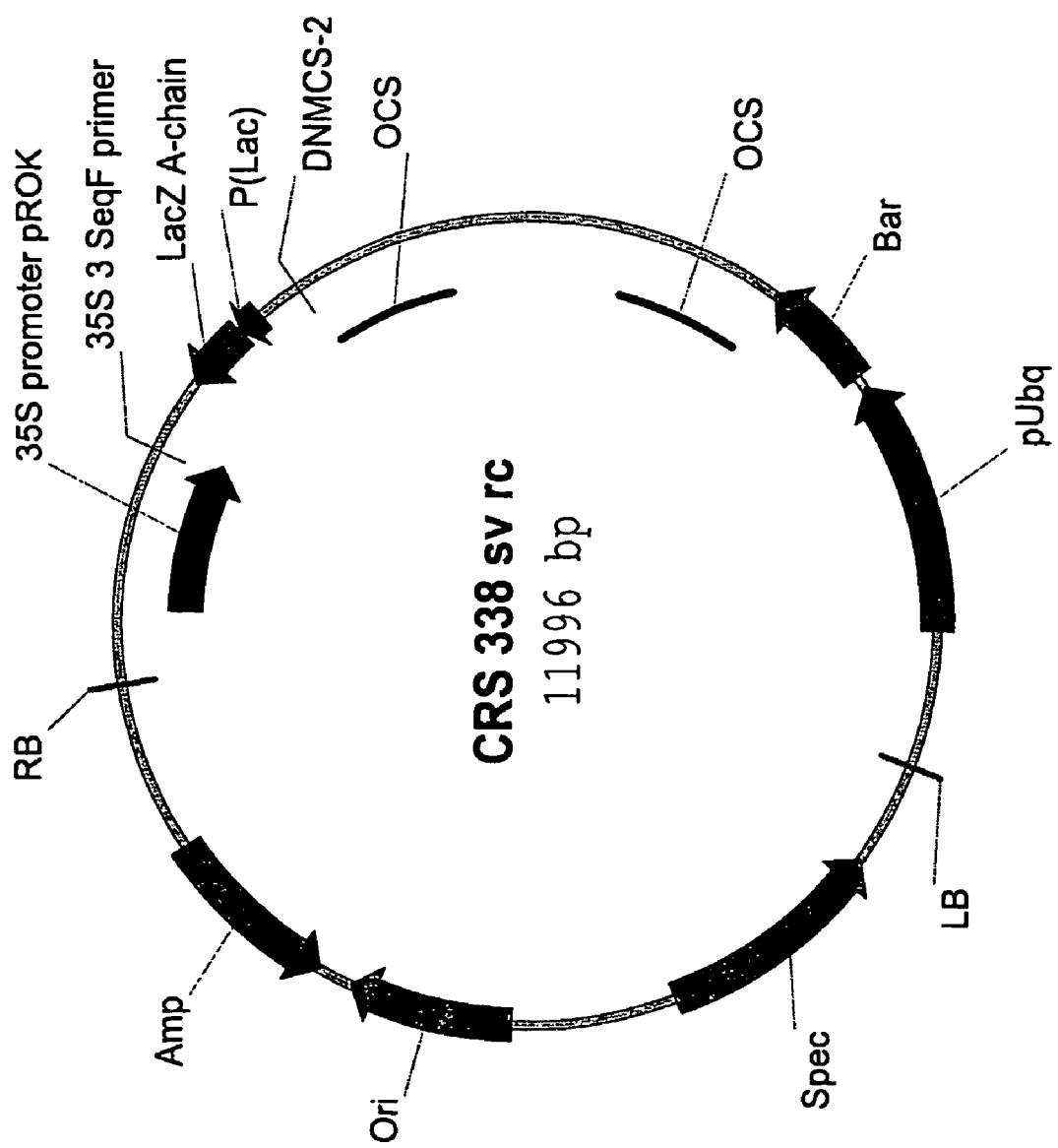

NUCLEOTIDE SEQUENCES AND POLYPEPTIDES ENCODED THEREBY USEFUL FOR INCREASING PLANT SIZE AND INCREASING THE NUMBER AND SIZE OF LEAVES

This application is a national phase under 35 U.S.C §371 of PCT International Application No. PCT/US2003/025997 which has an International filing date of Aug. 18, 2003, which designated the United States of America.

FIELD OF THE INVENTION

The present invention relates to isolated polynucleotides, polypeptides encoded thereby, and the use of those products for making transgenic plants that are characterized by increased size, have an increased number and size of rosette leaves and are late-flowering.

BACKGROUND OF THE INVENTION

There are more than 300,000 species of plants. They show a wide diversity of forms, ranging from delicate liverworts, adapted for life in a damp habitat, to cacti, capable of surviving in the desert. The plant kingdom includes herbaceous plants, such as corn, whose life cycle is measured in months, to the giant redwood tree, which can live for thousands of years. This diversity reflects the adaptations of plants to survive in a wide range of habitats. This is seen most clearly in the flowering plants (phylum Angiospermophyta), which are the most numerous, with over 250,000 species. They are also the most widespread, being found from the tropics to the arctic.

The process of plant breeding involving man's intervention in natural breeding and selection is some 20,000 years old. It has produced remarkable advances in adapting existing species to serve new purposes. The world's economics was largely based on the successes of agriculture for most of these 20,000 years.

Plant breeding involves choosing parents, making crosses to allow recombination of gene (alleles) and searching for and selecting improved forms. Success depends on the genes/alleles available, the combinations required and the ability to create and find the correct combinations necessary to give the desired properties to the plant. Molecular genetics technologies are now capable of providing new genes, new alleles and the means of creating and selecting plants with the new, desired characteristics.

Great agronomic value can result from modulating the size of a plant as a whole or of any of its organs. For example, the green revolution came about as a result of creating dwarf wheat plants, which produced a higher seed yield than taller plants because they could withstand higher levels and inputs of fertilizer and water. Modulation of the size and stature of an entire plant or a particular portion of a plant allows productions of plants specifically improved for agriculture, horticulture and other industries. For example, reductions in height of specific ornamentals, crops and tree species can be beneficial, while increasing height of others may be beneficial.

Increasing the length of the floral stems of cut flowers in some species would also be useful, while increasing leaf size in others would be economically attractive. Enhancing the size of specific plant parts, such as seeds and fruit, to enhance yields by specifically stimulating hormone (e.g. Brassinolide) synthesis in these cells is beneficial. Another application is to stimulate early flowering by altering levels of gibberellic acid in specific cells. Changes in organ size and biomass also results in changes in the mass of constituent molecules.

To summarize, molecular genetic technologies provide the ability to modulate and manipulate plant size and stature of the entire plant as well as at the cell, tissue and organ levels. Thus, plant morphology can be altered to maximize the desired plant trait.

SUMMARY OF THE INVENTION

The present invention, therefore, relates to isolated polynucleotides, polypeptides encoded thereby, and the use of those products for making transgenic plants that are characterized by increased size, have an increased number and size of rosette leaves and are late-flowering, as compared to the non-transformed, wild-type plant.

The present invention also relates to processes for increasing the yield in plants, recombinant nucleic acid molecules and polypeptides used for these processes, their uses as well as to plants with an increased yield.

In the field of agriculture and forestry constantly efforts are being made to produce plants with an increased yield, in particular in order to guarantee the supply of the constantly increasing world population with food and to guarantee the supply of reproducible raw materials. Conventionally, it is tried to obtain plants with an increased yield by breeding, which is, however time-consuming and labor-intensive. Furthermore, appropriate breeding programs have to be performed for each relevant plant species.

Progress has partly been made by the genetic manipulation of plants, that is by introducing into and expressing recombinant nucleic acid molecules in plants. Such approaches have the advantage of usually not being limited to one plant species but being transferable to other plant species. In EP-A 0 511 979, e.g., it was described that the expression of a prokaryotic asparagine synthetase in plant cells inter alia leads to an increased biomass production. In WO 96/21737, e.g., the production of plants with an increased yield by the expression of deregulated or unregulated fructose-1,6-bisphosphatase due to the increase of the photosynthesis rate is described. Nevertheless, there still is a need of generally applicable processes for improving the yield in plants interesting for agriculture or forestry. Therefore, the present invention relates to a process for increasing the yield in plants, characterized in that recombinant DNA molecules stably integrated into the genome of plants are expressed.

It was surprisingly found that the expression of the proteins according to the invention specifically leads to an increase in yield.

The term "increase in yield" preferably relates to an increase of the biomass production, in particular when determined as the fresh weight of the plant. Such an increase in yield preferably refers to the so-called "sink" organs of the plant, which are the organs that take up the photoassimilates produced during photosynthesis. Particularly preferred are parts of plants which can be harvested, such as seeds, fruits, storage roots, roots, tubers, flowers, buds, shoots, stems or wood. The increase in yield according to the invention is at least 3% with regard to the biomass in comparison to non-transformed plants of the same genotype when cultivated under the same conditions, preferably at least 10% and particularly preferred at least 20%.

BRIEF DESCRIPTION OF THE FIGURES

FIG. 1 is a map of the DNA vector CRS 338 utilized in the transformation procedures described herein.

BRIEF DESCRIPTION OF THE INDIVIDUAL TABLES

Table—Reference Tables

The sequences of the instant invention are described in the Sequence Listing and the Reference Table (sometimes referred to as the REF Table. The Reference Table refers to a number of "Maximum Length Sequences" or "MLS." Each MLS corresponds to the longest cDNA and is described in the Av subsection of the Reference Table.

The Reference Table includes the following information relating to each MLS:

I. cDNA Sequence
  A. 5' UTR
  B. Coding Sequence
  C. 3' UTR
II. Genomic Sequence
  A. Exons
  B. Introns
  C. Promoters
III. Link of cDNA Sequences to Clone IDs
IV. Multiple Transcription Start Sites
V. Polypeptide Sequences
  A. Signal Peptide
  B. Domains
  C. Related Polypeptides
VI. Related Polynucleotide Sequences I. cDNA Sequence The Reference Table indicates which sequence in the Sequence Table represents the sequence of each MLS. The MLS sequence can comprise 5' and 3' UTR as well as coding sequences. In addition, specific cDNA clone numbers also are included in the Reference Table when the MLS sequence relates to a specific cDNA clone.

A. 5' UTR

The location of the 5' UTR can be determined by comparing the most 5' MLS sequence with the corresponding genomic sequence as indicated in the Reference Table. The sequence that matches, beginning at any of the transcriptional start sites and ending at the last nucleotide before any of the translational start sites corresponds to the 5' UTR.

B. Coding Region

The coding region is the sequence in any open reading frame found in the MLS. Coding regions of interest are indicated in the PolyP SEQ subsection of the Reference Table.

C. 3' UTR

The location of the 3' UTR can be determined by comparing the most 3' MLS sequence with the corresponding genomic sequence as indicated in the Reference Table. The sequence that matches, beginning at the translational stop site and ending at the last nucleotide of the MLS corresponds to the 3' UTR.

II. Genomic Sequence

Further, the Reference Table indicates the specific "gi" number of the genomic sequence if the sequence resides in a public databank. For each genomic sequence, Reference tables indicate which regions are included in the MLS. These regions can include the 5' and 3' UTRs as well as the coding sequence of the MLS. See, for example, the scheme below:

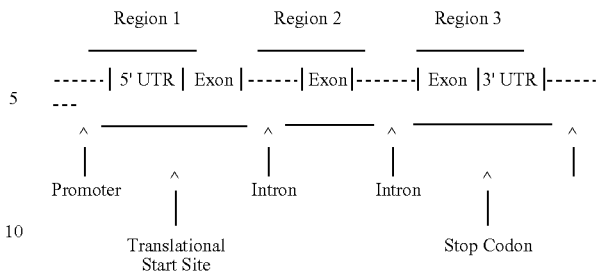

The Reference Table reports the first and last base of each region that are included in an MLS sequence. An example is shown below:
  gi No. 47000:
  37102 ... 37497
  37593 ... 37925

The numbers indicate that the MLS contains the following sequences from two regions of gi No. 47000; a first region including bases 37102-37497, and a second region including bases 37593-37925.

A. Exon Sequences

The location of the exons can be determined by comparing the sequence of the regions from the genomic sequences with the corresponding MLS sequence as indicated by the Reference Table.

i. Initial Exon

To determine the location of the initial exon, information from the
  (1) polypeptide sequence section;
  (2) cDNA polynucleotide section; and
  (3) the genomic sequence section
of the Reference Table is used. First, the polypeptide section will indicate where the translational start site is located in the MLS sequence. The MLS sequence can be matched to the genomic sequence that corresponds to the MLS. Based on the match between the MLS and corresponding genomic sequences, the location of the translational start site can be determined in one of the regions of the genomic sequence. The location of this translational start site is the start of the first exon.

Generally, the last base of the exon of the corresponding genomic region, in which the translational start site was located, will represent the end of the initial exon. In some cases, the initial exon will end with a stop codon, when the initial exon is the only exon.

In the case when sequences representing the MLS are in the positive strand of the corresponding genomic sequence, the last base will be a larger number than the first base. When the sequences representing the MLS are in the negative strand of the corresponding genomic sequence, then the last base will be a smaller number than the first base.

ii. Internal Exons

Except for the regions that comprise the 5' and 3' UTRs, initial exon, and terminal exon, the remaining genomic regions that match the MLS sequence are the internal exons. Specifically, the bases defining the boundaries of the remaining regions also define the intron/exon junctions of the internal exons.

iii. Terminal Exon

As with the initial exon, the location of the terminal exon is determined with information from the
  (1) polypeptide sequence section;
  (2) cDNA polynucleotide section; and
  (3) the genomic sequence section of the Reference Table. The polypeptide section will indicate where the stop codon is located in the MLS sequence. The MLS sequence can be matched to the corresponding genomic sequence. Based on the match between MLS and corresponding genomic sequences, the location of the stop codon can be determined in one of the regions of the genomic sequence. The location of this stop codon is the end of the terminal exon. Generally, the first base of the exon of the corresponding genomic region that matches the cDNA sequence, in which the stop codon was located, will represent the beginning of the terminal exon. In some cases, the translational start site will represent the start of the terminal exon, which will be the only exon.

In the case when the MLS sequences are in the positive strand of the corresponding genomic sequence, the last base will be a larger number than the first base. When the MLS sequences are in the negative strand of the corresponding genomic sequence, then the last base will be a smaller number than the first base.

B. Intron Sequences

In addition, the introns corresponding to the MLS are defined by identifying the genomic sequence located between the regions where the genomic sequence comprises exons. Thus, introns are defined as starting one base downstream of a genomic region comprising an exon, and end one base upstream from a genomic region comprising an exon.

C. Promoter Sequences

As indicated below, promoter sequences corresponding to the MLS are defined as sequences upstream of the first exon; more usually, as sequences upstream of the first of multiple transcription start sites; even more usually as sequences about 2,000 nucleotides upstream of the first of multiple transcription start sites.

III. Link of cDNA Sequences to Clone IDs

As noted above, the Reference Table identifies the cDNA clone(s) that relate to each MLS. The MLS sequence can be longer than the sequences included in the cDNA clones. In such a case, the Reference Table indicates the region of the MLS that is included in the clone. If either the 5' or 3' termini of the cDNA clone sequence is the same as the MLS sequence, no mention will be made.

IV. Multiple Transcription Start Sites

Initiation of transcription can occur at a number of sites of the gene. The Reference Table indicates the possible multiple transcription sites for each gene. In the Reference Table, the location of the transcription start sites can be either a positive or negative number.

The positions indicated by positive numbers refer to the transcription start sites as located in the MLS sequence. The negative numbers indicate the transcription start site within the genomic sequence that corresponds to the MLS.

To determine the location of the transcription start sites with the negative numbers, the MLS sequence is aligned with the corresponding genomic sequence. In the instances when a public genomic sequence is referenced, the relevant corresponding genomic sequence can be found by direct reference to the nucleotide sequence indicated by the "gi" number shown in the public genomic DNA section of the Reference Table. When the position is a negative number, the transcription start site is located in the corresponding genomic sequence upstream of the base that matches the beginning of the MLS sequence in the alignment. The negative number is relative to the first base of the MLS sequence which matches the genomic sequence corresponding to the relevant "gi" number.

In the instances when no public genomic DNA is referenced, the relevant nucleotide sequence for alignment is the nucleotide sequence associated with the amino acid sequence designated by "gi" number of the later PolyP SEQ subsection.

V. Polypeptide Sequences

The PolyP SEQ subsection lists SEQ ID NOS. and Ceres SEQ ID NO for polypeptide sequences corresponding to the coding sequence of the MLS sequence and the location of the translational start site with the coding sequence of the MLS sequence.

The MLS sequence can have multiple translational start sites and can be capable of producing more than one polypeptide sequence.

Subsection (Dp) provides (where present) information concerning amino acid sequences that are found to be related and have some percentage of sequence identity to the polypeptide sequences of the Reference and Sequence Tables. These related sequences are identified by a "gi" number.

Tables 3 and 4—Protein Group Matrix Table

In addition to each consensus sequence of the invention (see below), Applicants have generated a scoring matrix to provide further description of the consensus sequence. The first row of each matrix indicates the residue position in the consensus sequence. The matrix reports the number of occurrences of all the amino acids that were found in the group members for every residue position of the signature sequence. The matrix also indicates for each residue position, how many different organisms were found to have a polypeptide in the group that included a residue at the relevant position. The last line of the matrix indicates all the amino acids that were found at each position of the consensus.

DETAILED DESCRIPTION OF THE INVENTION

1. Definitions

The following terms are utilized throughout this application:

Allelic variant: An "allelic variant" is an alternative form of the same SDF, which resides at the same chromosomal locus in the organism. Allelic variations can occur in any portion of the gene sequence, including regulatory regions. Allelic variants can arise by normal genetic variation in a population. Allelic variants can also be produced by genetic engineering methods. An allelic variant can be one that is found in a naturally occurring plant, including a cultivar or ecotype. An allelic variant may or may not give rise to a phenotypic change, and may or may not be expressed. An allele can result in a detectable change in the phenotype of the trait represented by the locus. A phenotypically silent allele can give rise to a product.

Chimeric: The term "chimeric" is used to describe genes, as defined supra, or constructs wherein at least two of the elements of the gene or construct, such as the promoter and the coding sequence and/or other regulatory sequences and/or filler sequences and/or complements thereof, are heterologous to each other.

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region and the 1' or 2' promoter derived from T-DNA of *Agrobacterium tumefaciens*, and other transcription initiation regions from various plant genes, such as the maize ubiquitin-1 promoter, known to those of skill.

Coordinately Expressed: The term "coordinately expressed," as used in the current invention, refers to genes that are expressed at the same or a similar time and/or stage and/or under the same or similar environmental conditions.

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. Generally, each domain has been associated with either a family of proteins or motifs. Typically, these families and/or motifs have been correlated with specific in-vitro and/or in-vivo activities. A domain can be any length, including the entirety of the sequence of a protein. Detailed descriptions of the domains, associated families and motifs, and correlated activities of the polypeptides of the instant invention are described below. Usually, the polypeptides with designated domain(s) can exhibit at least one activity that is exhibited by any polypeptide that comprises the same domain(s).

Endogenous: The term "endogenous," within the context of the current invention refers to any polynucleotide, polypeptide or protein sequence which is a natural part of a cell or organisms regenerated from said cell.

Exogenous: "Exogenous," as referred to within, is any polynucleotide, polypeptide or protein sequence, whether chimeric or not, that is initially or subsequently introduced into the genome of an individual host cell or the organism regenerated from said host cell by any means other than by a sexual cross. Examples of means by which this can be accomplished are described below, and include *Agrobacterium*-mediated transformation (of dicots—e.g. Salomon et al. *EMBO J.* 3:141 (1984); Herrera-Estrella et al. *EMBO J.* 2:987 (1983); of monocots, representative papers are those by Escudero et al., *Plant J.* 10:355 (1996), Ishida et al., *Nature Biotechnology* 14:745 (1996), May et al., *Bio/Technology* 13:486 (1995)), biolistic methods (Armaleo et al., *Current Genetics* 17:97 1990)), electroporation, in planta techniques, and the like. Such a plant containing the exogenous nucleic acid is referred to here as a $T_0$ for the primary transgenic plant and $T_1$ for the first generation. The term "exogenous" as used herein is also intended to encompass inserting a naturally found element into a non-naturally found location.

Gene: The term "gene," as used in the context of the current invention, encompasses all regulatory and coding sequence contiguously associated with a single hereditary unit with a genetic function. Genes can include non-coding sequences that modulate the genetic function that include, but are not limited to, those that specify polyadenylation, transcriptional regulation, DNA conformation, chromatin conformation, extent and position of base methylation and binding sites of proteins that control all of these. Genes comprised of "exons" (coding sequences), which may be interrupted by "introns" (non-coding sequences), encode proteins. A gene's genetic function may require only RNA expression or protein production, or may only require binding of proteins and/or nucleic acids without associated expression. In certain cases, genes adjacent to one another may share sequence in such a way that one gene will overlap the other. A gene can be found within the genome of an organism, artificial chromosome, plasmid, vector, etc., or as a separate isolated entity.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Homologous gene: In the current invention, "homologous gene" refers to a gene that shares sequence similarity with the gene of interest. This similarity may be in only a fragment of the sequence and often represents a functional domain such as, examples including without limitation a DNA binding domain, a domain with tyrosine kinase activity, or the like. The functional activities of homologous genes are not necessarily the same.

Inducible Promoter: An "inducible promoter" in the context of the current invention refers to a promoter which is regulated under certain conditions, such as light, chemical concentration, protein concentration, conditions in an organism, cell, or organelle, etc. A typical example of an inducible promoter, which can be utilized with the polynucleotides of the present invention, is PARSK1, the promoter from the *Arabidopsis* gene encoding a serine-threonine kinase enzyme, and which promoter is induced by dehydration, abscissic acid and sodium chloride (Wang and Goodman, *Plant J.* 8:37 (1995)). Examples of environmental conditions that may affect transcription by inducible promoters include anaerobic conditions, elevated temperature, or the presence of light Orthologous Gene: In the current invention "orthologous gene" refers to a second gene that encodes a gene product that performs a similar function as the product of a first gene. The orthologous gene may also have a degree of sequence similarity to the first gene. The orthologous gene may encode a polypeptide that exhibits a degree of sequence similarity to a polypeptide corresponding to a first gene. The sequence similarity can be found within a functional domain or along the entire length of the coding sequence of the genes and/or their corresponding polypeptides.

Percentage of sequence identity: "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Plant Promoter: A "plant promoter" is a promoter capable of initiating transcription in plant cells and can drive or facilitate transcription of a fragment of the SDF of the instant invention or a coding sequence of the SDF of the instant invention. Such promoters need not be of plant origin. For example, promoters derived from plant viruses, such as the CaMV35S promoter or from *Agrobacterium tumefaciens* such as the T-DNA promoters, can be plant promoters. A typical example of a plant promoter of plant origin is the maize ubiquitin-1 (ubi-1) promoter known to those of skill.

Promoter: The term "promoter," as used herein, refers to a region of sequence determinants located upstream from the start of transcription of a gene and which are involved in recognition and binding of RNA polymerase and other proteins to initiate and modulate transcription. A basal promoter is the minimal sequence necessary for assembly of a transcription complex required for transcription initiation. Basal promoters frequently include a "TATA box" element usually located between 15 and 35 nucleotides upstream from the site of initiation of transcription. Basal promoters also sometimes include a "CCAAT box" element (typically a sequence CCAAT) and/or a GGGCG sequence, usually located between 40 and 200 nucleotides, preferably 60 to 120 nucleotides, upstream from the start site of transcription.

Regulatory Sequence: The term "regulatory sequence," as used in the current invention, refers to any nucleotide sequence that influences transcription or translation initiation and rate, and stability and/or mobility of the transcript or polypeptide product. Regulatory sequences include, but are not limited to, promoters, promoter control elements, protein binding sequences, 5' and 3' UTRs, transcriptional start site, termination sequence, polyadenylation sequence, introns, certain sequences within a coding sequence, etc.

Signal Peptide: A "signal peptide" as used in the current invention is an amino acid sequence that targets the protein for secretion, for transport to an intracellular compartment or organelle or for incorporation into a membrane. Signal peptides are indicated in the tables and a more detailed description located below.

Specific Promoter: In the context of the current invention, "specific promoters" refers to a subset of inducible promoters that have a high preference for being induced in a specific tissue or cell and/or at a specific time during development of an organism. By "high preference" is meant at least 3-fold, preferably 5-fold, more preferably at least 10-fold still more preferably at least 20-fold, 50-fold or 100-fold increase in transcription in the desired tissue over the transcription in any other tissue. Typical examples of temporal and/or tissue specific promoters of plant origin that can be used with the polynucleotides of the present invention, are: PTA29, a promoter which is capable of driving gene transcription specifically in tapetum and only during anther development (Koltonow et al., *Plant Cell* 2:1201 (1990); RCc2 and RCc3, promoters that direct root-specific gene transcription in rice (Xu et al., *Plant Mol. Biol.* 27:237 (1995); TobRB27, a root-specific promoter from tobacco (Yamamoto et al., *Plant Cell* 3:371 (1991)). Examples of tissue-specific promoters under developmental control include promoters that initiate transcription only in certain tissues or organs, such as root, ovule, fruit, seeds, or flowers. Other suitable promoters include those from genes encoding storage proteins or the lipid body membrane protein, oleosin. A few root-specific promoters are noted above.

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship of hybridization conditions to $T_m$ (in ° C.) is expressed in the mathematical equation $$T_m=81.5-16.6(\log_{10}[Na^+])+0.41(\% \, G+C)-(600/N) \quad (1)$$

Where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m=81.5+16.6 \log\{[Na^+]/(1+0.7[Na^+])\}+ 0.41(\% \, G+C)-500/L \, 0.63(\% \, \text{formamide}) \quad (2)$$

where L is the length of the probe in the hybrid. (P. Tijessen, "Hybridization with Nucleic Acid Probes" in Laboratory Techniques in Biochemistry and Molecular Biology, P. C. van der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., *J. Mol. Biol.* 81:123 (1973)), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Substantially free of: A composition containing A is "substantially free of" B when at least 85% by weight of the total A+B in the composition is A. Preferably, A comprises at least about 90% by weight of the total of A+B in the composition, more preferably at least about 95% or even 99% by weight. For example, a plant gene or DNA sequence can be considered substantially free of other plant genes or DNA sequences.

Translational start site: In the context of the current invention, a "translational start site" is usually an ATG in the cDNA transcript, more usually the first ATG. A single cDNA, however, may have multiple translational start sites.

Transcription start site: "Transcription start site" is used in the current invention to describe the point at which transcription is initiated. This point is typically located about 25 nucleotides downstream from a TFIID binding site, such as a TATA box. Transcription can initiate at one or more sites within the gene, and a single gene may have multiple transcriptional start sites, some of which may be specific for transcription in a particular cell-type or tissue.

Untranslated region (UTR): A "UTR" is any contiguous series of nucleotide bases that is transcribed, but is not translated. These untranslated regions may be associated with particular functions such as increasing mRNA message stability. Examples of UTRs include, but are not limited to polyadenylation signals, terminations sequences, sequences located between the transcriptional start site and the first exon (5' UTR) and sequences located between the last exon and the end of the mRNA (3' UTR).

Variant: The term "variant" is used herein to denote a polypeptide or protein or polynucleotide molecule that differs from others of its kind in some way. For example, polypeptide and protein variants can consist of changes in amino acid sequence and/or charge and/or post-translational modifications (such as glycosylation, etc).

2. Important Characteristics of the Polynucleotides of the Invention

The genes and polynucleotides of the present invention are of interest because when they are misexpressed (i.e. when expressed at a non-material location or in an increased amount) they produce plants with increased height, increased primary inflorescence thickness, an increase in the number and size of leaves, particularly rosette leaves, and a delay in flowering time without reduction in fertility. These traits can be used to exploit or maximize plant products. For example, an increase in plant height is beneficial in species grown or harvested for their main stem or trunk, such as ornamental cut flowers, fiber crops (e.g. flax, kenaf, hesperaloe, hemp) and wood producing trees. Increase in inflorescence thickness is also desirable for some ornamentals, while increases in the number and size of leaves can lead to increased production/harvest from leaf crops such as lettuce, spinach, cabbage and tobacco. The genes of the invention can also be used to increase the size of particular tissues/organs/organelles by placing the gene(s) under the control of a tissue/organ/organelle-specific promoter, to thereby increase particularly the size of the plant fruit and seed.

3. The Genes of the Invention

The sequences of the invention were isolated from *Arabidopsis* (polynucleotide and polypeptide SEQ ID NOS. 29-47), Maize (polynucleotide and polypeptide SEQ ID NOS. 1-14) and *Brassica* (polynucleotide and polypeptide SEQ ID NOS. 15-28), and are considered orthologous genes because the polypeptides perform similar functions in a transgenic plant.

Based upon the orthologous sequences, Applicants have determined that plants having the desired characteristics discussed above can be obtained by transformation of a plant or plant cell with a polynucleotide (stably integrated into the plant genome) that codes for a polypeptide that comprises one of the following consensus sequences:

```
                                           (SEQ ID NO. 49)
(S,E)t<8>(E,G)<2-5>t<11-14>WT(N,D) E+H<2>Ya<1>(S,Y)

aEtSFV<1>Q(L,S)<8-83>(P,E)r<2-4>+<9-89>E<2>(D,G)

QNF<2>n
                                           (SEQ ID NO. 48)
V(E,K)tE(T,P)Ttt(M,G)(Y,I)t(A,K)G(K,N)(E,R)(Y,V)

a<1>t<1-4>WT(N,D)E+H<1>(L,S)Ya(K,S)SMEASFVnQL<0-

30>K(V,A)a<2>(G,E)<2>(Q,E)<9-19>(H,C)<1>(F,V)(L,P)

<1>(S,N)PW<0-2>a<1>+r+P<0-8>tD<2>(E,N)<8>(G,D)<0-

6>S(G,P)t<1>t<2>+<6-17>(Q,K)a<3>(E,S)<1-3>EVtDQNF

<2>n(G,E)(I,A)<1>t(E,S)(N,T)(G,E)t<1>K<2>K<1>(V,R)

(M,R)aS(E,R)t
```

The consensus sequence contains both lower-case and upper-case letters. The upper-case letters represent the standard one-letter amino acid abbreviations. The lower case letters represent classes of amino acids:

"t" refers to tiny amino acids, which are specifically alanine, glycine, serine and threonine.

"p" refers to polar amino acids, which are specifically, asparagine and glutamine "n" refers to negatively charged amino acids, which are specifically, aspartic acid and glutamic acid "+" refers to positively charged residues, which are specifically, lysine, arginine, and histidine "r" refers to aromatic residues, which are specifically, phenylalanine, tyrosine, and tryptophan, "a" refers to aliphatic residues, which are specifically, isoleucine, valine, leucine, and methonine "< >" refers to the number of residues present. For example, A <8>S indicates that eight residues separate the alanine residue from the serine residue. "A<8>S" is equivalent to "A XXXXX XXXS." Likewise "A<1-3>S" indicates that at least one, but as many as three residues separate alanine from serene.

In addition to the sequences of SEQ ID NOS. 1-49, the invention also encompasses variants, fragments or fusions of the polypeptides that produce the same phenotypic effect after transformation into a host plant.

A type of variant of the polypeptides comprises amino acid substitutions. Conservative substitutions are preferred to maintain the function or activity of the polypeptide. Such substitutions include conservation of charge, polarity, hydrophobicity, size, etc. For example, one or more amino acid residues within the sequence can be substituted with another amino acid of similar polarity that acts as a functional equivalent, for example providing a hydrogen bond in an enzymatic catalysis. Substitutes for an amino acid within an exemplified sequence are preferably made among the members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The variants include those that have a percentage of sequence identity to SEQ ID NOS. 1-49 with the range of at least 80%, or preferably at least 85, 90, 95, 96, 97, 98 or 99%. Within that scope of percentage of sequence identity, a polypeptide of the invention may have additional individual amino acids or amino acid sequences inserted into the polypeptide in the middle thereof and/or at the N-terminal and/or C-terminal ends thereof. Likewise, some of the amino acids or amino acid sequences may be deleted from the polypeptide. Amino acid substitutions may also be made in the sequences; conservative substitutions being preferred.

One preferred class of variants are those that comprise (1) the domain of an encoded polypeptide and/or (2) residues conserved between the encoded polypeptide and related polypeptides. For this class of variants, the encoded polypeptide sequence is changed by insertion, deletion, or substitution at positions flanking the domain and/or conserved residues. Another class of variants includes those that comprise an encoded polypeptide sequence that is changed in the domain or conserved residues by a conservative substitution.

4. Use of the Genes to Make Transgenic Plants

To use the sequences of the present invention or a combination of them or parts and/or mutants and/or fusions and/or variants of them, recombinant DNA constructs are prepared which comprise the polynucleotide sequences of the invention inserted into a vector, and which are suitable for transformation of plant cells. The construct can be made using standard recombinant DNA techniques (Sambrook et al. 1989) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al., Proc. Natl. Acad. Sci. USA 89: 8794-8797 (1992); Hamilton et al., Proc. Natl. Acad. Sci. USA 93: 9975-9979 (1996);
(b) YAC: Burke et al., Science 236:806-812 (1987);
(c) PAC: Sternberg N. et al., Proc Natl Acad Sci USA. January; 87(1):103-7 (1990);
(d) Bacteria-Yeast Shuttle Vectors: Bradshaw et al., Nucl Acids Res 23: 4850-4856 (1995);
(e) Lambda Phage Vectors: Replacement Vector, e.g., Frischauf et al., J. Mol. Biol 170: 827-842 (1983); or Insertion vector, e.g., Huynh et al., In: Glover NM (ed) DNA Cloning: A practical Approach, Vol. 1 Oxford: IRL Press (1985); T-DNA gene fusion vectors: Walden et al., Mol Cell Biol 1: 175-194 (1990); and
(g) Plasmid vectors: Sambrook et al., infra.

Typically, the construct will comprise a vector containing a sequence of the present invention with any desired transcriptional and/or translational regulatory sequences, such as promoters, UTRs, and 3' end termination sequences. Vectors can also include origins of replication, scaffold attachment regions (SARs), markers, homologous sequences, introns, etc. The vector may also comprise a marker gene that confers a selectable phenotype on plant cells. The marker may encode biocide resistance, particularly antibiotic resistance, such as resistance to kanamycin, G418, bleomycin, hygromycin, or herbicide resistance, such as resistance to chlorosulfuron or phosphinotricin.

A plant promoter fragment may be used that directs transcription of the gene in all tissues of a regenerated plant and may be a constitutive promoter, such as 35S. Alternatively, the plant promoter may direct transcription of a sequence of the invention in a specific tissue (tissue-specific promoters) or may be otherwise under more precise environmental control (inducible promoters).

If proper polypeptide production is desired, a polyadenylation region at the 3'-end of the coding region is typically included. The polyadenylation region can be derived from the natural gene, from a variety of other plant genes, or from T-DNA.

Knock-In Constructs

Ectopic expression of the sequences of the invention can also be accomplished using a "knock-in" approach. Here, the first component, an "activator line," is created by generating a transgenic plant comprising a transcriptional activator operatively linked to a promoter. The second component comprises the desired cDNA sequence operatively linked to the target binding sequence/region of the transcriptional activator. The second component can be transformed into the "activator line" or be used to transform a host plant to produce a "target" line that can be crossed with the "activator line" by ordinary breeding methods. In either case, the result is the same. That is, the promoter drives production of the transcriptional activator protein that then binds to the target binding region to facilitate expression of the desired cDNA.

Any promoter that functions in plants can be used in the first component, such as the 35S Cauliflower Mosaic Virus promoter or a tissue or organ specific promoter. Suitable transcriptional activator polypeptides include, but are not limited to, those encoding HAP1 and GAL4. The binding sequence recognized and targeted by the selected transcriptional activator protein is used in the second component.

Transformation

Techniques for transforming a wide variety of higher plant species are well known and described in the technical and scientific literature. See, e.g. Weising et al., *Ann. Rev. Genet.* 22:421 (1988); and Christou, Euphytica, v. 85, n. 1-3:13-27, (1995).

Processes for the transformation of monocotyledonous and dicotyledonous plants are known to the person skilled in the art. For the introduction of DNA into a plant host cell a variety of techniques is available. These techniques comprise the transformation of plant cells with T-DNA using *Agrobacterium tumefaciens* or *Agrobacterium rhizogenes* as transformation means, the fusion of protoplasts, the injection, the electroporation of DNA, the introduction of DNA by means of the biolistic method as well as further possibilities.

For the injection and electroporation of DNA in plant cells the plasmids do not have to fulfill specific requirements. Simple plasmids such as pUC derivatives can be used.

The use of *agrobacteria* for the transformation of plant cells has extensively been examined and sufficiently disclosed in the specification of EP-A 120 516, in Hoekema (In: The Binary Plant Vector System Offsetdrukkerij Kanters B. V., Alblasserdam (1985), Chapter V), Fraley et al. (Crit. Rev. Plant. Sci. 4, 1-46) and An et al. (EMBO J. 4 (1985), 277-287).

For the transfer of the DNA to the plant cell plant explants can be co-cultivated with *Agrobacterium tumefaciens* or *Agrobacterium rhizogenes*. From the infected plant material (for example leaf explants, segments of stems, roots but also protoplasts or suspension cultivated plant cells) whole plants can be regenerated in a suitable medium which may contain antibiotics or biozides for the selection of transformed cells. The plants obtained that way can then be examined for the presence of the introduced DNA. Other possibilities for the introduction of foreign DNA using the biolistic method or by protoplast transformation are known (cf., e.g., Willmitzer, L., 1993 Transgenic plants. In: Biotechnology, A Multi-Volume Comprehensive Treatise (H. J. Rehm, G. Reed, A. Pühler, P. Stadler, eds.), Vol. 2, 627-659, VCH Weinheim-New York-Basel-Cambridge).

The transformation of dicotyledonous plants via Ti-plasmid-vector systems with the help of *Agrobacterium tumefaciens* is well-established. Recent studies have indicated that also monocotyledonous plants can be transformed by means of vectors based on *Agrobacterium* (Chan et al., Plant Mol. Biol. 22 (1993), 491-506; Hiei et al., Plant J. 6 (1994), 271-282; Deng et al., Science in China 33 (1990), 28-34; Wilmink et al., Plant Cell Reports 11 (1992), 76-80; May et al., Bio/Technology 13 (1995), 486-492; Conner and Domisse; Int. J. Plant Sci. 153 (1992), 550-555; Ritchie et al., Transgenic Res. 2 (1993), 252-265).

Alternative systems for the transformation of monocotyledonous plants are the transformation by means of the biolistic method (Wan and Lemaux, Plant Physiol. 104 (1994), 37-48; Vasil et al., Bio/Technology 11 (1993), 1553-1558; Ritala et al., Plant Mol. Biol. 24 (1994), 317-325; Spencer et al., Theor. Appl. Genet. 79 (1990), 625-631), the protoplast transformation, the electroporation of partially permeabilized cells, as well as the introduction of DNA by means of glass fibers.

In particular the transformation of maize is described in the literature several times (cf., e.g., WO95/06128, EP 0 513 849; EP 0 465 875; Fromm et al., Biotechnology 8 (1990), 833-844; Gordon-Kamm et al., Plant Cell 2 (1990), 603-618; Koziel et al., Biotechnology 11 (1993), 194-200). In EP 292 435 and in Shillito et al. (Bio/Technology 7 (1989), 581) a process is described with the help of which and starting from a mucus-free, soft (friable) maize callus fertile plants can be obtained. Prioli and Söndahl (Bio/Technology 7 (1989), 589) describe the regenerating and obtaining of fertile plants from maize protoplasts of the Cateto maize inbred line Cat 100-1.

The successful transformation of other cereal species has also been described, for example for barley (Wan and Lemaux, see above; Ritala et al., see above) and for wheat (Nehra et al., Plant J. 5 (1994), 285-297).

Once the introduced DNA has been integrated into the genome of the plant cell, it usually is stable there and is also contained in the progenies of the originally transformed cell. It usually contains a selection marker which makes the transformed plant cells resistant to a biozide or an antibiotic such as kanamycin, G 418, bleomycin, hygromycin or phosphinotricin and others. Therefore, the individually chosen marker should allow the selection of transformed cells from cells lacking the introduced DNA.

The transformed cells grow within the plant in the usual way (see also McCormick et al., Plant Cell Reports 5 (1986), 81-84). The resulting plants can be cultured normally. Seeds can be obtained from the plants.

Two or more generations should be cultivated to make sure that the phenotypic feature is maintained stably and is transmitted. Seeds should be harvested to make sure that the corresponding phenotype or other properties are maintained.

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria (McCormac et al., *Mol. Biotechnol.* 8:199 (1997); Hamilton, *Gene* 200:107 (1997)); Salomon et al. *EMBO J.* 3:141 (1984); Herrera-Estrella et al. *EMBO J.* 2:987 (1983).

Microinjection techniques are known in the art and well described in the scientific and patent literature. The introduction of DNA constructs using polyethylene glycol precipitation is described in Paszkowski et al. *EMBO J.* 3:2717 (1984). Electroporation techniques are described in Fromm et al. *Proc. Natl. Acad. Sci. USA* 82:5824 (1985). Ballistic transformation techniques are described in Klein et al. *Nature* 327:773 (1987). *Agrobacterium tumefaciens*-mediated transformation techniques, including disarming and use of binary or co-integrate vectors, are well described in the scientific literature. See, for example Hamilton, C M., *Gene* 200:107 (1997); Müller et al. *Mol. Gen. Genet.* 207:171 (1987); Komari et al. *Plant J.* 10:165 (1996); Venkateswarlu et al. *Biotechnology* 9:1103 (1991) and Gleave, A P., *Plant Mol. Biol.* 20:1203 (1992); Graves and Goldman, *Plant Mol. Biol.* 7:34 (1986) and Gould et al., *Plant Physiology* 95:426 (1991).

Transformed plant cells that have been obtained by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture* in "Handbook of Plant Cell Culture," pp. 124-176, MacMillan Publishing Company, New York, 1983; and Binding, *Regeneration of Plants, Plant Protoplasts*, pp. 21-73, CRC Press, Boca Raton, 1988. Regeneration can also be obtained from plant callus, explants, organs, or parts thereof. Such regeneration techniques are described generally in Klee et al. *Ann. Rev. of Plant Phys.* 38:467 (1987). Regeneration of monocots (rice) is described by Hosoyama et al. (*Biosci. Biotechnol. Biochem.* 58:1500 (1994)) and by Ghosh et al. (*J. Biotechnol.* 32:1 (1994)). The nucleic acids of the invention can be used to confer the trait of increased height, increased primary inflorescence thickness, an increase in the number and size of leaves and a delay in flowering time, without reduction in fertility, on essentially any plant.

The nucleotide sequences according to the invention can generally encode any appropriate proteins from any organism, in particular from plants, fungi, bacteria or animals. The sequences preferably encode proteins from plants or fungi. Preferably, the plants are higher plants, in particular starch or oil storing useful plants, for example potato or cereals such as rice, maize, wheat, barley, rye, triticale, oat, millet, etc., as well as spinach, tobacco, sugar beet, soya, cotton etc.

The process according to the invention can in principle be applied to any plant. Therefore, monocotyledonous as well as dicotyledonous plant species are particularly suitable. The process is preferably used with plants that are interesting for agriculture, horticulture and/or forestry.

Examples thereof are vegetable plants such as, for example, cucumber, melon, pumpkin, eggplant, zucchini, tomato, spinach, cabbage species, peas, beans, etc., as well as fruits such as, for example, pears, apples, etc.

Thus, the invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linur, Lolium,*

*Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna,* and, *Zea.*

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

5. Phenotype Studies

The genes of the invention were utilized to transform plants (specifically *Arabidopsis* as a model species) and the results show the improved phenotype characteristics of the transgenic plants.

5.1. Phenotype Experiments for Clone 8490

Ectopic expression of cDNA 12337825 (clone 8490—SEQ ID No. 39) under the control of the 35S promoter results in plants having a number of phenotypes including:
  Taller plants
  Thicker inflorescences
  Larger rosettes
  Increased rosette leaf number
  Slightly delayed flowering As a result, misexpression of cDNA 12337825 (SEQ ID No. 39) is useful to increase overall plant size/biomass. A gene with a direct role in controlling the size of an endosperm is also potentially advantageous for seed size and, if misexpressed with an appropriate promoter, for plant growth and development.

Clone 8490 contains cDNA 12337825, which when analyzed in transcript profiling (Txp) experiments (discussed below) was down-regulated in the root meristematic region of the plant relative to root cell elongation zone and up-regulated in an interploidy cross that stimulates endosperm (a paternal tetraploid gives rise to large endosperm and large seed).

Materials and Methods:

Generation and Phenotypic Evaluation of $T_1$ and $T_2$ Lines Containing 35S::cDNA 12337825.

Wild-type *Arabidopsis* Wassilewskija (WS) plants were transformed with a Ti plasmid containing cDNA 12337825 in the sense orientation relative to the 35S constitutive promoter. The Ti plasmid vector used for this construct, CRS 338 (FIG. 1), contains a plant selectable marker gene phosphinothricin acetyltransferase (PAZ) that confers herbicide resistance to transformed plants. The transformation is conducted as follows:

Procedure: *Agrobacterium*-mediated Transformation of *Arabidopsis*

Materials:
0.2% Phytagar
  2 g Phytagar
  1 L nanopure water
YEB (for 1 L)
  5 g extract of meat
  5 g Bacto peptone
  1 g yeast extract
  5 g sucrose
  0.24 g magnesium sulfate
Infiltration Medium (FM) (for 1 L)
  2.2 g MS salts
  50 g sucrose
  5 ul BAP solution (stock is 2 mg/ml)

Methods:
1. Stratification of WS-2 Seed.
   Add 0.5 ml WS-2 (CS2360) seed to 50 ml of 0.2% Phytagar in a 50 ml Corning tube and vortex until seeds and Phytagar form a homogenous mixture.
   Cover tube with foil and stratify at 4° C. for 3 days.
2. Preparation of Seed Mixture.
   Obtain stratified seed from cooler.
   Add seed mixture to a 1000 ml beaker.
   Add an additional 950 ml of 0.2% Phytagar and mix to homogenize.
3. Preparation of Soil Mixture.
   Mix 24 L SunshineMix #5 soil with 16 L Therm-O-Rock vermiculite in cement mixer to make a 60:40 soil mixture.
   Amend soil mixture by adding 2 Tbsp Marathon and 3 Tbsp Osmocote and mix contents thoroughly.
   Add 1 Tbsp Peters fertilizer to 3 gallons of water and add to soil mixture and mix thoroughly.
   Fill 4-inch pots with soil mixture and round the surface to create a slight dome.
   Cover pots with 8-inch squares of nylon netting and fasten using rubber bands.
   Place 14 4-inch pots into each no-hole utility flat.
4. Planting.
   Using a 60 ml syringe, aspirate 35 ml of the seed mixture.
   Exude 25 drops of the seed mixture onto each pot.
   Repeat until all pots have been seeded.
   Place flats on greenhouse bench, cover flat with clear propagation domes, place 55% shade cloth on top of flats and subirrigate by adding 1 inch of water to bottom of each flat.
5. Plant Maintenance.
   3 to 4 days after planting, remove clear lids and shade cloth.
   Subirrigate flats with water as needed.
   After 7-10 days, thin pots to 20 plants per pot using forceps.
   After 2 weeks, subirrigate all plants with Peters fertilizer at a rate of 1 Tsp per gallon water.
   When bolts are about 5-10 cm long, clip them between the first node and the base of stem to induce secondary bolts.
   6 to 7 days after clipping, perform dipping infiltration.
6. Preparation of *Agrobacterium*.
   Add 150 ml fresh YEB to 250 ml centrifuge bottles and cap each with a foam plug (Identi-Plug).
   Autoclave for 40 min at 121° C.
   After cooling to room temperature, uncap and add 0.1 ml each of carbenicillin, spectinomycin and rifampicin stock solutions to each culture vessel.
   Obtain *Agrobacterium* starter block (96-well block with *Agrobacterium* cultures grown to an $OD_{600}$ of approximately 1.0) and inoculate one culture vessel per construct by transferring 1 ml from appropriate well in the starter block.
   Cap culture vessels and place on Lab-Line incubator shaker set at 27° C. and 250 RPM.
   Remove after *Agrobacterium* cultures reach an $OD_{600}$ of approximately 1.0 (about 24 hours), cap culture vessels with plastic caps, place in Sorvall SLA 1500 rotor and centrifuge at 8000 RPM for 8 min at 4° C.
   Pour out supernatant and put bottles on ice until ready to use.
   Add 200 ml Infiltration Media (IM) to each bottle, resuspend *Agrobacterium* pellets and store on ice.

7. Dipping Infiltration.
   Pour resuspended *Agrobacterium* into 16 oz polypropylene containers.
   Invert 4-inch pots and submerge the aerial portion of the plants into the *Agrobacterium* suspension and let stand for 5 min.
   Pour out *Agrobacterium* suspension into waste bucket while keeping polypropylene container in place and return the plants to the upright position.
   Place 10 covered pots per flat.
   Fill each flat with 1-inch of water and cover with shade cloth.
   Keep covered for 24 hr and then remove shade cloth and polypropylene containers.
   Resume normal plant maintenance.
   When plants have finished flowering cover each pot with a ciber plant sleeve.
   After plants are completely dry, collect seed and place into 2.0 ml micro tubes and store in 100-place cryogenic boxes.

Ten independently transformed events were selected and evaluated for their qualitative phenotype in the $T_1$ generation as follows:

Procedure: High Throughput Phenotypic Screening of Misexpression Mutants—T1 Generation 1. Soil Preparation. Wear Gloves at all Times.
   In a large container, mix 60% autoclaved SunshineMix #5 with 40% vermiculite.
   Add 2.5 Tbsp of Osmocote, and 2.5 Tbsp of 1% granular Marathon per 25 L of soil.
   Mix thoroughly.
2. Fill Com-Packs with Soil.
   Loosely fill D601 Com-Packs level to the rim with the prepared soil.
   Place filled pot into utility flat with holes, within a no-hole utility flat.
   Repeat as necessary for planting. One flat set should contain 6 pots.
3. Saturate Soil.
   Evenly water all pots until the soil is saturated and water is collecting in the bottom of the flats.
   After the soil is completely saturated, dump out the excess water.
4. Plant the Seed.
5. Stratify the Seeds.
   After sowing the seed for all the flats, place them into a dark 4° C. cooler.
   Keep the flats in the cooler for 2 nights for WS seed. Other ecotypes may take longer. This cold treatment will help promote uniform germination of the seed.
6. Remove Flats from Cooler and Cover with Shade Cloth. (Shade Cloth is Only Needed in the Greenhouse)
   After the appropriate time, remove the flats from the cooler and place onto growth racks or benches.
   Cover the entire set of flats with 55% shade cloth. The cloth is necessary to cut down the light intensity during the delicate germination period.
   The cloth and domes should remain on the flats until the cotyledons have fully expanded. This usually takes about 4-5 days under standard greenhouse conditions.
7. Remove 55% Shade Cloth and Propagation Domes.
   After the cotyledons have fully expanded, remove both the 55% shade cloth and propagation domes.
8. Spray Plants with Finale Mixture. Wear Gloves and Protective Clothing at all Times.
   Prepare working Finale mixture by mixing 3 ml concentrated Finale in 48 oz of water in the Poly-TEK sprayer.
   Completely and evenly spray plants with a fine mist of the Finale mixture.
   Repeat Finale spraying every 3-4 days until only transformants remain. (Approximately 3 applications are necessary.)
   When satisfied that only transformants remain, discontinue Finale spraying.
9. Weed Out Excess Transformants.
   Weed out excess transformants such that a maximum number of five plants per pot exist evenly spaced throughout the pot.
10. Label Individual Plants.
11. Screen Each Pot for Phenotypes.
    When a phenotype is observed, label a tag describing the phenotype.
    Repeat screening process at 4 development stages: Seedling, Rosette, Flowering, and Senescence.
        Seedling—the time after the cotyledons have emerged, but before the $3^{rd}$ true leaf begins to form.
        Rosette—the time from the emergence of the $3^{rd}$ true leaf through just before the primary bolt begins to elongate.
        Flowering—the time from the emergence of the primary bolt to the onset of senescence (with the exception of noting the flowering time itself, most observations should be made at the stage where approximately 50% of the flowers have opened).
        Senescence—the time following the onset of senescence (with the exception of "delayed senescence", most observations should be made after the plant has completely dried).
12. Quality Control for T1 Overexpressers—Misexpression Lines.
13. Individual Plant Staking.
    During the flowering stage of development, it is necessary to separate individual plants so that they do not entwine themselves, causing cross-contamination and making seed collection very difficult.
    Place a Hyacinth stake in the soil next to the rosette, being careful not to damage the plant.
    Carefully wrap the primary and secondary bolts around the stake.
    Very loosely wrap a single plastic coated twist tie around the stake and the plant to hold it in place.
14. Seed Collection Preparation.
    When senescence begins and flowers stop forming, stop watering. This will allow the plant to dry properly for seed collection.
15. Collect Seed from Plants Two events showing the most advantageous $T_1$ phenotypes (large, late-flowering) were chosen for evaluation in the $T_2$ generation. The $T_2$ growth conditions follow the above $T_1$ protocol. The experimental design differs from the $T_1$ planting in that each $T_2$ plant is contained within its own pot, and no herbicide selection is used. All pots for each $T_2$ event are contained within the same flat and the plants are randomly distributed within each flat. The controls for each set of measurements are the segregating progeny of the given $T_1$ event which do not contain the T-DNA (internal controls). All analyses are done via soil-based experiments under long day light conditions (16 hours) in the Ceres greenhouse.

T2 measurements being taken are as follows:
Days to bolt=number of days between sowing of seed and emergence of first inflorescence.
Number of Leaves=number of rosette leaves present at date of first bolt.
Rosette Area=Area of rosette at time of initial bolt emergence, using ((L×W)*3.14)/4.
Primary Inflorescence Thickness=diameter of primary inflorescence 2.5 cm up from base. This measurement was taken at the termination of flowering/onset of senescence.
Height=length of longest inflorescence from base to apex. This measurement was taken at the termination of flowering/onset of senescence.

PCR was used to amplify the cDNA insert in one randomly chosen $T_1$ plant. This PCR product was then sequenced to confirm that the correct insert was contained in the plants. The quality control process was performed as per standard protocol.

In the $T_2$ generation, PCR was used to confirm the presence or absence of the insert in each plant. To confirm that genomic DNA was present in the reaction mixture, a second set of reactions was run for each sample using primers that amplify a sequence from the RAP2.7 gene. Each sample template yielding a PCR product for RAP2.7 was deemed of adequate template quality.

Results:

Qualitative Analysis of the $T_1$ Plants:
All ten events were late flowering, produced larger rosettes with more leaves and tall, thick inflorescences compared to the controls (see results in Table 5). The transgenic "control" was a set of different 35S::cDNA expressing plants which were indistinguishable from the untransformed WS wild type.

TABLE 5

Qualitative phenotypes observed in 35S::cDNA 12337825 $T_1$ events

| Event | Increased Rosette Size Increased Rosette Leaf Number | Late Flowering | Tall & Thick |
|---|---|---|---|
| ME03459-01 | x | x | x |
| ME03459-02 | x | x | x |
| ME03459-03 | x | x | x |
| ME03459-04 | x | x | x |
| ME03459-05 | x | x | x |
| ME03459-06 | x | x | x |
| ME04358-01 | x | x | x |
| ME04358-02 | x | x | x |
| ME04358-03 | x | x | x |
| ME04358-04 | x | x | x |

Quantitative Analysis of the $T_2$ Plants:
Events ME03459-01 and ME03459-04 were evaluated in greater detail in the $T_2$ generation. Seventeen individuals were sown and observed for event 01, whereas 18 individuals were sown and observed for event 04. The transgenic plants for both events showed increased height, increased primary inflorescence thickness, increased number of rosette leaves, a larger rosette, and delay of flowering time to a 0.05 level of statistical significance (Table 6). Both events had normal fertility. All plants noted in the table as ME03459-01 or ME03459-04 were segregating progeny of the $T_1$ event which we had confirmed to contain the transgene under test. All plants noted in the table as -01 Control or -04 Control were $T_2$ segregating progeny which did not contain the transgene under test (internal controls).

Both events produce significantly more seeds than the control, as would be expected for a typical, fertile, late flowering plant.

Event ME03459-01 is the strongest expresser as noted in Table 5. The rosette area, number of leaves, thickness of the inflorescence and days to bolt are all greater than event -04.

Segregation frequencies of the transgene under test suggest that each event contains a single insert, as calculated by a Chi-square test. The $T_2$ seeds segregate 3R:1S for both events (data not shown).

TABLE 6

Quantitative phenotypes observed in 35S::cDNA 12337825 $T_2$ events

| Event/Control | Number of Observations | Rosette Area (mm$^2$) | Number of Leaves | Height (cm) | Primary Inflorescence Thickness (inches) | Days to Bolt |
|---|---|---|---|---|---|---|
| ME03459-01 | 14 | 7023.0* | 11.0* | 75.6* | 0.068* | 21.9* |
| -01 Control | 3 | 2348.5 | 8.0 | 52.2 | 0.050 | 19.0 |
| ME03459-04 | 9 | 4977.7* | 9.4* | 68.9* | 0.055* | 20.8* |
| -04 Control | 5 | 2521.1 | 7.5 | 54.0 | 0.051 | 18.1 |

*significantly different from control at 0.05 level, via t-test

Summary of Results

The ectopic expression of cDNA 12337825 with a strong constitutive promoter (35S) results in taller plants, with thicker inflorescences, a larger rosette, and more rosette leaves. 12337825 is normally regulated in shoot and root apices, suggesting that the encoded protein may help to regulate meristem function. The increase in plant size observed by this expression is accompanied by a delay in flowering time, but no reduction in fertility. It may also be a useful gene to increase root growth, given the similar expression pattern in shoot meristems and root tip cells.

Assuming conservation of process controlling vegetative growth across species, this gene and protein is likely to function similarly in other species. Increased vegetative biomass should give an improved source:sink ratio and improved fixation of carbon to sucrose and starch. It may in and of itself play into improved yield. Taller inflorescences give the opportunity for more flowers and therefore more seeds. The combination of improved biomass and inflorescence stature may give a significant improvement in yield. Thicker inflorescences may prevent against "snap" against wind, rain or drought. Biomass advantage and presumed photosynthesis advantage should be useful in corn and soybean.

Therefore, this gene/protein is especially useful for controlling the number/rate of cell division in meristems without disturbing overall plant morphology. It could be developed in crops with an appropriate promoter to regulate size and growth rate of many individual organs. The use of a tissue-specific promoter may be particularly desirable. For example, if an increase of leaf size is desired without an increase in root size, the coding sequences of the invention can be operably linked to a leaf specific promoter for this purpose. Alternatively, if an increase in plant size is desired with no change in flowering time, the coding sequences of the invention can be modulated with a leaf specific promoter that does not direct expression in the floral meristem.

The protein is useful for creating sturdier stems in corn and preventing against "snap".

5.2. Phenotype Experiments for Clone 8161—cDNA 5662747

Ectopic expression of Ceres cDNA 5662747 (SEQ ID No. 29) under the control of the 35S promoter results in plants having a number of phenotypes including:
Taller plants
Thicker inflorescences
Qualitatively larger rosettes
Qualitatively increased rosette leaf number
Delayed flowering As a result, misexpression of Ceres cDNA 5662747 (SEQ ID No. 29) is useful to increase overall plant size/biomass.

Clone 8161 contains cDNA 5662747, which when analyzed in transcript profiling experiments (discussed below) was down-regulated in both the shoot and root tips of the plant relative to whole plant mRNA extracts suggesting a function in meristem activity.

Materials and Methods:

Generation and Phenotypic Evaluation of $T_1$ and $T_2$ Lines Containing 35S::cDNA 5662747.

Wild-type *Arabidopsis* Wassilewskija (WS) plants were transformed with a Ti plasmid containing cDNA 5662747 in the sense orientation relative to the 35S constitutive promoter as per standard protocol (See "Ceres Protocol-Agrobacterium-Mediated Transformation of *Arabidopsis*"). The Ti plasmid vector used for this construct, CRS 311, contains a plant selectable marker gene phosphinothricin acetyltransferase (PAT) that confers herbicide resistance to transformed plants.

Ten independently transformed events were selected and evaluated for their qualitative phenotype in the $T_1$ generation as per standard protocol. Three events showing the strongest $T_1$ phenotypes were chosen for evaluation in the $T_2$ generation. The $T_2$ growth conditions followed the above $T_1$ protocol. The experimental design differed from the $T_1$ planting in that each $T_2$ plant was contained with its own pot, and no herbicide selection was used. All the pots for each $T_2$ event were contained within the same flat and the plants were randomly distributed within each flat. The controls for each set of measurements were the segregating progeny of other $T_1$ events which did not contain this gene (internal controls). All analyses were done via soil-based experiments under long day light conditions (16 hours) in the Ceres greenhouse.

T2 measurements were taken as follows:
Height=length of longest inflorescence from base to apex. This measurement was taken at the termination of flowering/onset of senescence.
Primary Inflorescence Thickness=diameter of primary inflorescence 2.5 cm up from base. This measurement was taken at the termination of flowering/onset of senescence.
Days to bolt=number of days between sowing of seed and eruption of first inflorescence.

PCR was used to amplify the cDNA insert in one randomly chosen $T_1$ plant. This PCR product was then sequenced to confirm that the correct insert was contained in the plants. The quality control process was performed as per standard protocol.

In the $T_2$ generation, PCR was used to confirm the presence or absence of the insert in each plant. To confirm that genomic DNA was present in the reaction mixture, a second set of reactions was run for each sample using primers that amplify a sequence from the RAP2.7 gene. Each sample template yielded a PCR product for RAP2.7, so all DNA samples were deemed of adequate template quality.

Results:

Qualitative Analysis of the $T_1$ Plants:

All ten events showed a variety of phenotypes different from wild-type transgenic controls (Table 7); obvious differences from the controls were noted. The transgenic "control" was a set of different 35S::cDNA expressing plants which were indistinguishable from the untransformed WS wildtype. The most pronounced variant phenotype was that of reduced secondary inflorescence formation, slightly delayed flowering time, larger rosettes with more leaves, and tall, thick inflorescences. This pot of plants was used only to provide a size comparison.

TABLE 7

Qualitative phenotypes observed in 35S::cDNA 5662747 $T_1$ events

| Event | Increased Rosette Size Increased Rosette Leaf Number | Late Flowering | Reduced Secondary Inflor. Formation | Tall & Thick | Fertility Defects |
|---|---|---|---|---|---|
| ME01795-01 | x | x | x | x | |
| ME01795-02 | | x | x | x | |
| ME01795-03 | | | | | x |
| ME01795-04 | x | x | x | x | |
| ME01795-05 | | | x | | |
| ME01795-06 | x | x | x | x | |
| ME01795-07 | | x | x | x | |
| ME01795-08 | | | x | | |
| ME01795-09 | | | x | | |
| ME01795-10 | x | x | x | x | |

Quantitative Analysis of the $T_2$ Plants:

Events 01, 04, and 10 were evaluated in greater detail in the $T_2$ generation. Fourteen individuals were sown for each event. The transgenic plants of all 3 events showed increased height, primary inflorescence thickness, and delay of flowering time to a 0.01 level of statistical significance (Table 8). These plants also had qualitatively larger rosettes which contained more leaves (data not shown). All plants, noted in the table as ME01795-01, ME01795-04, or ME01795-10, were segregating progeny of the $T_1$ event which we had confirmed to contain the transgene under test. All plants noted in the table as -01 Control, -04 Control, or -10 Controls were $T_2$ segregating progeny which did not contain the transgene under test (internal controls).

One item of note in the $T_2$ analysis is that the reduced secondary inflorescence formation observed in $T_1$ plants is no longer present in $T_2$ plants. In addition, the delay in flowering time appears to have increased in severity from the $T_1$ to $T_2$ generation.

Segregation frequencies of the transgene under test suggest that each event contains a single insert, as shown by a Chi-square test (Table 8 and data not shown).

TABLE 8

Quantitative phenotypes seen in 35S::cDNA 5662747 $T_2$ events

| Event/Control | Number of Observations | Height (cm) | Primary Inflorescence Thickness (mm) | Days to Bolt |
|---|---|---|---|---|
| ME01795-01 | 8 | 64.3* | 1.062* | 29.8* |
| -01 Control | 6 | 48.3 | 1.048 | 24.5 |
| ME01795-04 | 9 | 70.9* | 1.065* | 35.8* |
| -04 Control | 5 | 42.4* | 1.047 | 25.8 |

TABLE 8-continued

Quantitative phenotypes seen in 35S::cDNA 5662747 T₂ events

| Event/Control | Number of Observations | Height (cm) | Primary Inflorescence Thickness (mm) | Days to Bolt |
|---|---|---|---|---|
| ME01795-10 | 8 | 67.9* | 1.069* | 31.3* |
| -10 Control | 6 | 43.3 | 1.049 | 25.3 |

*significantly different from control at 0.01 level, via t-test

Expression: Ceres clone 8161 is down-regulated in both the shoot apical meristem and root tips of the plant relative to whole plant mRNA extracts.

Summary of Results

The ectopic expression of cDNA 5662747 with a strong constitutive promoter (35S) results in taller plants, with thicker inflorescences, a larger rosette, and more rosette leaves. cDNA 5662747 is normally regulated in shoot and root apices, suggesting that the encoded protein may help to regulate meristem function. The increase in plant size seen by this expression is accompanied by a delay in flowering time, but no reduction in fertility. As the $T_1$ plants had a much less severe delay in flowering than the $T_2$ plants, but still produced the large-plant phenotype, it may be possible to use a promoter of different strength or with a different spatial expression pattern with the cDNA to maintain an increase in plant height and stem/inflorescence thickness without any increase in flowering time. Alternatively, it might be possible to co-express an early flowering gene (e.g., LEAFY) to thereby alleviate/counter balance any late flowering effects. In addition, the gene of the invention (cDNA 5662747) can be utilize to transform a plant line known to have an early flowering characteristic, to thereby create a transformed line with normal flowering time. It may also be a useful gene to increase root growth, given the similar expression pattern in shoot meristems and root tip cells.

Assuming conservation of process controlling vegetative growth across species, this gene and protein is likely to function similarly in other species. Increased vegetative biomass should give an improved source:sink ratio and improved fixation of carbon to sucrose and starch. It may in and of itself play into improved yield. Taller inflorescences give the opportunity for more flowers and therefore more seeds. The combination of improved biomass and inflorescence stature may give a significant improvement in yield. Thicker inflorescences may prevent against "snap" against wind, rain or drought Biomass advantage and presumed photosynthesis advantage should be useful in corn and soybean.

Therefore this gene/protein is especially useful for controlling the number/rate of cell division in meristems without disturbing overall plant morphology. It could be developed in crops with an appropriate promoter to regulate size and growth rate of many individual organs. The use of a tissue-specific promoter may be particularly desirable. For example, if an increase of leaf size is desired without an increase in root size, the coding sequences of the invention can be operably linked to a leaf specific promoter for this purpose. Alternatively, if an increase in plant size is desired with no change in flowering time, the coding sequences of the invention can be modulated with a leaf specific promoter that does not direct expression in the floral meristem.

Microarray Analysis

A major way that a cell controls its response to internal or external stimuli is by regulating the rate of transcription of specific genes. For example, the differentiation of cells during organogenesis into forms characteristic of the organ is associated with the selective activation and repression of large numbers of genes. Thus, specific organs, tissues and cells are functionally distinct due to the different populations of mRNAs and protein products they possess. Internal signals program the selective activation and repression programs. For example, internally synthesized hormones produce such signals. The level of hormone can be raised by increasing the level of transcription of genes encoding proteins concerned with hormone synthesis.

To measure how a cell reacts to internal and/or external stimuli, individual mRNA levels can be measured and used as an indicator for the extent of transcription of the gene. Cells can be exposed to a stimulus, and mRNA can be isolated and assayed at different time points after stimulation. The mRNA from the stimulated cells can be compared to control cells that were not stimulated. The mRNA levels that are higher in the stimulated cell versus the control indicate a stimulus-specific response of the cell. The same is true of mRNA levels that are lower in stimulated cells versus the control condition.

Similar studies can be performed with cells taken from an organism with a defined mutation in their genome as compared with cells without the mutation. Altered mRNA levels in the mutated cells indicate how the mutation causes transcriptional changes. These transcriptional changes are associated with the phenotype that the mutated cells exhibit that is different from the phenotype exhibited by the control cells.

Applicants have utilized microarray techniques to measure the levels of mRNAs in cells from plants transformed with the polynucleotides of the invention. In general, transformants with the genes of the invention were grown to an appropriate stage, and tissue samples were prepared for the microarray differential expression analysis.

Microarray Experimental Procedures and Results

Procedures

A summary of the parameters utilized for each of the differential expression analysis experiments is provided in TABLE 9.

1. Sample Tissue Preparation

Tissue samples for each of the expression analysis experiments were prepared as follows:

(a) Roots

Seeds of *Arabidopsis thaliana* (Ws) were sterilized in full strength bleach for less than 5 min., washed more than 3 times in sterile distilled deionized water and plated on MS agar plates. The plates were placed at 4° C. for 3 nights and then placed vertically into a growth chamber having 16 hr light/8 hr dark cycles, 23° C., 70% relative humidity and ~11,000 LUX. After 2 weeks, the roots were cut from the agar, flash frozen in liquid nitrogen and stored at −80° C.

(b) Rosette Leaves, Stems, and Siliques

*Arabidopsis thaliana* (Ws) seed was vernalized at 4° C. for 3 days before sowing in Metro-mix soil type 350. Flats were placed in a growth chamber having 16 hr light/8 hr dark, 80% relative humidity, 23° C. and 13,000 LUX for germination and growth. After 3 weeks, rosette leaves, stems, and siliques were harvested, flash frozen in liquid nitrogen and stored at −80° C. until use. After 4 weeks, siliques (<5 mm, 5-10 mm and >10 mm) were harvested, flash frozen in liquid nitrogen and stored at −80° C. until use. 5 week old whole plants (used as controls) were harvested, flash frozen in liquid nitrogen and kept at −80° C. until RNA was isolated.

(c) Germination

*Arabidopsis thaliana* seeds (ecotype Ws) were sterilized in bleach and rinsed with sterile water. The seeds were placed in 100 mm petri plates containing soaked autoclaved filter paper. Plates were foil-wrapped and left at 4° C. for 3 nights to vernalize. After cold treatment, the foil was removed and plates were placed into a growth chamber having 16 hr light/8 hr dark cycles, 23° C., 70% relative humidity and ~11,000 lux. Seeds were collected 1 d, 2 d, 3 d and 4 d later, flash frozen in liquid nitrogen and stored at −80° C. until RNA was isolated.

(d) Abscissic Acid (ABA)

Seeds of *Arabidopsis thaliana* (ecotype Wassilewskija) were sown in trays and left at 4° C. for 4 days to vernalize. They were then transferred to a growth chamber having grown 16 hr light/8 hr dark, 13,000 LUX, 70% humidity, and 20° C. and watered twice a week with 1 L of 1× Hoagland's solution. Approximately 1,000 14 day old plants were spayed with 200-250 mls of 100 µM ABA in a 0.02% solution of the detergent Silwet L-77. Whole seedlings, including roots, were harvested within a 15 to 20 minute time period at 1 hr and 6 hr after treatment, flash-frozen in liquid nitrogen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 100 µM ABA for treatment. Control plants were treated with water. After 6 hr and 24 hr, aerial and root tissues were separated and flash frozen in liquid nitrogen prior to storage at −80° C.

(e) Brassinosteroid Responsive

Two separate experiments were performed, one with epi-brassinolide and one with the brassinosteroid biosynthetic inhibitor brassinazole. In the epi-brassinolide experiments, seeds of wild-type *Arabidopsis thaliana* (ecotype Wassilewskija) and the brassinosteroid biosynthetic mutant dwf4-1 were sown in trays and left at 4° C. for 4 days to vernalize. They were then transferred to a growth chamber having 16 hr light/8 hr dark, 11,000 LUX, 70% humidity and 22° C. temperature. Four week old plants were spayed with a 1 µM solution of epi-brassinolide and shoot parts (unopened floral primordia and shoot apical meristems) harvested three hours later. Tissue was flash-frozen in liquid nitrogen and stored at −80° C. In the brassinazole experiments, seeds of wild-type *Arabidopsis thaliana* (ecotype Wassilewskija) were grown as described above. Four week old plants were spayed with a 1 µM solution of brassinazole and shoot parts (unopened floral primordia and shoot apical meristems) harvested three hours later. Tissue was flash-frozen in liquid nitrogen and stored at −80° C.

In addition to the spray experiments, tissue was prepared from two different mutants; (1) a dwf4-1 knock out mutant and (2) a mutant overexpressing the dwf4-1 gene.

Seeds of wild-type *Arabidopsis thaliana* (ecotype Wassilewskija) and of the dwf4-1 knock out and overexpressor mutants were sown in trays and left at 4° C. for 4 days to vernalize. They were then transferred to a growth chamber having 16 hr light/8 hr dark, 11,000 LUX, 70% humidity and 22° C. temperature. Tissue from shoot parts (unopened floral primordia and shoot apical meristems) was flash-frozen in liquid nitrogen and stored at −80° C.

Another experiment was completed with seeds of *Arabidopsis thaliana* (ecotype Wassilewskija) were sown in trays and left at 4° C. for 4 days to vernalize. They were then transferred to a growth chamber. Plants were grown under long-day (16 hr light: 8 hr. dark) conditions, 13,000 LUX light intensity, 70% humidity, 20° C. temperature and watered twice a week with 1 L 1× Hoagland's solution (recipe recited in Feldmann et al., (1987) Mol. Gen. Genet. 208: 1-9 and described as complete nutrient solution). Approximately 1,000 14 day old plants were spayed with 200-250 mls of 0.1 µM Epi-Brassinolite in 0.02% solution of the detergent Silwet L-77. At 1 hr. and 6 hrs. after treatment aerial tissues were harvested within a 15 to 20 minute time period and flash-frozen in liquid nitrogen.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 0.1 µM epi-brassinolide for treatment. Control plants were treated with distilled deionized water. After 24 hr, aerial and root tissues were separated and flash frozen in liquid nitrogen prior to storage at −80° C.

(f) Nitrogen: High to Low

Wild type *Arabidopsis thaliana* seeds (ecotype Ws) were surface sterilized with 30% Clorox, 0.1% Triton X-100 for 5 minutes. Seeds were then rinsed with 4-5 exchanges of sterile double distilled deionized water. Seeds were vernalized at 4° C. for 2-4 days in darkness. After cold treatment, seeds were plated on modified 1×MS media (without $NH_4NO_3$ or $KNO_3$), 0.5% sucrose, 0.5 g/L MES pH5.7, 1% phytagar and supplemented with $KNO_3$ to a final concentration of 60 mM (high nitrate modified 1×MS media). Plates were then grown for 7 days in a Percival growth chamber at 22° C. with 16 hr. light/8 hr dark.

Germinated seedlings were then transferred to a sterile flask containing 50 mL of high nitrate modified 1×MS liquid media. Seedlings were grown with mild shaking for 3 additional days at 22° C. in 16 hr. light/8 hr dark (in a Percival growth chamber) on the high nitrate modified 1×MS liquid media.

After three days of growth on high nitrate modified 1×MS liquid media, seedlings were transferred either to a new sterile flask containing 50 mL of high nitrate modified 1×MS liquid media or to low nitrate modified 1×MS liquid media (containing 20 µM $KNO_3$). Seedlings were grown in these media conditions with mild shaking at 22° C. in 16 hr light/8 hr dark for the appropriate time points and whole seedlings harvested for total RNA isolation via the Trizol method (LifeTech.). The time points used for the microarray experiments were 10 min. and 1 hour time points for both the high and low nitrate modified 1×MS media.

Alternatively, seeds that were surface sterilized in 30% bleach containing 0.1% Triton X-100 and further rinsed in sterile water, were planted on MS agar, (0.5% sucrose) plates containing 50 mM $KNO_3$ (potassium nitrate). The seedlings were grown under constant light (3500 LUX) at 22° C. After 12 days, seedlings were transferred to MS agar plates containing either 1 mM $KNO_3$ or 50 mM $KNO_3$. Seedlings transferred to agar plates containing 50 mM $KNO_3$ were treated as controls in the experiment. Seedlings transferred to plates with 1 mM $KNO_3$ were rinsed thoroughly with sterile MS solution containing 1 mM $KNO_3$. There were ten plates per transfer. Root tissue was collected and frozen in 15 mL Falcon tubes at various time points which included 1 hour, 2 hours, 3 hours, 4 hours, 6 hours, 9 hours, 12 hours, 16 hours, and 24 hours.

Maize 35A19 Pioneer hybrid seeds were sown on flats containing sand and grown in a Conviron growth chamber at 25° C., 16 hr light/8 hr dark, ~13,000 LUX and 80% relative humidity. Plants were watered every three days with double distilled deionized water. Germinated seedlings are allowed to grow for 10 days and were watered with high nitrate modified 1×MS liquid media (see above). On day 11, young corn seedlings were removed from the sand (with their roots intact) and rinsed briefly in high nitrate modified 1×MS liquid media. The equivalent of half a flat of seedlings were then submerged (up to their roots) in a beaker containing either 500 mL of high or low nitrate modified 1×MS liquid media (see above for details).

At appropriate time points, seedlings were removed from their respective liquid media, the roots separated from the shoots and each tissue type flash frozen in liquid nitrogen and stored at −80° C. This was repeated for each time point. Total RNA was isolated using the Trizol method (see above) with root tissues only.

Corn root tissues isolated at the 4 hr and 16 hr time points were used for the microarray experiments. Both the high and low nitrate modified 1×MS media were used.

(g) Nitrogen: Low to High

*Arabidopsis thaliana* ecotype Ws seeds were sown on flats containing 4 L of a 1:2 mixture of Grace Zonolite vermiculite and soil. Flats were watered with 3 L of water and vernalized at 4° C. for five days. Flats were placed in a Conviron growth chamber having 16 hr light/8 hr dark at 20° C., 80% humidity and 17,450 LUX. Flats were watered with approximately 1.5 L of water every four days. Mature, bolting plants (24 days after germination) were bottom treated with 2 L of either a control (100 mM mannitol pH 5.5) or an experimental (50 mM ammonium nitrate, pH 5.5) solution. Roots, leaves and siliques were harvested separately 30, 120 and 240 minutes after treatment, flash frozen in liquid nitrogen and stored at −80° C.

Hybrid maize seed (Pioneer hybrid 35A19) were aerated overnight in deionized water. Thirty seeds were plated in each flat, which contained 4 liters of Grace zonolite vermiculite. Two liters of water were bottom fed and flats were kept in a Conviron growth chamber with 16 hr light/8 hr dark at 20° C. and 80% humidity. Flats were watered with 1 L of tap water every three days. Five day old seedlings were treated as described above with 2 L of either a control (100 mM mannitol pH 6.5) solution or 1 L of an experimental (50 mM ammonium nitrate, pH 6.8) solution. Fifteen shoots per time point per treatment were harvested 10, 90 and 180 minutes after treatment, flash frozen in liquid nitrogen and stored at −80° C.

Alternatively, seeds of *Arabidopsis thaliana* (ecotype Wassilewskija) were left at 4° C. for 3 days to vernalize. They were then sown on vermiculite in a growth chamber having 16 hours light/8 hours dark, 12,000-14,000 LUX, 70% humidity, and 20° C. They were bottom-watered with tap water, twice weekly. Twenty-four days old plants were sprayed with either water (control) or 0.6% ammonium nitrate at 4 μL/cm$^2$ of tray surface. Total shoots and some primary roots were cleaned of vermiculite, flash-frozen in liquid nitrogen and stored at −80° C.

(h) Methyl Jasmonate

Seeds of *Arabidopsis thaliana* (ecotype Wassilewskija) were sown in trays and left at 4° C. for 4 days to vernalize before being transferred to a growth chamber having 16 hr light/8 hr. dark, 13,000 LUX, 70% humidity, 20° C. temperature and watered twice a week with 1 L of a 1× Hoagland's solution. Approximately 1,000 14 day old plants were spayed with 200-250 mls of 0.001% methyl jasmonate in a 0.02% solution of the detergent Silwet L-77. At 1 hr and 6 hrs after treatment, whole seedlings, including roots, were harvested within a 15 to 20 minute time period, flash-frozen in liquid nitrogen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 0.001% methyl jasmonate for treatment. Control plants were treated with water. After 24 hr, aerial and root tissues were separated and flash frozen in liquid nitrogen prior to storage at −80° C.

(i) Salicylic Acid

Seeds of *Arabidopsis thaliana* (ecotype Wassilewskija) were sown in trays and left at 4° C. for 4 days to vernalize before being transferred to a growth chamber having 16 hr light/8 hr. dark, 13,000 LUX, 70% humidity, 20° C. temperature and watered twice a week with 1 L of a 1× Hoagland's solution. Approximately 1,000 14 day old plants were spayed with 200-250 mls of 5 mM salicylic acid (solubilized in 70% ethanol) in a 0.02% solution of the detergent Silwet L-77. At 1 hr and 6 hrs after treatment, whole seedlings, including roots, were harvested within a 15 to 20 minute time period flash-frozen in liquid nitrogen and stored at −80° C.

Alternatively, seeds of wild-type *Arabidopsis thaliana* (ecotype Columbia) and mutant CS3726 were sown in soil type 200 mixed with osmocote fertilizer and Marathon insecticide and left at 4° C. for 3 days to vernalize. Flats were incubated at room temperature with continuous light. Sixteen days post germination plants were sprayed with 2 mM SA, 0.02% SilwettL-77 or control solution (0.02% SilwettL-77. Aerial parts or flowers were harvested 1 hr, 4 hr, 6 hr, 24 hr and 3 weeks post-treatment flash frozen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 2 mM SA for treatment. Control plants were treated with water. After 12 hr and 24 hr, aerial and root tissues were separated and flash frozen in liquid nitrogen prior to storage at −80° C.

(j) Drought Stress

Seeds of *Arabidopsis thaliana* (Wassilewskija) were sown in pots and left at 4° C. for three days to vernalize before being transferred to a growth chamber having 16 hr light/8 hr dark, 150,000-160,000 LUX 20° C. and 70% humidity. After 14 days, aerial tissues were cut and left to dry on 3 MM Whatman paper in a petri-plate for 1 hour and 6 hours. Aerial tissues exposed for 1 hour and 6 hours to 3 MM Whatman paper wetted with 1× Hoagland's solution served as controls. Tissues were harvested, flash-frozen in liquid nitrogen and stored at −80° C.

Alternatively, *Arabidopsis thaliana* (Ws) seed was vernalized at 4° C. for 3 days before sowing in Metromix soil type 350. Flats were placed in a growth chamber with 23° C., 16 hr light/8 hr. dark, 80% relative humidity, ~13,000 LUX for germination and growth. Plants were watered with 1-1.5 L of water every four days. Watering was stopped 16 days after germination for the treated samples, but continued for the control samples. Rosette leaves and stems, flowers and siliques were harvested 2 d, 3 d, 4 d, 5 d, 6 d and 7 d after watering was stopped. Tissue was flash frozen in liquid nitrogen and kept at −80° C. until RNA was isolated. Flowers and siliques were also harvested on day 8 from plants that had undergone a 7 d drought treatment followed by 1 day of watering. Control plants (whole plants) were harvested after 5 weeks, flash frozen in liquid nitrogen and stored as above.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in empty 1-liter beakers at room temperature for treatment. Control plants were placed in water. After 1 hr, 6 hr, 12 hr and 24 hr aerial and root tissues were separated and flash frozen in liquid nitrogen prior to storage at −80° C.

(k) Osmotic Stress

Seeds of *Arabidopsis thaliana* (Wassilewskija) were sown in trays and left at 4° C. for three days to vernalize before being transferred to a growth chamber having 16 hr light/8 hr dark, 12,000-14,000 LUX, 20° C., and 70% humidity. After 14 days, the aerial tissues were cut and placed on 3 MM Whatman-paper in a petri-plate wetted with 20% PEG (polyethylene glycol-$M_r$ 8,000) in 1× Hoagland's solution. Aerial tissues on 3 MM Whatman paper containing 1× Hoagland's solution alone served as the control. Aerial tissues were harvested at 1 hour and 6 hours after treatment, flash-frozen in liquid nitrogen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 10% PEG (polyethylene glycol-$M_r$ 8,000) for treatment. Control plants were treated with water. After 1 hr and 6 hr aerial and root tissues were separated and flash frozen in liquid nitrogen prior to storage at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 150 mM NaCl for treatment. Control plants were treated with water. After 1 hr, 6 hr, and 24 hr aerial and root tissues were separated and flash frozen in liquid nitrogen prior to storage at −80° C.

(l) Heat Shock Treatment

Seeds of *Arabidopsis Thaliana* (Wassilewskija) were sown in trays and left at 4° C. for three days to vernalize before being transferred to a growth chamber with 16 hr light/8 hr dark, 12,000-14,000 Lux, 70% humidity and 20° C., fourteen day old plants were transferred to a 42° C. growth chamber and aerial tissues were harvested 1 hr and 6 hr after transfer. Control plants were left at 20° C. and aerial tissues were harvested. Tissues were flash-frozen in liquid nitrogen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers containing 42° C. water for treatment. Control plants were treated with water at 25° C. After 1 hr and 6 hr aerial and root tissues were separated and flash frozen in liquid nitrogen prior to storage at −80° C.

(m) Cold Shock Treatment

Seeds of *Arabidopsis thaliana* (Wassilewskija) were sown in trays and left at 4° C. for three days to vernalize before being transferred to a growth chamber having 16 hr light/8 hr dark, 12,000-14,000 LUX, 20° C. and 70% humidity. Fourteen day old plants were transferred to a 4° C. dark growth chamber and aerial tissues were harvested 1 hour and 6 hours later. Control plants were maintained at 20° C. and covered with foil to avoid exposure to light. Tissues were flash-frozen in liquid nitrogen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers containing 4° C. water for treatment. Control plants were treated with water at 25° C. After 1 hr and 6 hr aerial and root tissues were separated and flash frozen in liquid nitrogen prior to storage at −80° C.

(n) *Arabidopsis* Seeds

Fruits (Pod+Seed) 0-5 mm

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Siliques 0-5 mm in length containing post fertilization through pre-heart stage [0-72 hours after fertilization (HAF)] embryos were harvested and flash frozen in liquid nitrogen.

Fruits (Pod+Seed) 5-10 mm

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Siliques 5-10 nm in length containing heart-through early upturned-U-stage [72-120 hours after fertilization (HAF)] embryos were harvested and flash frozen in liquid nitrogen.

Fruits (Pod+Seed) >10 mm

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Siliques >10 mm in length containing green, late upturned-U-stage [>120 hours after fertilization (HAF)-9 days after flowering (DAF)] embryos were harvested and flash frozen in liquid nitrogen.

Green Pods 5-10 mm (Control Tissue for Samples 72-74)

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Green siliques 5-10 mm in length containing developing seeds 72-120 hours after fertilization (HAF)] were opened and the seeds removed. The remaining tissues (green pods minus seed) were harvested and flash frozen in liquid nitrogen.

Green Seeds from Fruits >10 mm

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Green siliques >10 mm in length containing developing seeds up to 9 days after flowering (DAF)] were opened and the seeds removed and harvested and flash frozen in liquid nitrogen.

Brown Seeds from Fruits >10 mm

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Yellowing siliques >10 mm in length containing brown, dessicating seeds >11 days after flowering (DAF)] were opened and the seeds removed and harvested and flash frozen in liquid nitrogen.

Green/Brown Seeds from Fruits >10 mm

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Green siliques >10 mm in length containing both green and brown seeds >9 days after flowering (DAF)] were opened and the seeds removed and harvested and flash frozen in liquid nitrogen.

Mature Seeds (24 Hours after Imbibition)

Mature dry seeds of *Arabidopsis thaliana* (ecotype Wassilewskija) were sown onto moistened filter paper and left at 4° C. for two to three days to vernalize. Imbibed seeds were then transferred to a growth chamber [16 hr light: 8 hr dark conditions, 7000-8000 LUX light intensity, 70% humidity, and 22° C. temperature], the emerging seedlings harvested after 48 hours and flash frozen in liquid nitrogen.

Mature Seeds (Dry)

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature and taken to maturity. Mature dry seeds are collected, dried for one week at 28° C., and vernalized for one week at 4° C. before used as a source of RNA.

(o) Herbicide Treatment

*Arabidopsis thaliana* (Ws) seeds were sterilized for 5 min. with 30% bleach, 50 µl Triton in a total volume of 50 ml. Seeds were vernalized at 4° C. for 3 days before being plated onto GM agar plates at a density of about 144 seeds per plate. Plates were incubated in a Percival growth chamber having 16 hr light/8 hr dark, 80% relative humidity, 22° C. and 11,000 LUX for 14 days.

Plates were sprayed (~0.5 mls/plate) with water, Finale (1.128 g/L), Glean (1.88 g/L), RoundUp (0.01 g/L) or Trimec (0.08 g/L). Tissue was collected and flash frozen in liquid nitrogen at the following time points: 0, 1, 2, 4, 8, 12 and 24 hours. Frozen tissue was stored at −80° C. prior to RNA isolation.

(p) Root Tips

Seeds of *Arabidopsis thaliana* (ecotype Ws) were placed on MS plates and vernalized at 4° C. for 3 days before being placed in a 25° C. growth chamber having 16 hr light/8 hr dark, 70% relative humidity and about 3 $W/m^2$. After 6 days, young seedlings were transferred to flasks containing B5 liquid medium, 1% sucrose and 0.05 mg/l indole-3-butyric acid. Flasks were incubated at room temperature with 100 rpm agitation. Media was replaced weekly. After three weeks, roots were harvested and incubated for 1 hr with 2% pectinase, 0.2% cellulase, pH 7 before straining through a #80 (Sigma) sieve. The root body material remaining on the sieve (used as the control) was flash frozen and stored at −80° C. until use. The material that passed through the #80 sieve was strained through a #200 (Sigma) sieve and the material remaining on the sieve (root tips) was flash frozen and stored at −80° C. until use. Approximately 10 mg of root tips were collected from one flask of root culture.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 8 days. Seedlings were carefully removed from the sand and the root tips (~2 mm long) were removed and flash frozen in liquid nitrogen prior to storage at −80° C. The tissues above the root tips (~1 cm long) were cut, treated as above and used as control tissue.

(q) Imbibed Seed

Seeds of maize hybrid 35A (Pioneer) were sown in water-moistened sand in covered flats (10 rows, 5-6 seed/row) and covered with clear, plastic lids before being placed in a growth chamber having 16 hr light (25° C.)/8 hr dark (20° C.), 75% relative humidity and 13,000-14,000 LUX. One day after sowing, whole seeds were flash frozen in liquid nitrogen prior to storage at −80° C. Two days after sowing, embryos and endosperm were isolated and flash frozen in liquid nitrogen prior to storage at −80° C. On days 3-6, aerial tissues, roots and endosperm were isolated and flash frozen in liquid nitrogen prior to storage at −80° C.

(r) Flowers (Green, White or Buds)

Approximately 10 □l of *Arabidopsis thaliana* seeds (ecotype Ws) were sown on 350 soil (containing 0.03% marathon) and vernalized at 4 C for 3 days. Plants were then grown at room temperature under fluorescent lighting until flowering. Flowers were harvested after 28 days in three different categories. Buds that had not opened at all and were completely green were categorized as "flower buds" (also referred to as green buds by the investigator). Buds that had started to open, with white petals emerging slightly were categorized as "green flowers" (also referred to as white buds by the investigator). Flowers that had opened mostly (with no silique elongation) with white petals completely visible were categorized as "white flowers" (also referred to as open flowers by the investigator). Buds and flowers were harvested with forceps, flash frozen in liquid nitrogen and stored at −80 C until RNA was isolated.

2. Microarray Hybridization Procedures

Microarray technology provides the ability to monitor mRNA transcript levels of thousands of genes in a single experiment. These experiments simultaneously hybridize two differentially labeled fluorescent cDNA pools to glass slides that have been previously spotted with cDNA clones of the same species. Each arrayed cDNA spot will have a corresponding ratio of fluorescence that represents the level of disparity between the respective mRNA species in the two sample pools. Thousands of polynucleotides can be spotted on one slide, and each experiment generates a global expression pattern.

Coating Slides

The microarray consists of a chemically coated microscope slide, referred herein as a "chip" with numerous polynucleotide samples arrayed at a high density. The poly-L-lysine coating allows for this spotting at high density by providing a hydrophobic surface, reducing the spreading of spots of DNA solution arrayed on the slides. Glass microscope slides (Gold Seal #3010 manufactured by Gold Seal Products, Portsmouth, N.H., USA) were coated with a 0.1% W/V solution of Poly-L-lysine (Sigma, St. Louis, Mo.) using the following protocol:

1. Slides were placed in slide racks (Shandon Lipshaw #121). The racks were then put in chambers (Shandon Lipshaw #121).
2. Cleaning solution was prepared:
   70 g NaOH was dissolved in 280 mL ddH2O.
   420 mL 95% ethanol was added. The total volume was 700 mL (=2×350 mL); it was stirred until completely mixed. If the solution remained cloudy, ddH$_2$O was added until clear.
3. The solution was poured into chambers with slides; the chambers were covered with glass lids. The solution was mixed on an orbital shaker for 2 hr.
4. The racks were quickly transferred to fresh chambers filled with ddH$_2$O. They were rinsed vigorously by plunging racks up and down. Rinses were repeated 4× with fresh ddH$_2$O each time, to remove all traces of NaOH-ethanol.
5. Polylysine solution was prepared:
   0 mL poly-L-lysine+70 mL tissue culture PBS in 560 mL water, using plastic graduated cylinder and beaker.
6. Slides were transferred to polylysine solution and shaken for 1 hr.
7. The rack was transferred to a fresh chambers filled with ddH$_2$O. It was plunged up and down 5× to rinse.
8. The slides were centrifuged on microtiter plate carriers (paper towels were placed below the rack to absorb liquid) for 5 min. @ 500 rpm. The slide racks were transferred to empty chambers with covers.
9. Slide racks were dried in a 45 C oven for 10 min.
10. The slides were stored in a closed plastic slide box.
11. Normally, the surface of lysine coated slides was not very hydrophobic immediately after this process, but became increasingly hydrophobic with storage. A hydrophobic surface helped ensure that spots didn't run together while printing at high densities. After they aged for 10 days to a month the slides were ready to use. However, coated slides that have been sitting around for long periods of time were usually too old to be used. This was because they developed opaque patches, visible when held to the light, and these resulted in high background hybridization from the fluorescent probe. Alternatively, pre-coated glass slides were purchased from TeleChem International, Inc. (Sunnyvale, Calif., 94089; catalog number SMM-25, Superamine substrates).

PCR Amplification of cDNA Clone Inserts

Polynucleotides were amplified from *Arabidopsis* cDNA clones using insert specific probes. The resulting 100 uL PCR reactions were purified with Qiaquick 96 PCR purification columns (Qiagen, Valencia, Calif., USA) and eluted in 30 uL of 5 mM Tris. 8.5 uL of the elution were mixed with 1.5 uL of 20×SSC to give a final spotting solution of DNA in 3×SSC. The concentrations of DNA generated from each clone varied between 10-100 ng/ul, but were usually about 50 ng/ul.

Arraying of PCR Products on Glass Slides

PCR products from cDNA clones were spotted onto the poly-L-Lysine coated glass slides using an arrangement of quill-tip pins (ChipMaker 3 spotting pins; Telechem, International, Inc., Sunnyvale, Calif., USA) and a robotic arrayer (PixSys 3500, Cartesian Technologies, Irvine, Calif., USA). Around 0.5 nl of a prepared PCR product was spotted at each location to produce spots with approximately 100 um diameters. Spot center-to-center spacing was from 180 um to 210 um depending on the array. Printing was conducted in a chamber with relative humidity set at 50%.

Slides containing maize sequences were purchased from Agilent Technology (Palo Alto, Calif. 94304).

Post-Processing of Slides

After arraying, slides were processed through a series of steps—rehydration, UV cross-linking, blocking and denaturation—required prior to hybridization. Slides were rehydrated by placing them over a beaker of warm water (DNA face down), for 2-3 sec, to distribute the DNA more evenly within the spots, and then snap dried on a hot plate (DNA side, face up). The DNA was then cross-linked to the slides by UV irradiation (60-65 mJ; 2400 Stratalinker, Stratagene, La Jolla, Calif., USA).

Following this a blocking step was performed to modify remaining free lysine groups, and hence minimize their ability to bind labeled probe DNA. To achieve this the arrays were placed in a slide rack. An empty slide chamber was left ready on an orbital shaker. The rack was bent slightly inwards in the middle, to ensure the slides would not run into each other while shaking. The blocking solution was prepared as follows:

3×350-ml glass chambers (with metal tops) were set to one side, and a large round Pyrex dish with dH$_2$O was placed ready in the microwave. At this time, 15 ml sodium borate was prepared in a 50 ml conical tube.

6-g succinic anhydride was dissolved in approx. 325-350 mL 1-methyl-2-pyrrolidinone. Rapid addition of reagent was crucial.

a. Immediately after the last flake of the succinic anhydride dissolved, the 15-mL sodium borate was added.

b. Immediately after the sodium borate solution mixed in, the solution was poured into an empty slide chamber.

c. The slide rack was plunged rapidly and evenly in the solution. It was vigorously shaken up and down for a few seconds, making sure slides never left the solution.

d. It was mixed on an orbital shaker for 15-20 min. Meanwhile, the water in the Pyrex dish (enough to cover slide rack) was heated to boiling.

Following this, the slide rack was gently plunge in the 95 C water (just stopped boiling) for 2 min. Then the slide rack was plunged 5× in 95% ethanol. The slides and rack were centrifuged for 5 min. @ 500 rpm. The slides were loaded quickly and evenly onto the carriers to avoid streaking. The arrays were used immediately or store in slide box.

The Hybridization process began with the isolation of mRNA from the two tissues (see "Isolation of total RNA" and "Isolation of mRNA", below) in question followed by their conversion to single stranded cDNA (see "Generation of probes for hybridization", below). The cDNA from each tissue was independently labeled with a different fluorescent dye and then both samples were pooled together. This final differentially labeled cDNA pool was then placed on a processed microarray and allowed to hybridize (see "Hybridization and wash conditions", below).

Isolation of Total RNA

Approximately 1 g of plant tissue was ground in liquid nitrogen to a fine powder and transferred into a 50-ml centrifuge tube containing 10 ml of Trizol reagent. The tube was vigorously vortexed for 1 min and then incubated at room temperature for 10-20 min. on an orbital shaker at 220 rpm. Two ml of chloroform was added to the tube and the solution vortexed vigorously for at least 30-sec before again incubating at room temperature with shaking. The sample was then centrifuged at 12,000×g (10,000 rpm) for 15-20 min at 4° C. The aqueous layer was removed and mixed by inversion with 2.5 ml of 1.2 M NaCl/0.8 M Sodium Citrate and 2.5 ml of isopropyl alcohol added. After a 10 min. incubation at room temperature, the sample was centrifuged at 12,000×g (10,000 rpm) for 15 min at 4° C. The pellet washed with 70% ethanol, re-centrifuged at 8,000 rpm for 5 min and then air dried at room temperature for 10 min. The resulting total RNA was dissolved in either TE (10 mM Tris-HCl, 1 mM EDTA, pH 8.0) or DEPC (diethylpyrocarbonate) treated deionized water (RNAse-free water). For subsequent isolation of mRNA using the Qiagen kit, the total RNA pellet was dissolved in RNAse-free water.

Isolation of mRNA mRNA was isolated using the Qiagen Oligotex mRNA Spin-Column protocol (Qiagen, Valencia, Calif.). Briefly, 500 μl OBB buffer (20 mM Tris-Cl, pH 7.5, 1 M NaCl, 2 mM EDTA, 0.2% SDS) was added to 500 μl of total RNA (0.5-0.75 mg) and mixed thoroughly. The sample was first incubated at 70° C. for 3 min, then at room temperature for 10 minutes and finally centrifuged for 2 min at 14,000-18,000×g. The pellet was resuspended in 400 μl OW2 buffer (10 mM Tris-Cl, pH 7.5, 150 mM NaCl, 1 mM EDTA) by vortexing, the resulting solution placed on a small spin column in a 1.5 ml RNase-free microcentrifuge tube and centrifuged for 1 min at 14,000-18,000×g. The spin column was transferred to a new 1.5 ml RNase-free microcentrifuge tube and washed with 400 μl of OW2 buffer. To release the isolated mRNA from the resin, the spin column was again transferred to a new RNase-free 1.5 ml microcentrifuge tube, 20-100 μl 70° C. OEB buffer (5 mM Tris-Cl, pH 7.5) added and the resin resuspended in the resulting solution via pipetting. The mRNA solution was collected after centrifuging for 1 min at 14,000-18,000×g.

Alternatively, mRNA was isolated using the Stratagene Poly(A) Quik mRNA Isolation Kit (Stratagene, La Jolla, Calif.). Here, up to 0.5 mg of total RNA (maximum volume of 1 ml) was incubated at 65° C. for 5 minutes, snap cooled on ice and 0.1× volumes of 10× sample buffer (10 mM Tris-HCl (pH 7.5), 1 mM EDTA (pH 8.0) 5 M NaCl) added. The RNA sample was applied to a prepared push column and passed through the column at a rate of ~1 drop every 2 sec. The solution collected was reapplied to the column and collected as above. 200 μl of high salt buffer (10 mM Tris-HCl (pH 7.5), 1 mM EDTA, 0.5 NaCl) was applied to the column and passed through the column at a rate of ~1 drop every 2 sec. This step was repeated and followed by three low salt buffer (10 mM Tris-HCl (pH 7.5), 1 mM EDTA, 0.1 M NaCl) washes preformed in a similar manner. mRNA was eluted by applying to the column four separate 200 μl aliquots of elution buffer (10 mM Tris-HCl (pH 7.5), 1 mM EDTA) preheated to 65° C. Here, the elution buffer was passed through the column at a rate of 1 drop/sec. The resulting mRNA solution was precipitated by adding 0.1× volumes of 10× sample buffer, 2.5 volumes of ice-cold 100% ethanol, incubating overnight at −20° C. and centrifuging at 14,000-18,000×g for 20-30 min at 4° C. The pellet washed with 70% ethanol and air dried for 10 min. at room temperature before resuspension in RNase-free deionized water.

Preparation of Yeast Controls

Plasmid DNA was isolated from the following yeast clones using Qiagen filtered maxiprep kits (Qiagen, Valencia, Calif.): YAL022c(Fun26), YAL031c(Fun21), YBR032w, YDL131w, YDL182w, YDL194w, YDL196w, YDR050c and YDR116c. Plasmid DNA was linearized with either BsrBI (YAL022c(Fun26), YAL031c(Fun21), YDL131w, YDL182w, YDL194w, YDL196w, YDR050c) or AflIII (YBR032w, YDR116c) and isolated.

In Vitro Transcription of Yeast Clones

The following solution was incubated at 37° C. for 2 hours: 17 μl of isolated yeast insert DNA (1 μg), 20 μl 5× buffer, 10 μl 100 mM DTT, 2.5 μl (100 U) RNasin, 20 μl 2.5 mM (ea.) rNTPs, 2.7 μl (40 U) SP6 polymerase and 27.8 μl RNase-free deionized water. 2 μl (2 U) Ampli DNase I was added and the incubation continued for another 15 min. 10 μl 5M NH$_4$OAC and 100 μl phenol:chloroform:isoamyl alcohol (25:24:1) were added, the solution vortexed and then centrifuged to separate the phases. To precipitate the RNA, 250 μl ethanol was added and the solution incubated at −20° C. for at least one hour. The sample was then centrifuged for 20 min at 4° C. at 14,000-18,000×g, the pellet washed with 500 μl of 70% ethanol, air dried at room temperature for 10 min and resuspended in 100 μl of RNase-free deionized water. The precipitation procedure was then repeated.

Alternatively, after the two-hour incubation, the solution was extracted with phenol/chloroform once before adding 0.1 volume 3M sodium acetate and 2.5 volumes of 100% ethanol. The solution was centrifuged at 15,000 rpm, 4° C. for 20 minutes and the pellet resuspended in RNase-free deionized water. The DNase I treatment was carried out at 37° C. for 30 minutes using 2 U of Ampli DNase I in the following reaction condition: 50 mM Tris-HCl (pH 7.5), 10 mM MgCl$_2$. The DNase I reaction was then stopped with the addition of NH$_4$OAC and phenol:chloroform:isoamyl alcohol (25:24:1), and RNA isolated as described above.

0.15-2.5 ng of the in vitro transcript RNA from each yeast clone were added to each plant mRNA sample prior to labeling to serve as positive (internal) probe controls.

Generation of Probes for Hybridization

Generation of Labeled Probes for Hybridization from First-strand cDNA

Hybridization probes were generated from isolated mRNA using an Atlas™ Glass Fluorescent Labeling Kit (Clontech Laboratories, Inc., Palo Alto, Calif., USA). This entails a two step labeling procedure that first incorporates primary aliphatic amino groups during cDNA synthesis and then couples fluorescent dye to the cDNA by reaction with the amino functional groups. Briefly, 5 µg of oligo(dT)$_{18}$ primer d(TTTTTTTTTTTTTTTTTTV)(SEQ ID NO: 50) was mixed with Poly A+mRNA (1.5-2 µg mRNA isolated using the Qiagen Oligotex mRNA Spin-Column protocol or-the Stratagene Poly(A) Quik mRNA Isolation protocol (Stratagene, La Jolla, Calif., USA)) in a total volume of 25 µl. The sample was incubated in a thermocycler at 70° C. for 5 min, cooled to 48° C. and 10 µl of 5x cDNA Synthesis Buffer (kit supplied), 5 l 10x dNTP mix (dATP, dCTP, dGTP, dTTP and aminoallyl-dUTP; kit supplied), 7.5 µl deionized water and 2.5 µl MMLV Reverse Transcriptase (500U) added. The reaction was then incubated at 48° C. for 30 minutes, followed by 1 hr incubation at 42° C. At the end of the incubation the reaction was heated to 70° C. for 10 min, cooled to 37° C. and 0.5 µl (5 U) RNase H added, before incubating for 15 min at 37° C. The solution was vortexed for 1 min after the addition of 0.5 µl 0.5 M EDTA and 5 µl of QuickClean Resin (kit supplied) then centrifuged at 14,000-18,000× g for 1 min. After removing the supernatant to a 0.45 µm spin filter (kit supplied), the sample was again centrifuged at 14,000-18,000× g for 1 min, and 5.5 µl 3 M sodium acetate and 137.5 µl of 100% ethanol added to the sample before incubating at −20° C. for at least 1 hr. The sample was then centrifuged at 14,000-18,000× g at 4° C. for 20 min, the resulting pellet washed with 500 µl 70% ethanol, air-dried at room temperature for 10 min and resuspended in 10 µl of 2× fluorescent labeling buffer (kit provided). 10 µl each of the fluorescent dyes Cy3 and Cy5 (Amersham Pharmacia (Piscataway, N.J., USA); prepared according to Atlas™ kit directions of Clontech) were added and the sample incubated in the dark at room temperature for 30 min.

The fluorescently labeled first strand cDNA was precipitated by adding 2 µl 3M sodium acetate and 50 µl 100% ethanol, incubated at −20° C. for at least 2 hrs, centrifuged at 14,000-18,000×g for 20 min, washed with 70% ethanol, air-dried for 10 min and dissolved in 100 µl of water.

Alternatively, 3-4 µg mRNA, 2.5 (~8.9 ng of in vitro translated mRNA) µl yeast control and 3 µg oligo dTV (TTTTTTTTTTTTTTTTTTT(A/C/G)(SEQ ID NO: 50) were mixed in a total volume of 24.7 µl. The sample was incubated in a thermocycler at 70° C. for 10 min. before chilling on ice. To this, 8 µl of 5× first strand buffer (SuperScript II RNase H-Reverse Transcriptase kit from Invitrogen (Carlsbad, Calif. 92008); cat no. 18064022), 0.8° C. of aa-dUTP/dNTP mix (50×; 25 mM dATP, 25 mM dGTP, 25 mM dCTP, 15 mM dTTP, 10 mM aminoallyl-dUTP), 4 µl of 0.1 M DTT and 2.5 µl (500 units) of Superscript R.T.II enzyme (Stratagene) were added. The sample was incubated at 42° C. for 2 hours before a mixture of 10° C. of 1M NaOH and 10° C. of 0.5 M EDTA were added. After a 15 minute incubation at 65° C., 25 µl of 1 M Tris pH 7.4 was added. This was mixed with 450 µl of water in a Microcon 30 column before centrifugation at 11,000×g for 12 min. The column washed twice with 450 µl (centrifugation at 11,000 g, 12 min.) before eluting the sample by inverting the Microcon column and centrifuging at 11,000×g for 20 seconds. Sample was dehydrated by centrifugation under vacuum and stored at −20° C.

Each reaction pellet was dissolved in 9 µl of 0.1 M carbonate buffer (0.1M sodium carbonate and sodium bicarbonate, pH=8.5-9) and 4.5 µl of this placed in two microfuge tubes. 4.5 µl of each dye (in DMSO) were added and the mixture incubated in the dark for 1 hour. 4.5 µl of 4 M hydroxylamine was added and again incubated in the dark for 15 minutes.

Regardless of the method used for probe generation, the probe was purified using a Qiagen PCR cleanup kit (Qiagen, Valencia, Calif., USA), and eluted with 100 ul EB (kit provided). The sample was loaded on a Microcon YM-30 (Millipore, Bedford, Mass., USA) spin column and concentrated to 4-5 ul in volume.

Probes for the maize microarrays were generated using the Fluorescent Linear Amplification Kit (cat. No. G2556A) from Agilent Technologies (Palo Alto, Calif.).

Hybridization and Wash Conditions

The following Hybridization and Washing Condition were developed:

Hybridization Conditions:

Labeled probe was heated at 95° C. for 3 min and chilled on ice. Then 25 □L of the hybridization buffer which was warmed at 42 C was added to the probe, mixing by pipetting, to give a final concentration of:

50% formamide
4×SSC
0.03% SDS
5× Denhardt's solution
0.1 µg/ml single-stranded salmon sperm DNA The probe was kept at 42 C. Prior to the hybridization, the probe was heated for 1 more min., added to the array, and then covered with a glass cover slip. Slides were placed in hybridization chambers (Telechem, Sunnyvale, Calif.) and incubated at 42° C. overnight.

Washing Conditions:

A. Slides were washed in 1×SSC+0.03% SDS solution at room temperature for 5 minutes,
B. Slides were washed in 0.2×SSC at room temperature for 5 minutes,
C. Slides were washed in 0.05×SSC at room temperature for 5 minutes.

After A, B, and C, slides were spun at 800×g for 2 min. to dry. They were then scanned.

Maize microarrays were hybridized according to the instructions included Fluorescent Linear Amplification Kit (cat. No. G2556A) from Agilent Technologies (Palo Alto, Calif.).

Scanning of Slides

The chips were scanned using a ScanArray 3000 or 5000 (General Scanning, Watertown, Mass., USA). The chips were scanned at 543 and 633 nm, at 10 um resolution to measure the intensity of the two fluorescent dyes incorporated into the samples hybridized to the chips.

Data Extraction and Analysis

The images generated by scanning slides consisted of two 16-bit TIFF images representing the fluorescent emissions of the two samples at each arrayed spot. These images were then quantified and processed for expression analysis using the data extraction software Imagene™ (Biodiscovery, Los Angeles, Calif., USA). Imagene output was subsequently analyzed using the analysis program Genespring™ (Silicon Genetics, San Carlos, Calif., USA). In Genespring, the data was imported using median pixel intensity measurements derived from Imagene output. Background subtraction, ratio calculation and normalization were all conducted in Genespring. Normalization was achieved by breaking the data in to 32 groups, each of which represented one of the 32 pin printing regions on the microarray. Groups consist of 360 to 550 spots. Each group was independently normalized by setting the median of ratios to one and multiplying ratios by the appropriate factor.

Results

The MA_diff Table (TABLE 10) presents the results of the differential expression experiments for the mRNAs, as reported by their corresponding cDNA ID number, that were differentially transcribed under a particular set of conditions as compared to a control sample. The cDNA ID numbers correspond to those utilized in the Reference and Sequence Tables. Increases in mRNA abundance levels in experimental plants versus the controls are denoted with the plus sign (+). Likewise, reductions in mRNA abundance levels in the experimental plants are denoted with the minus (−) sign.

The Table is organized according to the clone number with each set of experimental conditions being denoted by the term "Expt Rep ID:" followed by a "short name". Table 9 links each Expt Rep ID with a short description of the experiment and the parameters. The experiment numbers are referenced in the appropriate utility/functions sections herein.

The sequences showing differential expression in a particular experiment (denoted by either a "+" or "−" in the Table) thereby shows utility for a function in a plant, and these functions/utilities are described in detail below, where the title of each section (i.e. a "utility section") is correlated with the particular differential expression experiment in TABLE 9.

Organ-Affecting Genes, Gene Components, Products (Including Differentiation and Function)

Root Genes

The economic values of roots arise not only from harvested adventitious roots or tubers, but also from the ability of roots to funnel nutrients to support growth of all plants and increase their vegetative material, seeds, fruits, etc. Roots have four main functions. First, they anchor the plant in the soil. Second, they facilitate and regulate the molecular signals and molecular traffic between the plant, soil, and soil fauna. Third, the root provides a plant with nutrients gained from the soil or growth medium. Fourth, they condition local soil chemical and physical properties.

Root genes are active or potentially active to a greater extent in roots than in most other organs of the plant. These genes and gene products can regulate many plant traits from yield to stress tolerance. Root genes can be used to modulate root growth and development.

Differential Expression of the Sequences in Roots

The relative levels of mRNA product in the root versus the aerial portion of the plant was measured. Specifically, mRNA was isolated from roots and root tips of *Arabidopsis* plants and compared to mRNA isolated from the aerial portion of the plants utilizing microarray procedures. Results are presented in TABLE 10.

Reproduction Genes, Gene Components and Products

Reproduction genes are defined as genes or components of genes capable of modulating any aspect of sexual reproduction from flowering time and inflorescence development to fertilization and finally seed and fruit development. These genes are of great economic interest as well as biological importance. The fruit and vegetable industry grosses over $1 billion USD a year. The seed market, valued at approximately $15 billion USD annually, is even more lucrative.

Inflorescence and Floral Development Genes, Gene Components and Products

During reproductive growth the plant enters a program of floral development that culminates in fertilization, followed by the production of seeds. Senescence may or may not follow. The flower formation is a precondition for the sexual propagation of plants and is therefore essential for the propagation of plants that cannot be propagated vegetatively as well as for the formation of seeds and fruits. The point of time at which the merely vegetative growth of plants changes into flower formation is of vital importance for example in agriculture, horticulture and plant breeding. Also the number of flowers is often of economic importance, for example in the case of various useful plants (tomato, cucumber, zucchini, cotton etc.) with which an increased number of flowers may lead to an increased yield, or in the case of growing ornamental plants and cut flowers.

Flowering plants exhibit one of two types of inflorescence architecture: indeterminate, in which the inflorescence grows indefinitely, or determinate, in which a terminal flower is produced. Adult organs of flowering plants develop from groups of stem cells called meristems. The identity of a meristem is inferred from structures it produces: vegetative meristems give rise to roots and leaves, inflorescence meristems give rise to flower meristems, and flower meristems give rise to floral organs such as sepals and petals. Not only are meristems capable of generating new meristems of different identity, but their own identity can change during development. For example, a vegetative shoot meristem can be transformed into an inflorescence meristem upon floral induction, and in some species, the inflorescence meristem itself will eventually become a flower meristem. Despite the importance of meristem transitions in plant development, little is known about the underlying mechanisms.

Following germination, the shoot meristem produces a series of leaf meristems on its flanks. However, once floral induction has occurred, the shoot meristem switches to the production of flower meristems. Flower meristems produce floral organ primordia, which develop individually into sepals, petals, stamens or carpels. Thus, flower formation can be thought of as a series of distinct developmental steps, i.e. floral induction, the formation of flower primordia and the production of flower organs. Mutations disrupting each of the steps have been isolated in a variety of species, suggesting that a genetic hierarchy directs the flowering process (see for review, Weigel and Meyerowitz, In Molecular Basis of Morphogenesis (ed. M. Bernfield). 51st Annual Symposium of the Society for Developmental Biology, pp. 93-107, New York, 1993).

Expression of many reproduction genes and gene products is orchestrated by internal programs or the surrounding environment of a plant. These genes can be used to modulate traits such as fruit and seed yield Seed and Fruit Development Genes, Gene Components and Products The ovule is the primary female sexual reproductive organ of flowering plants. At maturity it contains the egg cell and one large central cell containing two polar nuclei encased by two integuments that, after fertilization, develops into the embryo, endosperm, and seed coat of the mature seed, respectively. As the ovule develops development requires the orchestrated transcription of numerous polynucleotides, some of which are ubiquitous, others that are embryo-specific and still others that are expressed only in the endosperm, seed coat, or fruit. Such genes are termed fruit development responsive genes and can be used to modulate seed and fruit growth and development such as seed size, seed yield, seed composition and seed dormancy.

Differential Expression of the Sequences in Siliques, Inflorescences and Flowers The relative levels of mRNA product in the siliques relative to the plant as a whole was measured. The results are presented in TABLE 10.

Differential Expression of the Sequences in Hybrid Seed Development

The levels of mRNA product in the seeds relative to those in a leaf and floral stems was measured. The results are presented TABLE 10.

Development Genes, Gene Components and Products

Imbibition and Germination Responsive Genes Gene Components and Products

Seeds are a vital component of the world's diet. Cereal grains alone, which comprise ~90% of all cultivated seeds, contribute up to half of the global per capita energy intake. The primary organ system for seed production in flowering plants is the ovule. At maturity, the ovule consists of a haploid female gametophyte or embryo sac surrounded by several layers of maternal tissue including the nucleus and the integuments. The embryo sac typically contains seven cells including the egg cell, two synergids, a large central cell containing two polar nuclei, and three antipodal cells. That pollination results in the fertilization of both egg and central cell. The fertilized egg develops into the embryo. The fertilized central cell develops into the endosperm. And the integuments mature into the seed coat. As the ovule develops into the seed, the ovary matures into the fruit or silique. Late in development, the developing seed ends a period of extensive biosynthetic and cellular activity and begins to desiccate to complete its development and enter a dormant, metabolically quiescent state. Seed dormancy is generally an undesirable characteristic in agricultural crops, where rapid germination and growth are required. However, some degree of dormancy is advantageous, at least during seed development. This is particularly true for cereal crops because it prevents germination of grains while still on the ear of the parent plant (preharvest sprouting), a phenomenon that results in major losses to the agricultural industry. Extensive domestication and breeding of crop species have ostensibly reduced the level of dormancy mechanisms present in the seeds of their wild ancestors, although under some adverse environmental conditions, dormancy may reappear. By contrast, weed seeds frequently mature with inherent dormancy mechanisms that allow some seeds to persist in the soil for many years before completing germination.

Germination commences with imbibition, the uptake of water by the dry seed, and the activation of the quiescent embryo and endosperm. The result is a burst of intense metabolic activity. At the cellular level, the genome is transformed from an inactive state to one of intense transcriptional activity. Stored lipids, carbohydrates and proteins are catabolized fueling seedling growth and development. DNA and organelles are repaired, replicated and begin functioning. Cell expansion and cell division are triggered. The shoot and root apical meristem are activated and begin growth and organogenesis. Schematic 4 summarizes some of the metabolic and cellular processes that occur during imbibition. Germination is complete when a part of the embryo, the radicle, extends to penetrate the structures that surround it. In Arabidopsis, seed germination takes place within twenty-four (24) hours after imbibition. As such, germination requires the rapid and orchestrated transcription of numerous polynucleotides. Germination is followed by expansion of the hypocotyl and opening of the cotyledons. Meristem development continues to promote root growth and shoot growth, which is followed by early leaf formation.

Imbibition and Germination Genes

Imbibition and germination includes those events that commence with the uptake of water by the quiescent dry seed and terminate with the expansion and elongation of the shoots and roots. The germination period exists from imbibition to when part of the embryo, usually the radicle, extends to penetrate the seed coat that surrounds it. Imbibition and germination genes are defined as genes, gene components and products capable of modulating one or more processes of imbibition and germination described above. They are useful to modulate many plant traits from early vigor to yield to stress tolerance.

Differential Expression of the Sequences in Germinating Seeds and Imbibed Embryos The levels of mRNA product in the seeds versus the plant as a whole was measured. The results are presented in TABLE 10.

Hormone Responsive Genes, Gene Components and Products

Abscissic Acid Responsive Genes, Gene Components and Products

Plant hormones are naturally occurring substances, effective in very small amounts, which act as signals to stimulate or inhibit growth or regulate developmental processes in plants. Abscisic acid (ABA) is a ubiquitous hormone in vascular plants that has been detected in every major organ or living tissue from the root to the apical bud. The major physiological responses affected by ABA are dormancy, stress stomatal closure, water uptake, abscission and senescence. In contrast to Auxins, cytokinins and gibberellins, which are principally growth promoters, ABA primarily acts as an inhibitor of growth and metabolic processes.

Changes in ABA concentration internally or in the surrounding environment in contact with a plant results in modulation of many genes and gene products. These genes and/or products are responsible for effects on traits such as plant vigor and seed yield.

While ABA responsive polynucleotides and gene products can act alone, combinations of these polynucleotides also affect growth and development. Useful combinations include different ABA responsive polynucleotides and/or gene products that have similar transcription profiles or similar biological activities, and members of the same or similar biochemical pathways. Whole pathways or segments of pathways are controlled by transcription factor proteins and proteins controlling the activity of signal transduction pathways. Therefore, manipulation of such protein levels is especially useful for altering phenotypes and biochemical activities of plants. In addition, the combination of an ABA responsive polynucleotide and/or gene product with another environmentally responsive polynucleotide is also useful because of the interactions that exist between hormone-regulated pathways, stress and defense induced pathways, nutritional pathways and development.

Differential Expression of the Sequences in ABA Treated Plants

The relative levels of mRNA product in plants treated with ABA versus controls treated with water were measured. Results are presented in TABLE 10.

Brassinosteroid Responsive Genes, Gene Components and Products

Plant hormones are naturally occurring substances, effective in very small amounts, which act as signals to stimulate or inhibit growth or regulate developmental processes in plants. Brassinosteroids (BRs) are the most recently discovered, and least studied, class of plant hormones. The major physiological response affected by BRs is the longitudinal growth of young tissue via cell elongation and possibly cell division. Consequently, disruptions in BR metabolism, perception and activity frequently result in a dwarf phenotype. In addition, because BRs are derived from the sterol metabolic pathway, any perturbations to the sterol pathway can affect the BR pathway. In the same way, perturbations in the BR pathway can have effects on the later part of the sterol pathway and thus the sterol composition of membranes.

Changes in BR concentration in the surrounding environment or in contact with a plant result in modulation of many genes and gene products. These genes and/or products are responsible for effects on traits such as plant biomass and seed yield. These genes were discovered and characterized from a much larger set of genes by experiments designed to find genes whose mRNA abundance changed in response to application of BRs to plants.

While BR responsive polynucleotides and gene products can act alone, combinations of these polynucleotides also affect growth and development. Useful combinations include different BR responsive polynucleotides and/or gene products that have similar transcription profiles or similar biological activities, and members of the same or functionally related biochemical pathways. Whole pathways or segments of pathways are controlled by transcription factors and proteins controlling the activity of signal transduction pathways. Therefore, manipulation of such protein levels is especially useful for altering phenotypes and biochemical activities of plants. In addition, the combination of a BR responsive polynucleotide and/or gene product with another environmentally responsive polynucleotide is useful because of the interactions that exist between hormone-regulated pathways, stress pathways, nutritional pathways and development. Here, in addition to polynucleotides having similar transcription profiles and/or biological activities, useful combinations include polynucleotides that may have different transcription profiles but which participate in common or overlapping pathways.

Differential Expression of the Sequences in Epi-brassinolide or Brassinozole Plants The relative levels of mRNA product in plants treated with either epi-brassinolide or brassinozole were measured. Results are presented in TABLE 10.

Metabolism Affecting Genes, Gene Components and Products

Nitrogen Responsive Genes, Gene Components and Products

Nitrogen is often the rate-limiting element in plant growth, and all field crops have a fundamental dependence on exogenous nitrogen sources. Nitrogenous fertilizer, which is usually supplied as ammonium nitrate, potassium nitrate, or urea, typically accounts for 40% of the costs associated with crops, such as corn and wheat in intensive agriculture. Increased efficiency of nitrogen use by plants should enable the production of higher yields with existing fertilizer inputs and/or enable existing yields of crops to be obtained with lower fertilizer input, or better yields on soils of poorer quality. Also, higher amounts of proteins in the crops could also be produced more cost-effectively. "Nitrogen responsive" genes and gene products can be used to alter or modulate plant growth and development.

Differential Expression of the Sequences in Whole Seedlings, Shoots and Roots

The relative levels of mRNA product in whole seedlings, shoots and roots treated with either high or low nitrogen media were compared to controls. Results are presented in TABLE 10.

Viability Genes, Gene Components and Products

Plants contain many proteins and pathways that when blocked or induced lead to cell, organ or whole plant death. Gene variants that influence these pathways can have profound effects on plant survival, vigor and performance. The critical pathways include those concerned with metabolism and development or protection against stresses, diseases and pests. They also include those involved in apoptosis and necrosis. Viability genes can be modulated to affect cell or plant death. Herbicides are, by definition, chemicals that cause death of tissues, organs and whole plants. The genes and pathways that are activated or inactivated by herbicides include those that cause cell death as well as those that function to provide protection.

Differential Expression of the Sequences in Herbicide Treated Plants and Herbicide Resistant Mutants The relative levels of mRNA product in plants treated with herbicide and mutants resistant to herbicides were compared to control plants. Results are presented in TABLE 10.

Stress Responsive Genes, Gene Components and Products

Cold Responsive Genes, Gene Components and Products

The ability to endure low temperatures and freezing is a major determinant of the geographical distribution and productivity of agricultural crops. Even in areas considered suitable for the cultivation of a given species or cultivar, can give rise to yield decreases and crop failures as a result of aberrant, freezing temperatures. Even modest increases (1-2° C.) in the freezing tolerance of certain crop species would have a dramatic impact on agricultural productivity in some areas. The development of genotypes with increased freezing tolerance would provide a more reliable means to minimize crop losses and diminish the use of energy-costly practices to modify the microclimate.

Sudden cold temperatures result in modulation of many genes and gene products, including promoters. These genes and/or products are responsible for effects on traits such as plant vigor and seed yield.

Manipulation of one or more cold responsive gene activities is useful to modulate growth and development.

Differential Expression of the Sequences in Cold Treated Plants

The relative levels of mRNA product in cold treated plants were compared to control plants. Results are presented in TABLE 10.

Heat Responsive Genes, Gene Components and Products

The ability to endure high temperatures is a major determinant of the geographical distribution and productivity of agricultural crops. Decreases in yield and crop failure frequently occur as a result of aberrant, hot conditions even in areas considered suitable for the cultivation of a given species or cultivar. Only modest increases in the heat tolerance of crop species would have a dramatic impact on agricultural productivity. The development of genotypes with increased heat tolerance would provide a more reliable means to minimize crop losses and diminish the use of energy-costly practices to modify the microclimate.

Changes in temperature in the surrounding environment or in a plant microclimate results in modulation of many genes and gene products.

Differential Expression of the Sequences in Heat Treated Plants

The relative levels of mRNA product in heat treated plants were compared to control plants. Results are presented in TABLE 10.

Drought Responsive Genes, Gene Components and Products

The ability to endure drought conditions is a major determinant of the geographical distribution and productivity of agricultural crops. Decreases in yield and crop failure frequently occur as a result of aberrant, drought conditions even in areas considered suitable for the cultivation of a given species or cultivar. Only modest increases in the drought tolerance of crop species would have a dramatic impact on agricultural productivity. The development of genotypes with increased drought tolerance would provide a more reliable means to minimize crop losses and diminish the use of energy-costly practices to modify the microclimate.

Drought conditions in the surrounding environment or within a plant, results in modulation of many genes and gene products.

Differential Expression of the Sequences in Drought Treated Plants and Drought Mutants The relative levels of mRNA product in drought treated plants and drought mutants were compared to control plants. Results are presented in TABLE 10.

Methyl Jasmonate (Jasmonate) Responsive Genes, Gene Components and Products

Jasmonic acid and its derivatives, collectively referred to as jasmonates, are naturally occurring derivatives of plant lipids. These substances are synthesized from linolenic acid in a lipoxygenase-dependent biosynthetic pathway. Jasmonates are signalling molecules which have been shown to be growth regulators as well as regulators of defense and stress responses. As such, jasmonates represent a separate class of plant hormones. Jasmonate responsive genes can be used to modulate plant growth and development.

Differential Expression of the Sequences in Methyl Jasmonate Treated Plants

The relative levels of mRNA product in methyl jasmonate treated plants were compared to control plants. Results are presented in TABLE 10.

Salicylic Acid Responsive Genes, Gene Components and Products

Plant defense responses can be divided into two groups: constitutive and induced. Salicylic acid (SA) is a signaling molecule necessary for activation of the plant induced defense system known as systemic acquired resistance or SAR. This response, which is triggered by prior exposure to avirulent pathogens, is long lasting and provides protection against a broad spectrum of pathogens. Another induced defense system is the hypersensitive response (HR). HR is far more rapid, occurs at the sites of pathogen (avirulent pathogens) entry and precedes SAR. SA is also the key signaling molecule for this defense pathway.

Differential Expression of the Sequences in Salicylic Acid Treated Plants

The relative levels of mRNA product in salicylic acid treated plants were compared to control plants. Results are presented in TABLE 10.

Osmotic Stress Responsive Genes, Gene Components and Products

The ability to endure and recover from osmotic and salt related stress is a major determinant of the geographical distribution and productivity of agricultural crops. Osmotic stress is a major component of stress imposed by saline soil and water deficit. Decreases in yield and crop failure frequently occur as a result of aberrant or transient environmental stress conditions even in areas considered suitable for the cultivation of a given species or cultivar. Only modest increases in the osmotic and salt tolerance of a crop species would have a dramatic impact on agricultural productivity. The development of genotypes with increased osmotic tolerance would provide a more reliable means to minimize crop losses and diminish the use of energy-costly practices to modify the soil environment. Thus, osmotic stress responsive genes can be used to modulate plant growth and development.

Differential Expression of the Sequences in PEG Treated Plants

The relative levels of mRNA product in PEG treated plants were compared to control plants. Results are presented in TABLE 10.

Shade Responsive Genes, Gene Components and Products

Plants sense the ratio of Red (R):Far Red (FR) light in their environment and respond differently to particular ratios. A low R:FR ratio, for example, enhances cell elongation and favors flowering over leaf production. The changes in R:FR ratios mimic and cause the shading response effects in plants. The response of a plant to shade in the canopy structures of agricultural crop fields influences crop yields significantly. Therefore manipulation of genes regulating the shade avoidance responses can improve crop yields. While phytochromes mediate the shade avoidance response, the down-stream factors participating in this pathway are largely unknown. One potential downstream participant, ATHB-2, is a member of the HD-Zip class of transcription factors and shows a strong and rapid response to changes in the R:FR ratio. ATHB-2 overexpressors have a thinner root mass, smaller and fewer leaves and longer hypocotyls and petioles. This elongation arises from longer epidermal and cortical cells, and a decrease in secondary vascular tissues, paralleling the changes observed in wild-type seedlings grown under conditions simulating canopy shade. On the other hand, plants with reduced ATHB-2 expression have a thick root mass and many larger leaves and shorter hypocotyls and petioles. Here, the changes in the hypocotyl result from shorter epidermal and cortical cells and increased proliferation of vascular tissue. Interestingly, application of Auxin is able to reverse the root phenotypic consequences of high ATHB-2 levels, restoring the wild-type phenotype. Consequently, given that ATHB-2 is tightly regulated by phytochrome, these data suggest that ATHB-2 may link the Auxin and phytochrome pathways in the shade avoidance response pathway.

Shade responsive genes can be used to modulate plant growth and development.

Differential Expression of the Sequences in Far-Red Light Treated Plants

The relative levels of mRNA product in far-red light treated plants were compared to control plants. Results are presented in TABLE 10.

Viability Genes, Gene Components and Products

Plants contain many proteins and pathways that when blocked or induced lead to cell, organ or whole plant death. Gene variants that influence these pathways can have profound effects on plant survival, vigor and performance. The critical pathways include those concerned with metabolism and development or protection against stresses, diseases and pests. They also include those involved in apoptosis and necrosis. The applicants have elucidated many such genes and pathways by discovering genes that when inactivated lead to cell or plant death.

Herbicides are, by definition, chemicals that cause death of tissues, organs and whole plants. The genes and pathways that are activated or inactivated by herbicides include those that cause cell death as well as those that function to provide protection. The applicants have elucidated these genes.

The genes defined in this section have many uses including manipulating which cells, tissues and organs are selectively killed, which are protected, making plants resistant to herbicides, discovering new herbicides and making plants resistant to various stresses.

Viability genes were also identified from a much larger set of genes by experiments designed to find genes whose mRNA products changed in concentration in response to applications of different herbicides to plants. Viability genes are characteristically differentially transcribed in response to fluctuating herbicide levels or concentrations, whether internal or external to an organism or cell. The MA_diff Table reports the changes in transcript levels of various viability genes.

Early Seedling-Phase Specific Responsive Genes, Gene Components and Products

One of the more active stages of the plant life cycle is a few days after germination is complete, also referred to as the early seedling phase. During this period the plant begins development and growth of the first leaves, roots, and other organs not found in the embryo. Generally this stage begins when germination ends. The first sign that germination has been completed is usually that there is an increase in length and fresh weight of the radicle. Such genes and gene products can regulate a number of plant traits to modulate yield. For example, these genes are active or potentially active to a greater extent in developing and rapidly growing cells, tissues and organs, as exemplified by development and growth of a seedling 3 or 4 days after planting a seed.

Rapid, efficient establishment of a seedling is very important in commercial agriculture and horticulture. It is also vital that resources are approximately partitioned between shoot and root to facilitate adaptive growth. Phototropism and geotropism need to be established. All these require post-germination process to be sustained to ensure that vigorous seedlings are produced. Early seedling phase genes, gene components and products are useful to manipulate these and other processes.

Guard Cell Genes, Gene Components and Products

Scattered throughout the epidermis of the shoot are minute pores called stomata. Each stomal pore is surrounded by two guard cells. The guard cells control the size of the stomal pore, which is critical since the stomata control the exchange of carbon dioxide, oxygen, and water vapor between the interior of the plant and the outside atmosphere. Stomata open and close through turgor changes driven by ion fluxes, which occur mainly through the guard cell plasma membrane and tonoplast. Guard cells are known to respond to a number of external stimuli such as changes in light intensity, carbon dioxide and water vapor, for example. Guard cells can also sense and rapidly respond to internal stimuli including changes in ABA, auxin and calcium ion flux.

Thus, genes, gene products, and fragments thereof differentially transcribed and/or translated in guard cells can be useful to modulate ABA responses, drought tolerance, respiration, water potential, and water management as examples. All of which can in turn affect plant yield including seed yield, harvest index, fruit yield, etc.

To identify such guard cell genes, gene products, and fragments thereof, Applicants have performed a microarray experiment comparing the transcript levels of genes in guard cells versus leaves. Experimental data is shown below.

Nitric Oxide Responsive Genes, Gene Components and Products

The rate-limiting element in plant growth and yield is often its ability to tolerate suboptimal or stress conditions, including pathogen attack conditions, wounding and the presence of various other factors. To combat such conditions, plant cells deploy a battery of inducible defense responses, including synergistic interactions between nitric oxide (NO), reactive oxygen intermediates (ROS), and salicylic acid (SA). NO has been shown to play a critical role in the activation of innate immune and inflammatory responses in animals. At least part of this mammalian signaling pathway is present in plants, where NO is known to potentiate the hypersensitive response (HR). In addition, NO is a stimulator molecule in plant photomorphogenesis.

Changes in nitric oxide concentration in the internal or surrounding environment, or in contact with a plant, results in modulation of many genes and gene products.

In addition, the combination of a nitric oxide responsive polynucleotide and/or gene product with other environmentally responsive polynucleotides is also useful because of the interactions that exist between hormone regulated pathways, stress pathways, pathogen stimulated pathways, nutritional pathways and development.

Nitric oxide responsive genes and gene products can function either to increase or dampen the above phenotypes or activities either in response to changes in nitric oxide concentration or in the absence of nitric oxide fluctuations. More specifically, these genes and gene products can modulate stress responses in an organism. In plants, these genes and gene products are useful for modulating yield under stress conditions. Measurements of yield include seed yield, seed size, fruit yield, fruit size, etc.

Shoot-Apical Meristem Genes, Gene Components and Products

New organs, stems, leaves, branches and inflorescences develop from the stem apical meristem (SAM). The growth structure and architecture of the plant therefore depends on the behavior of SAMs. Shoot apical meristems (SAMs) are comprised of a number of morphologically undifferentiated, dividing cells located at the tips of shoots. SAM genes elucidated here are capable of modifying the activity of SAMs and thereby many traits of economic interest from ornamental leaf shape to organ number to responses to plant density.

In addition, a key attribute of the SAM is its capacity for self-renewal. Thus, SAM genes of the instant invention are useful for modulating one or more processes of SAM structure and/or function including (I) cell size and division; (II) cell differentiation and organ primordia. The genes and gene components of this invention are useful for modulating any one or all of these cell division processes generally, as in timing and rate, for example. In addition, the polynucleotides and polypeptides of the invention can control the response of these processes to the internal plant programs associated with embryogenesis, and hormone responses, for example.

Because SAMs determine the architecture of the plant, modified plants will be useful in many agricultural, horticultural, forestry and other industrial sectors. Plants with a different shape, numbers of flowers and seed and fruits will have altered yields of plant parts. For example, plants with more branches can produce more flowers, seed or fruits. Trees without lateral branches will produce long lengths of clean timber. Plants with greater yields of specific plant parts will be useful sources of constituent chemicals.

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

TABLE 1

REFERENCE TABLE

Max Len. Seq. :
rel to:
Clone IDs:
    1093453
(Ac) cDNA SEQ
    Pat. Appln. SEQ ID NO: 1
    Ceres SEQ ID NO: 4788142
  PolyP SEQ
    Pat. Appln. SEQ ID NO 2
    Ceres SEQ ID NO 4788143
    Loc. SEQ ID NO 1: @ 89 nt.
    (C) Pred. PP Nom. & Annot.
    (Dp) Rel. AA SEQ
      Align. NO 1
      gi No 30694168
      Desp. : expressed protein [*Arabidopsis thaliana*]
      % Idnt. : 63.8
      Align. Len.: 105
      Loc. SEQ ID NO 2: 1 -> 92 aa.
  PolyP SEQ
    Pat. Appln. SEQ ID NO 3
    Ceres SEQ ID NO 4788144
    Loc. SEQ ID NO 1: @ 167 nt.
    (C) Pred. PP Nom. & Annot.
    (Dp) Rel. AA SEQ
      Align. NO 2
      gi No 30694168
      Desp. : expressed protein [*Arabidopsis thaliana*]
      % Idnt. : 63.8
      Align. Len.: 105
      Loc. SEQ ID NO 3: 1 -> 66 aa.
  PolyP SEQ
    Pat. Appln. SEQ ID NO 4
    Ceres SEQ ID NO 4788145
    Loc. SEQ ID NO 1: @ 183 nt.
    (C) Pred. PP Nom. & Annot.
    (Dp) Rel. AA SEQ
Max Len. Seq. :
rel to:
Clone IDs:
    1079596
(Ac) cDNA SEQ
    Pat. Appln. SEQ ID NO: 5
    Ceres SEQ ID NO: 4796909
  PolyP SEQ
    Pat. Appln. SEQ ID NO 6
    Ceres SEQ ID NO 4796910
    Loc. SEQ ID NO 5: @ 94 nt.
    (C) Pred. PP Nom. & Annot.
    (Dp) Rel. AA SEQ
      Align. NO 3
      gi No 30694168
      Desp. : expressed protein [*Arabidopsis thaliana*]
      % Idnt. : 63.9
      Align. Len.: 147
      Loc. SEQ ID NO 6: 1 -> 128 aa.
  PolyP SEQ
    Pat. Appln. SEQ ID NO 7
    Ceres SEQ ID NO 4796911
    Loc. SEQ ID NO 5: @ 172 nt.
    (C) Pred. PP Nom. & Annot.
    (Dp) Rel. AA SEQ
      Align. NO 4
      gi No 30694168
      Desp. : expressed protein [*Arabidopsis thaliana*]
      % Idnt. : 63.9
      Align. Len.: 147
      Loc. SEQ ID NO 7: 1 -> 102 aa.
  PolyP SEQ
    Pat. Appln. SEQ ID NO 8
    Ceres SEQ ID NO 4796912
    Loc. SEQ ID NO 5: @ 244 nt.
    (C) Pred. PP Nom. & Annot.
    (Dp) Rel. AA SEQ
      Align. NO 5
      gi No 30694168
      Desp. : expressed protein [*Arabidopsis thaliana*]
      % Idnt. : 63.9
      Align. Len.: 147
      Loc. SEQ ID NO 8: 1 -> 78 aa.
END_OF_FILE
Max Len. Seq. :
rel to:
Clone IDs:
    8161
Pub gDNA:
    gi No: 22329272
    Gen. seq. in cDNA:
      129945 . . . 129790 OCKHAM3-CDS
      129087 . . . 128929 OCKHAM3-CDS
      128845 . . . 128653 OCKHAM3-CDS
      128277 . . . 128165 OCKHAM3-CDS
      128081 . . . 128046 OCKHAM3-CDS
(Ac) cDNA SEQ
    Pat. Appln. SEQ ID NO: 9
    Ceres SEQ ID NO: 12321174
  PolyP SEQ
    Pat. Appln. SEQ ID NO 10
    Ceres SEQ ID NO 12321175
    Loc. SEQ ID NO 9: @ 113 nt.
    (C) Pred. PP Nom. & Annot.
    (Dp) Rel. AA SEQ
      Align. NO 6
      gi No 30694168
      Desp. : expressed protein [*Arabidopsis thaliana*]
      % Idnt. : 41.2
      Align. Len.: 102
      Loc. SEQ ID NO 10: 22 -> 118 aa.
Max Len. Seq. :
rel to:
Clone IDs:
    96
(Ac) cDNA SEQ
    Pat. Appln. SEQ ID NO: 11
    Ceres SEQ ID NO: 12323601
    SEQ 11 w. TSS:
      36
  PolyP SEQ
    Pat. Appln. SEQ ID NO 12
    Ceres SEQ ID NO 12323602
    Loc. SEQ ID NO 11: @ 2 nt.
    Loc. Sig. P. SEQ ID NO 12: @ 22 aa.
    (C) Pred. PP Nom. & Annot.
    (Dp) Rel. AA SEQ
      Align. NO 7
      gi No 30694168
      Desp. : expressed protein [*Arabidopsis thaliana*]
      % Idnt. : 99.6
      Align. Len.: 246
      Loc. SEQ ID NO 12: 28 -> 273 aa.
  PolyP SEQ
    Pat. Appln. SEQ ID NO 13
    Ceres SEQ ID NO 12323603
    Loc. SEQ ID NO 11: @ 83 nt.
    (C) Pred. PP Nom. & Annot.
    (Dp) Rel. AA SEQ
      Align. NO 8
      gi No 30694168
      Desp. : expressed protein [*Arabidopsis thaliana*]
      % Idnt. : 99.6
      Align. Len.: 246
      Loc. SEQ ID NO 13: 1 -> 246 aa.
  PolyP SEQ
    Pat. Appln. SEQ ID NO 14
    Ceres SEQ ID NO 12323604
    Loc. SEQ ID NO 11: @ 188 nt.
    (C) Pred. PP Nom. & Annot.
    (Dp) Rel. AA SEQ
      Align. NO 9
      gi No 30694168
      Desp. : expressed protein [*Arabidopsis thaliana*]
      % Idnt. : 99.6
      Align. Len.: 246
      Loc. SEQ ID NO 14: 1 -> 211 aa.

TABLE 1-continued

REFERENCE TABLE

Max Len. Seq. :
rel to:
Clone IDs:
    8490
Pub gDNA:
    gi No: 22328163
    Gen. seq. in cDNA:
        147882 ... 147775 OCKHAM3-CDS
        147419 ... 147237 OCKHAM3-CDS
        147148 ... 146863 OCKHAM3-CDS
        146779 ... 146673 OCKHAM3-CDS
        146592 ... 146536 OCKHAM3-CDS
    gi No: 22328163
    Gen. seq. in cDNA:
        7882 ... 7775 OCKHAM3-CDS
        7419 ... 7237 OCKHAM3-CDS
        7148 ... 6863 OCKHAM3-CDS
        6779 ... 6673 OCKHAM3-CDS
        6592 ... 6536 OCKHAM3-CDS
(Ac) cDNA SEQ
    Pat. Appln. SEQ ID NO: 15
    Ceres SEQ ID NO: 13491409
PolyP SEQ
    Pat. Appln. SEQ ID NO 16
    Ceres SEQ ID NO 13491410
    Loc. SEQ ID NO 15: @ 2 nt.
    Loc. Sig. P. SEQ ID NO 16: @ 21 aa.
    (C) Pred. PP Nom. & Annot.
    (Dp) Rel. AA SEQ
        Align. NO 10
        gi No 30694168
        Desp. : expressed protein [*Arabidopsis thaliana*]
        % Idnt. : 99.6
        Align. Len.: 246
        Loc. SEQ ID NO 16: 27 -> 272 aa.
PolyP SEQ
    Pat. Appln. SEQ ID NO 17
    Ceres SEQ ID NO 13491411
    Loc. SEQ ID NO 15: @ 80 nt.
    (C) Pred. PP Nom. & Annot.
    (Dp) Rel. AA SEQ
        Align. NO 11
        gi No 30694168
        Desp. : expressed protein [*Arabidopsis thaliana*]
        % Idnt. : 99.6
        Align. Len.: 246
        Loc. SEQ ID NO 17: 1 -> 246 aa.
PolyP SEQ
    Pat. Appln. SEQ ID NO 18
    Ceres SEQ ID NO 13491412
    Loc. SEQ ID NO 15: @ 185 nt.
    (C) Pred. PP Nom. & Annot.
    (Dp) Rel. AA SEQ
        Align. NO 12
        gi No 30694168
        Desp. : expressed protein [*Arabidopsis thaliana*]
        % Idnt. : 99.6
        Align. Len.: 246
        Loc. SEQ ID NO 18: 1 -> 211 aa.
END_OF_FILE
Max Len. Seq. :
rel to:
Clone IDs:
    305463
(Ac) cDNA SEQ
    Pat. Appln. SEQ ID NO: 1
    Ceres SEQ ID NO: 12355477
    SEQ 1 w. TSS:
        27
PolyP SEQ
    Pat. Appln. SEQ ID NO 2
    Ceres SEQ ID NO 12355478
    Loc. SEQ ID NO 1: @ 462 nt.
    (C) Pred. PP Nom. & Annot.
    (Dp) Rel. AA SEQ
PolyP SEQ
    Pat. Appln. SEQ ID NO 3
    Ceres SEQ ID NO 12355479
    Loc. SEQ ID NO 1: @ 549 nt.
    (C) Pred. PP Nom. & Annot.
    (Dp) Rel. AA SEQ
PolyP SEQ
    Pat. Appln. SEQ ID NO 4
    Ceres SEQ ID NO 12355480
    Loc. SEQ ID NO 1: @ 597 nt.
    (C) Pred. PP Nom. & Annot.
    (Dp) Rel. AA SEQ
Max Len. Seq. :
rel to:
Clone IDs:
    258437
(Ac) cDNA SEQ
    Pat. Appln. SEQ ID NO: 5
    Ceres SEQ ID NO: 12410516
    SEQ 5 w. TSS:
        22,79,83,85
PolyP SEQ
    Pat. Appln. SEQ ID NO 6
    Ceres SEQ ID NO 12410517
    Loc. SEQ ID NO 5: @ 553 nt.
    (C) Pred. PP Nom. & Annot.
    (Dp) Rel. AA SEQ
PolyP SEQ
    Pat. Appln. SEQ ID NO 7
    Ceres SEQ ID NO 12410518
    Loc. SEQ ID NO 5: @ 637 nt.
    (C) Pred. PP Nom. & Annot.
    (Dp) Rel. AA SEQ
PolyP SEQ
    Pat. Appln. SEQ ID NO 8
    Ceres SEQ ID NO 12410519
    Loc. SEQ ID NO 5: @ 667 nt.
    (C) Pred. PP Nom. & Annot.
    (Dp) Rel. AA SEQ
END_OF_FILE

TABLE 3

| Matrix corn | | | | | | | | | | | | |
|---|---|---|---|---|---|---|---|---|---|---|---|---|
| 28 | 29 | 30 | 31 | 32 | 33 | 34 | 35 | 36 | 37 | 38 | 39 | 40 |
| 2 | 2 | 2 | 2 | 2 | 2 | 2 | 2 | 2 | 2 | 2 | 2 | 2 |
| 1 | 2 | 2 | 1 | 2 | 1 | 2 | 2 | 2 | 2 | 2 | 2 | 1 |
| v | ek | ga | e | tp | t | sa | sg | mg | yi | sa | ak | g |
| 41 | 42 | 43 | 44 | 45 | 46 | 47 | 48 | 49 | 50 | 51 | 52 | 53 |
| 2 | 2 | 2 | 2 | 2 | 2 | 2 | 2 | 2 | 2 | 2 | 2 | 2 |
| 2 | 2 | 2 | 2 | 3 | 2 | 3 | 1 | 1 | 2 | 1 | 2 | 1 |
| kn | er | yv | ml | eds | ta | emg | w | t | nd | e | kr | h |

TABLE 3-continued

Matrix corn

| 54 | 55 | 56 | 57 | 58 | 59 | 60 | 61 | 62 | 63 | 64 | 65 | 66 |
|---|---|---|---|---|---|---|---|---|---|---|---|---|
| 2 | 2 | 2 | 2 | 2 | 2 | 2 | 2 | 2 | 2 | 2 | 2 | 2 |
| 3 | 2 | 1 | 2 | 2 | 1 | 1 | 1 | 1 | 1 | 1 | 1 | 2 |
| smr | ls | y | li | ks | s | m | e | a | s | f | v | de |

| 67 | 68 | 69 | 70 | 71 | 72 | 73 | 74 | 75 | 76 | 77 | 78 | 79 |
|---|---|---|---|---|---|---|---|---|---|---|---|---|
| 2 | 2 | 2 | 2 | 2 | 2 | 2 | 2 | 2 | 2 | 2 | 2 | 2 |
| 1 | 1 | 1 | 1 | 2 | 1 | 1 | 3 | 3 | 2 | 3 | 2 | 2 |
| q | l | y | n | sh | l | g | ans | lhr | gp | khr | nd | ea |

| 80 | 81 | 82 | 83 | 84 | 85 | 86 | 87 | 88 | 89 | 90 | 91 | 92 |
|---|---|---|---|---|---|---|---|---|---|---|---|---|
| 2 | 2 | 2 | 2 | 2 | 2 | 2 | 2 | 2 | 2 | 2 | 2 | 2 |
| 1 | 2 | 2 | 1 | 1 | 1 | 1 | 2 | 1 | 2 | 1 | 1 | 1 |
| n | vg | st | e | s | t | r | fs | g | sa | g | r | k |

| 93 | 94 | 95 | 96 | 97 | 98 | 99 | 100 | 101 | 102 | 103 | 104 | 105 |
|---|---|---|---|---|---|---|---|---|---|---|---|---|
| 2 | 2 | 2 | 2 | 2 | 2 | 2 | 2 | 2 | 2 | 2 | 2 | 2 |
| 1 | 1 | 1 | 1 | 2 | 1 | 1 | 2 | 2 | 3 | 3 | 2 | 4 |
| p | s | q | e | qa | f | k | va | li | hrq | dre | ge | fvyl |

| 106 | 107 | 108 | 109 | 110 | 111 | 112 | 113 | 114 | 115 | 116 | 117 | 118 |
|---|---|---|---|---|---|---|---|---|---|---|---|---|
| 2 | 2 | 2 | 2 | 2 | 2 | 2 | 2 | 2 | 2 | 2 | 2 | 2 |
| 3 | 2 | 3 | 3 | 4 | 4 | 4 | 4 | 3 | 4 | 2 | 2 | 2 |
| wvc | qe | kys | iem | nekr | vyti | kedp | qkar | ptd | esvd | ha | rp | iv |

| 119 | 120 | 121 | 122 | 123 | 124 | 125 | 126 | 127 | 128 | 129 | 130 | 131 |
|---|---|---|---|---|---|---|---|---|---|---|---|---|
| 2 | 2 | 2 | 2 | 2 | 2 | 2 | 2 | 2 | 2 | 2 | 2 | 2 |
| 1 | 1 | 1 | 2 | 2 | 2 | 3 | 3 | 2 | 4 | 2 | 2 | 3 |
| n | g | r | hr | gs | ga | nak | skc | hc | ecgd | fv | lp | rae |

| 132 | 133 | 134 | 135 | 136 | 137 | 138 | 139 | 140 | 141 | 142 | 143 | 144 |
|---|---|---|---|---|---|---|---|---|---|---|---|---|
| 2 | 2 | 2 | 2 | 2 | 2 | 2 | 2 | 2 | 2 | 2 | 2 | 2 |
| 2 | 1 | 1 | 2 | 3 | 2 | 2 | 2 | 1 | 2 | 2 | 2 | 3 |
| sn | p | w | imv | krq | hr | yf | kr | p | lr | vd | kc | tgr |

| 145 | 146 | 147 | 148 | 149 | 150 | 151 | 152 | 153 | 154 | 155 | 156 | 157 |
|---|---|---|---|---|---|---|---|---|---|---|---|---|
| 2 | 2 | 2 | 2 | 2 | 2 | 2 | 2 | 2 | 2 | 2 | 2 | 2 |
| 3 | 3 | 3 | 3 | 3 | 1 | 3 | 4 | 2 | 3 | 4 | 3 | 3 |
| qsg | inv | pah | vqh | tsg | d | eag | pvgm | en | nav | qsae | vrp | vgl |

| 158 | 159 | 160 | 161 | 162 | 163 | 164 | 165 | 166 | 167 | 168 | 169 | 170 |
|---|---|---|---|---|---|---|---|---|---|---|---|---|
| 2 | 2 | 2 | 2 | 2 | 2 | 2 | 2 | 2 | 2 | 2 | 2 | 2 |
| 3 | 4 | 4 | 2 | 2 | 3 | 3 | 2 | 3 | 3 | 3 | 1 | 2 |
| sdv | shgd | selg | nsgy | gd | kts | kqv | ga | isd | crl | ske | s | gp |

| 171 | 172 | 173 | 174 | 175 | 176 | 177 | 178 | 179 | 180 | 181 | 182 | 183 |
|---|---|---|---|---|---|---|---|---|---|---|---|---|
| 2 | 2 | 2 | 2 | 2 | 2 | 2 | 2 | 2 | 2 | 2 | 2 | 2 |
| 2 | 4 | 3 | 4 | 3 | 2 | 3 | 2 | 2 | 2 | 1 | 3 | 3 |
| st | aved | sat | shna | lgr | kr | qes | lr | sg | sa | h | scg | rkp |

| 184 | 185 | 186 | 187 | 188 | 189 | 190 | 191 | 192 | 193 | 194 | 195 | 196 |
|---|---|---|---|---|---|---|---|---|---|---|---|---|
| 2 | 2 | 2 | 2 | 2 | 2 | 2 | 2 | 2 | 2 | 2 | 2 | 2 |
| 3 | 4 | 3 | 2 | 2 | 3 | 3 | 3 | 2 | 3 | 1 | 1 | 2 |
| dge | herp | dpr | qk | il | sla | vhk | gea | es | atr | e | v | st |

| 197 | 198 | 199 | 200 | 201 | 202 | 203 | 204 | 205 | 206 | 207 | 208 | 209 |
|---|---|---|---|---|---|---|---|---|---|---|---|---|
| 2 | 2 | 2 | 2 | 2 | 2 | 2 | 2 | 2 | 2 | 2 | 2 | 2 |
| 1 | 1 | 1 | 1 | 3 | 3 | 2 | 2 | 2 | 3 | 3 | 2 | 2 |
| d | q | n | f | vap | nde | ed | ge | ia | keq | gas | es | nt |

| 210 | 211 | 212 | 213 | 214 | 215 | 216 | 217 | 218 | 219 | 220 | 221 | 222 | 223 |
|---|---|---|---|---|---|---|---|---|---|---|---|---|---|
| 2 | 2 | 2 | 2 | 2 | 2 | 2 | 2 | 2 | 2 | 2 | 2 | 2 | 2 |
| 2 | 2 | 3 | 1 | 3 | 4 | 1 | 3 | 2 | 2 | 2 | 1 | 2 | 3 |
| ge | sa | smc | k | kar | mcyq | k | tks | vr | mr | ml | s | er | sat |

TABLE 4 matrix_e17

| 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|
| 2 2 | 2 2 | 2 3 | 2 5 | 2 4 | 2 5 | 2 3 | 2 3 | 2 3 | 2 5 | 2 2 | 2 3 | 2 3 | 2 2 | 2 4 | 2 4 | 2 4 | 2 5 | 2 6 | 2 7 | 2 7 | 2 6 | 2 7 | 2 6 |
| se | st | dst | dgsel | astl | sqtyn | sfg | vly | egd | geqsh | eg | tae | tlv | sa | srqt | mlqs | yedm | sfgka | aeqpsdgevrmkkntliqeedagtl | | | | | ydptsikmktlse |

| 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 |
|---|---|---|---|---|---|---|---|---|---|---|---|---|---|---|---|---|---|---|---|---|---|---|---|---|---|---|
| 2 7 | 2 5 | 2 4 | 2 1 | 2 1 | 2 2 | 2 1 | 2 2 | 2 1 | 2 4 | 2 3 | 2 1 | 2 2 | 2 4 | 2 2 | 2 3 | 2 1 | 2 2 | 2 1 | 2 1 | 2 1 | 2 5 | 2 1 | 2 2 | 2 2 | 2 3 | 2 2 |
| epsaqr | tapsg | egqa | w | t | nd | e | kr | h | smrn | lms | y | li | knsd | sy | mil | e | as | s | f | v | dnser | q | ls | yh | nde | sh |

| 72 | 73 | 74 | 75 | 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|---|---|---|---|
| 2 3 | 2 4 | 2 2 | 2 2 | 2 2 | 2 5 | 2 6 | 2 9 | 2 7 | 2 6 | 2 6 | 2 6 | 2 5 | 2 5 | 2 6 | 2 9 | 2 7 | 2 5 | 2 4 |
| lsm | gnds | al | lq | gs | ksryg | nkqesgednwmgntksaecvptckr | | | | sgptkl | | epnyskshdrl | | trspm | rqhapk | fkdtnengdatvq | sdcnh | gnca |

| 91 | 92 | 93 | 94 | 95 | 96 | 97 | 98 | 99 | 100 | 101 | 102 | 103 | 104 | 105 | 106 | 107 | 108 | 109 | 110 | 111 |
|---|---|---|---|---|---|---|---|---|---|---|---|---|---|---|---|---|---|---|---|---|
| 2 7 | 2 5 | 2 5 | 2 2 | 2 4 | 2 4 | 2 3 | 2 2 | 2 2 | 2 2 | 2 4 | 2 4 | 2 5 | 2 2 | 2 7 | 2 2 | 2 4 | 2 4 | 2 4 | 2 5 | 2 5 |
| rgtipnskcarh | pitsk | sp | qesa | egad | qge | fy | kt | va | lhfi | hrkq | dgren | ge | fsvcyn | wc | qekt | kygs | imkv | neskr | vcyfi | |

| 112 | 113 | 114 | 115 | 116 | 117 | 118 | 119 | 120 | 121 | 122 | 123 | 124 | 125 | 126 | 127 | 128 | 129 | 130 |
|---|---|---|---|---|---|---|---|---|---|---|---|---|---|---|---|---|---|---|
| 2 7 | 2 4 | 2 6 | 2 6 | 2 2 | 2 6 | 2 5 | 2 7 | 2 4 | 2 4 | 2 4 | 2 3 | 2 6 | 2 6 | 2 6 | 2 2 | 2 6 | 2 7 | 2 5 |
| krvempqrky | patved | esnkmdhyapts | rpqdk | ilvtamdnsp | gkvs | rskt | hsrk | gia | granke | ngrkqe | sc | hdcrat | edgrva | flvise | lqptf | | | |

| 131 | 132 | 133 | 134 | 135 | 136 | 137 | 138 | 139 | 140 | 141 | 142 | 143 | 144 | 145 | 146 | 147 | 148 | 149 | 150 |
|---|---|---|---|---|---|---|---|---|---|---|---|---|---|---|---|---|---|---|---|
| 2 5 | 2 3 | 2 2 | 2 2 | 2 4 | 2 4 | 2 2 | 2 3 | 2 4 | 2 3 | 2 6 | 2 7 | 2 4 | 2 6 | 2 7 | 2 9 | 2 6 | 2 8 | 2 8 | 2 4 |
| rsaet | sdn | pe | wf | lmvr | krqf | hr | yfr | knrt | psn | lsrega | vprdsg | krcv | tsgqah | qlsrahnitdnspnpdaisr | | vgqarl | tslvqngdspe | | |

| 151 | 152 | 153 | 154 | 155 | 156 | 157 | 158 | 159 | 160 | 161 | 162 | 163 | 164 | 165 | 166 | 167 | 168 | 169 | 170 |
|---|---|---|---|---|---|---|---|---|---|---|---|---|---|---|---|---|---|---|---|
| 2 8 | 2 5 | 2 3 | 2 6 | 2 5 | 2 5 | 2 4 | 2 4 | 2 7 | 2 5 | 2 7 | 2 4 | 2 6 | 2 7 | 2 6 | 2 8 | 2 6 | 2 7 | 2 5 | 2 5 |
| efasgcrplvga | eqn | neaqgyqnsat | varrnt | vagt | sdtl | sthgvarselkv | | nksgfprgdsn | | kitqsd | kvqrihsgakvepivsgdmcrsvli | | sckpedsgcfd | gpaks | | | | | |

| 171 | 172 | 173 | 174 | 175 | 176 | 177 | 178 | 179 | 180 | 181 | 182 | 183 | 184 | 185 | 186 | 187 | 188 | 189 | 190 |
|---|---|---|---|---|---|---|---|---|---|---|---|---|---|---|---|---|---|---|---|
| 2 5 | 2 7 | 2 6 | 2 5 | 2 4 | 2 4 | 2 5 | 2 4 | 2 3 | 2 4 | 2 4 | 2 5 | 2 4 | 2 6 | 2 5 | 2 6 | 2 4 | 2 6 | 2 6 | 2 7 |
| sdtay | asvgeitsthaqe | snftg | lrst | kqld | qfhst | lita | scl | swer | hnse | sgryp | rlvp | dyecsphrdep | | drpkqs | qdke | ismlyt | svliak | vlghyc | |

| 191 | 192 | 193 | 194 | 195 | 196 | 197 | 198 | 199 | 200 | 201 | 202 | 203 |
|---|---|---|---|---|---|---|---|---|---|---|---|---|
| 2 5 | 2 4 | 2 5 | 2 1 | 2 3 | 2 3 | 2 2 | 2 1 | 2 1 | 2 1 | 2 6 | 2 3 | 2 2 |
| gseda | ensd | aeitr | e | vma | stm | dg | q | n | f | vmaipr | nde | ed |

TABLE 9

PARAMETERS FOR DIFFERENTIAL ANALYSIS

| Utility section | Expt Rep ID | Short Name | Parameter | Value |
|---|---|---|---|---|
| Viability | 107881 | At_Herbicide_v2_cDNA_P | Timepoint (hr) | 4 |
| | 107881 | At_Herbicide_v2_cDNA_P | Treatment | Glean vs. No Treatment |
| | 107891 | At_Herbicide_v2_cDNA_P | Timepoint (hr) | 12 |
| | 107891 | At_Herbicide_v2_cDNA_P | Treatment | Trimec vs. No Treatment |
| Root | 108429 | At_Tissue_Specific_Expression_cDNA_P | Probe Amount | 50 |
| | 108429 | At_Tissue_Specific_Expression_cDNA_P | Probe Method | operon |
| | 108429 | At_Tissue_Specific_Expression_cDNA_P | Tissue | Green Flower vs. Whole Plant |
| Root | 108434 | At_Root_Tips_cDNA_P | Tissue | Root Tips |
| Shoot Meristem | 108435 | At_stm_Mutants_cDNA_P | Plant Line | wt Landsburg vs stm |
| | 108435 | At_stm_Mutants_cDNA_P | Tissue | Shoot Apical Meristem Region |
| Reproductive and Seed & Fruit Development | 108437 | At_Tissue_Specific_Expression_cDNA_P | Probe Amount | 33 |
| | 108437 | At_Tissue_Specific_Expression_cDNA_P | Probe Method | operon |
| | 108437 | At_Tissue_Specific_Expression_cDNA_P | Tissue | <5 mm Siliques vs. Whole Plant |

TABLE 9-continued

PARAMETERS FOR DIFFERENTIAL ANALYSIS

| Utility section | Expt Rep ID | Short Name | Parameter | Value |
|---|---|---|---|---|
| Reproductive and Seed & Fruit Development | 108438 | At_Tissue_Specific_Expression_cDNA_P | Probe Amount | 33 |
| | 108438 | At_Tissue_Specific_Expression_cDNA_P | Probe Method | operon |
| | 108438 | At_Tissue_Specific_Expression_cDNA_P | Tissue | 5 wk Siliques vs. Whole Plant |
| Root | 108439 | At_Tissue_Specific_Expression_cDNA_P | Probe Amount | 33 |
| | 108439 | At_Tissue_Specific_Expression_cDNA_P | Probe Method | operon |
| | 108439 | At_Tissue_Specific_Expression_cDNA_P | Tissue | Roots (2 wk) vs. Whole Plant |
| Imbibition & Germination | 108461 | At_Germinating_Seeds_cDNA_P | Age | 1 vs. 0 |
| | 108461 | At_Germinating_Seeds_cDNA_P | Tissue | Germinating Seeds |
| Imbibition & Germination | 108462 | At_Germinating_Seeds_cDNA_P | Age | 2 vs. 0 |
| | 108462 | At_Germinating_Seeds_cDNA_P | Tissue | Greminating Seeds |
| Early Seedling Phase | 108463 | At_Germinating_Seeds_cDNA_P | Age | 3 vs. 0 |
| | 108463 | At_Germinating_Seeds_cDNA_P | Tissue | Germinating Seeds |
| Early Seedling Phase | 108464 | At_Germinating_Seeds_cDNA_P | Age | 4 vs. 0 |
| | 108464 | At_Germinating_Seeds_cDNA_P | Tissue | Germinating Seeds |
| Viability | 108465 | At_Herbicide_v3_1_cDNA_P | Timepoint (hr) | 12 |
| | 108465 | At_Herbicide_v3_1_cDNA_P | Treatment | Roundup vs. No Treatment |
| Drought and Reproductive | 108473 | At_Drought_Flowers_cDNA_P | Timepoint (hr) | 7 d |
| | 108473 | At_Drought_Flowers_cDNA_P | Tissue | Flowers |
| | 108473 | At_Drought_Flowers_cDNA_P | Treatment | Drought vs. No Drought |
| Shoot Meristem | 108480 | At_Shoot_Apices_cDNA_P | Plant Line | Ws-2 |
| | 108480 | At_Shoot_Apices_cDNA_P | Treatment | 1 uM BR vs. No Treatment |
| Shoot Meristem | 108481 | At_Shoot_Apices_cDNA_P | Plant Line | Ws-2 |
| | 108481 | At_Shoot_Apices_cDNA_P | Treatment | 1 uM BRZ vs. No Treatment |
| Leaves | 108488 | At_50mM_NH4NO3_L-to-H_Rosette_cDNA_P | Timepoint (hr) | 2 |
| Heat | 108523 | Zm_42deg_Heat_P | Temperature | Heat (42 deg C.) |
| | 108523 | Zm_42deg_Heat_P | Timepoint (hr) | 6 |
| | 108523 | Zm_42deg_Heat_P | Tissue | Aerial |
| Imbibition & Germination | 108528 | Zm_Imbibed_Seeds_P | Age | 5 vs. 2 |
| | 108528 | Zm_Imbibed_Seeds_P | Tissue | Aerial vs. Embryo |
| | 108528 | Zm_Imbibed_Seeds_P | Treatment | Imbibition |
| Imbibition & Germination | 108530 | Zm_Imbibed_Seeds_P | Age | 6 vs. 2 |
| | 108530 | Zm_Imbibed_Seeds_P | Tissue | Aerial vs. Embryo |
| | 108530 | Zm_Imbibed_Seeds_P | Treatment | Imbibition |
| Imbibition & Germination, Reproductive | 108543 | Zm_Imbibed_Embryo_Endosperm_P | Age | 2 |
| | 108543 | Zm_Imbibed_Embryo_Endosperm_P | Tissue | Embryo vs. Whole Plant |
| | 108543 | Zm_Imbibed_Embryo_Endosperm_P | Treatment | Imbibed |
| Imbibition & Germination | 108546 | Zm_Imbibed_Seeds_P | Age | 3 vs. 2 |
| | 108546 | Zm_Imbibed_Seeds_P | Tissue | Roots vs. Embryo |
| | 108546 | Zm_Imbibed_Seeds_P | Treatment | Imbibition |
| Jasmonate | 108569 | At_0.001%_MeJA_cDNA_P | Timepoint (hr) | 6 |
| | 108569 | At_0.001%_MeJA_cDNA_P | Tissue | Aerial |
| | 108569 | At_0.001%_MeJA_cDNA_P | Treatment | 0.001% MeJA vs. No Treatment |
| Heat | 108577 | At_42deg_Heat_cDNA_P | Temperature | 42 vs. 22 |
| | 108577 | At_42deg_Heat_cDNA_P | Timepoint (hr) | 6 |
| | 108577 | At_42deg_Heat_cDNA_P | Tissue | Aerial |
| Cold | 108579 | At_4deg_Cold_cDNA_P | Temperature | 4 vs. 22 |
| | 108579 | At_4deg_Cold_cDNA_P | Timepoint (hr) | 6 |
| | 108579 | At_4deg_Cold_cDNA_P | Tissue | Aerial |
| Root and Root Hairs | 108594 | At_Ler-rhl_Root_cDNA_P | Plant Line | Ler_rhl |
| | 108594 | At_Ler-rhl_Root_cDNA_P | Tissue | Root |
| ABA, Drought, Germination | 108614 | At_100uM_ABA_Mutants_cDNA_P | Plant Line | CS24 |
| | 108614 | At_100uM_ABA_Mutants_cDNA_P | Timepoint (hr) | 6 |
| | 108614 | At_100uM_ABA_Mutants_cDNA_P | Tissue | Aerial |
| | 108614 | At_100uM_ABA_Mutants_cDNA_P | Treatment | 100 uM ABA vs. No Treatment |
| ABA, Drought, Germination | 108622 | At_100uM_ABA_Mutants_cDNA_P | Plant Line | CS22 |
| | 108622 | At_100uM_ABA_Mutants_cDNA_P | Timepoint (hr) | 6 |
| | 108622 | At_100uM_ABA_Mutants_cDNA_P | Tissue | Aerial |
| | 108622 | At_100uM_ABA_Mutants_cDNA_P | Treatment | 100 uM ABA vs. No Treatment |
| Viability | 108629 | At_Herbicide_v3_1_cDNA_P | Timepoint (hr) | 1 |
| | 108629 | At_Herbicide_v3_1_cDNA_p | Treatment | Glean vs. No Treatment |
| Viability | 108630 | At_Herbicide_v3_1_cDNA_P | Timepoint (hr) | 1 |
| | 108630 | At_Herbicide_v3_1_cDNA_P | Treatment | Trimec vs. No Treatment |
| Salicylic Acid | 108668 | At_2mM_SA_cDNA_P | Plant Line | WS |
| | 108668 | At_2mM_SA_cDNA_P | Timepoint (hr) | 6 |
| | 108668 | At_2mM_SA_cDNA_P | Treatment | 2 mM SA vs. No Treatment |
| Reproductive and Seed & Fruit Development | 108687 | Zm_Embryos-Flowers_P | Tissue | Embryo |
| | 108688 | Zm_Embryos-Flowers_P | Tissue | Immature Flowers |
| ABA, Drought, Germination | 20000069 | At_100uM_ABA_Mutants_cDNA_P | Plant Line | CS23 |
| | 20000069 | At_100uM_ABA_Mutants_cDNA_P | Timepoint (hr) | 6 |
| | 20000069 | At_100uM_ABA_Mutants_cDNA_P | Tissue | Aerial |
| | 20000069 | At_100uM_ABA_Mutants_cDNA_P | Treatment | 100 uM ABA vs. No Treatment |

TABLE 9-continued

PARAMETERS FOR DIFFERENTIAL ANALYSIS

| Utility section | Expt Rep ID | Short Name | Parameter | Value |
|---|---|---|---|---|
| ABA, Drought, Germination | 20000070 | At_100uM_ABA_Mutants_cDNA_P | Plant Line | CS24 |
| | 20000070 | At_100uM_ABA_Mutants_cDNA_P | Timepoint (hr) | 6 |
| | 20000070 | At_100uM_ABA_Mutants_cDNA_P | Tissue | Aerial |
| | 20000070 | At_100uM_ABA_Mutants_cDNA_P | Treatment | 100 uM ABA vs. No Treatment |
| ABA, Drought, Germination | 20000071 | At_100uM_ABA_Mutants_cDNA_P | Plant Line | CS8104 |
| | 20000071 | At_100uM_ABA_Mutants_cDNA_P | Timepoint (hr) | 6 |
| | 20000071 | At_100uM_ABA_Mutants_cDNA_P | Tissue | Aerial |
| | 20000071 | At_100uM_ABA_Mutants_cDNA_P | Treatment | 100 uM ABA vs. No Treatment |
| ABA. Drought, Germination | 20000072 | At_100uM_ABA_Mutants_cDNA_P | Plant Line | CS8105 |
| | 20000072 | At_100uM_ABA_Mutants_cDNA_P | Timepoint (hr) | 6 |
| | 20000072 | At_100uM_ABA_Mutants_cDNA_P | Tissue | Aerial |
| | 20000072 | At_100uM_ABA_Mutants_cDNA_P | Treatment | 100 uM ABA vs. No Treatment |
| ABA, Drought, Germination | 20000086 | At_100uM_ABA_Mutants_cDNA_P | Plant Line | CS22 |
| | 20000086 | At_100uM_ABA_Mutants_cDNA_P | Timepoint (hr) | 6 |
| | 20000086 | At_100uM_ABA_Mutants_cDNA_P | Tissue | aerial |
| | 20000086 | At_100uM_ABA_Mutants_cDNA_P | Treatment | 100 uM ABA vs. No Treatment |
| ABA, Drought, Germination | 20000087 | At_100uM_ABA_Mutants_cDNA_P | Plant Line | WS |
| | 20000087 | At_100uM_ABA_Mutants_cDNA_P | Timepoint (hr) | 6 |
| | 20000087 | At_100uM_ABA_Mutants_cDNA_P | Tissue | aerial |
| | 20000087 | At_100uM_ABA_Mutants_cDNA_P | Treatment | 100 uM ABA vs. No Treatment |
| ABA, Drought, Germination | 20000088 | At_100uM_ABA_Mutants_cDNA_P | Plant Line | Landsberg |
| | 20000088 | At_100uM_ABA_Mutants_cDNA_P | Timepoint (hr) | 6 |
| | 20000088 | At_100uM_ABA_Mutants_cDNA_P | Tissue | aeriel |
| | 20000088 | At_100uM_ABA_Mutants_cDNA_P | Treatment | 100 uM ABA vs. No Treatment |
| Salicylic Acid | 20000090 | At_2mM_SA_CS3726-Columbia_cDNA_P | Plant Line | Columbia |
| | 20000090 | At_2mM_SA_CS3726-Columbia_cDNA_P | Timepoint (hr) | 6 |
| | 20000090 | At_2mM_SA_CS3726-Columbia_cDNA_P | Tissue | Aerial |
| | 20000090 | At_2mM_SA_CS3726-Columbia_cDNA_P | Treatment | 2 mM SA vs. No Treatment |
| Heat | 20000111 | At_42deg_Heat_cDNA_P | Temperature | 42 vs. 23 |
| | 20000111 | At_42deg_Heat_cDNA_P | Timepoint (hr) | 6 |
| | 20000111 | At_42deg_Heat_cDNA_P | Tissue | Aerial |
| Heat | 20000113 | At_42deg_Heat_cDNA_P | Temperature | 42 vs. 23 |
| | 20000113 | At_42deg_Heat_cDNA_P | Timepoint (hr) | 8 |
| | 20000113 | At_42deg_Heat_cDNA_P | Tissue | Aerial |
| ABA, Drought, Germination | 20000117 | At_100uM_ABA_Mutants_cDNA_P | Plant Line | columbia |
| | 20000117 | At_100uM_ABA_Mutants_cDNA_P | Timepoint (hr) | 6 |
| | 20000117 | At_100uM_ABA_Mutants_cDNA_P | Tissue | aerial |
| | 20000117 | At_100uM_ABA_Mutants_cDNA_P | Treatment | 100 uM ABA vs. No Treatment |
| Heat | 20000171 | At_42deg_Heat_P | Probe Method | mRNA vs. mRNA |
| | 20000171 | At_42deg_Heat_P | Temperature | 42 vs. 22 |
| | 20000171 | At_42deg_Heat_P | Timepoint (hr) | 1 |
| | 20000171 | At_42deg_Heat_P | Tissue | Aerial |
| Heat | 20000173 | At_42deg_Heat_P | Probe Method | mRNA vs. mRNA |
| | 20000173 | At_42deg_Heat_P | Temperature | 42 vs. 22 |
| | 20000173 | At_42deg_Heat_P | Timepoint (hr) | 6 |
| | 20000173 | At_42deg_Heat_P | Tissue | Aerial |
| Early Seedling Phase | 20000179 | At_Germinating_Seeds_P | Age | 6 vs. 0 |
| | 20000179 | At_Germinating_Seeds_P | Tissue | Germinating Seeds |
| Early Seedling Phase | 20000180 | At_Germinating_Seeds_P | Age | 24 vs. 0 |
| | 20000180 | At_Germinating_Seeds_P | Tissue | Germinating Seeds |
| Salicylic Acid | 20000182 | At_2mM_SA_P | Timepoint (hr) | 6 |
| | 20000182 | At_2mM_SA_P | Tissue | Aerial |
| | 20000182 | At_2mM_SA_P | Treatment | 2 mM SA vs. No Treatment |
| Leaves, Shoot Meristem | 20000184 | At_Shoots_P | Age | 7 |
| | 20000184 | At_Shoots_P | Tissue | Shoots vs. Whole Plant |
| Root | 20000185 | At_Roots_P | Age | 7 |
| | 20000185 | At_Roots_P | Tissue | Roots vs. Whole Plant |
| Cold | 20000213 | At_4deg_Cold_P | Temperature | 4 vs. 22 |
| | 20000213 | At_4deg_Cold_P | Timepoint (hr) | 2 |
| Seed and Fruit Development | 20000234 | At_Siliques_P | Tissue | <5 mm Siliques vs. Whole Plant |
| Seed and Fruit Development | 20000235 | At_Siliques_YF_6-05-02_P | Tissue | 5-10 mm Siliques vs. Whole Plant |
| Seed and Fruit Development | 20000236 | At_Siliques_P | Tissue | >10 mm Siliques vs. Whole Plant |
| Reproductive and Seed & Fruit Development | 20000264 | At_Open_Flower_P | Tissue | Open Flower vs. Whole Plant |
| Reproductive and Seed & Fruit Development | 20000265 | At_Open_Flower_P | Tissue | Closed Bud vs. Whole Plant |
| Reproductive and Seed & Fruit Development | 20000286 | At_Open_Flower_P | Tissue | Half Open vs. Whole Plant |
| Drought | 20000437 | At_Drought_P | Timepoint (hr) | 24 |
| | 20000437 | At_Drought_P | Tissue | Whole Plant |
| | 20000437 | At_Drought_P | Treatment | Drought vs. No Drought |
| Leaves, Shoot Meristem | 20000438 | At_Shoots_P | Age | 14 |
| | 20000438 | At_Shoots_P | Tissue | Shoots vs. Whole Plant |
| Roots | 20000439 | At_Roots_P | Age | 14 |
| | 20000439 | At_Roots_P | Tissue | Roots vs. Whole Plant |

TABLE 9-continued

PARAMETERS FOR DIFFERENTIAL ANALYSIS

| Utility section | Expt Rep ID | Short Name | Parameter | Value |
|---|---|---|---|---|
| Brassinolide | 20000441 | At_1uM_BR-BRZ_P | Tissue | Shoot Apices |
| | 20000441 | At_1uM_BR-BRZ_P | Treatment | 1 uM BR vs. No Treatment |
| | 20000443 | At_1uM_BR-BRZ_P | Tissue | Shoot Apices |
| | 20000443 | At_1uM_BR-BRZ_P | Treatment | 1 uM BRZ vs. No Treatment |
| Salicylic Acid | 20000478 | Zm_5mM_SA_P | Age | 8 |
| | 20000478 | Zm_5mM_SA_P | Plant Line | Hybrid |
| | 20000478 | Zm_5mM_SA_P | Timepoint (hr) | 72 |
| | 20000478 | Zm_5mM_SA_P | Tissue | Aerial |
| | 20000478 | Zm_5mM_SA_P | Treatment | 5 mM SA vs. No Treatment |
| Reproductive and Seed & Fruit Development | 20000493 | Zm_Hybrid_Seed_Dev_P | DAP | 20 vs. 12 |
| | 20000493 | Zm_Hybrid_Seed_Dev_P | Plant Line | Hybrid |
| | 20000493 | Zm_Hybrid_Seed_Dev_P | Tissue | Endosperm vs. Unfert Floret |
| Guard Cells | 20000495 | At_Guard_Cells_P | Harvest Date | Aug. 2, 2002 |
| | 20000495 | At_Guard_Cells_P | Organism | *A. thaliana* |
| | 20000495 | At_Guard_Cells_P | Tissue | Guard Cells vs. Leaves |
| PEG | 20000527 | At_10%_PEG_P | Age | 20 |
| | 20000527 | At_10%_PEG_P | Tissue | Aerial |
| | 20000527 | At_10%_PEG_P | Treatment | 10% PEG vs. No Treatment |
| ABA, Drought, Germination | 20000573 | At_100uM_ABA_Mutants_P | Organism | *A. thaliana* |
| | 20000573 | At_100uM_ABA_Mutants_P | Plant Line | CS22 vs. Ler wt |
| | 20000573 | At_100uM_ABA_Mutants_P | Timepoint (hr) | N/A |
| | 20000573 | At_100uM_ABA_Mutants_P | Tissue | Whole Plant |
| | 20000573 | At_100uM_ABA_Mutants_P | Treatment | None |
| Viability | 20000629 | Zm_Herbicide-Treatments_P | Timepoint (hr) | 12 |
| | 20000629 | Zm_Herbicide-Treatments_P | Tissue | Aerial |
| | 20000629 | Zm_Herbicide-Treatments_P | Treatment | Trimec vs. No Treatment |
| Drought | 20000638 | At_Drought_cDNA_P | Timepoint (hr) | 144 |
| | 20000638 | At_Drought_cDNA_P | Tissue | sdf |
| Reproductive | 20000794 | At_Petals_P | Age | 23-25 days |
| | 20000794 | At_Petals_P | Tissue | Petals vs. Whole plant |
| Shade | 20001247 | At_Far-red-induction_P | Age | 7 |
| | 20001247 | At_Far-red-induction_P | Light | Far Red vs. White |
| | 20001247 | At_Far-red-induction_P | Plant Line | Columbia |
| | 20001247 | At_Far-red-induction_P | Timepoint (hr) | 1 |
| Shade | 20001248 | At_Far-red-induction_P | Age | 7 |
| | 20001248 | At_Far-red-induction_P | Light | Far Red vs. White |
| | 20001248 | At_Far-red-induction_P | Plant Line | Columbia |
| | 20001248 | At_Far-red-induction_P | Timepoint (hr) | 4 |
| Shade | 20001450 | At_Far-red-induction_P | Age | 7 |
| | 20001450 | At_Far-red-induction_P | Light | Far Red vs. White |
| | 20001450 | At_Far-red-induction_P | Plant Line | Columbia |
| | 20001450 | At_Far-red-induction_P | Timepoint (hr) | 8 |
| Shade | 20001451 | At_Far-red-induction_P | Age | 7 |
| | 20001451 | At_Far-red-induction_P | Light | Far Red vs. White |
| | 20001451 | At_Far-red-induction_P | Plant Line | Columbia |
| | 20001451 | At_Far-red-induction_P | Timepoint (hr) | 24 |
| Nitrogen | 20001459 | At_50mM_NH4NO3_L-to-H_P | Timepoint (hr) | 4 |
| | 20001459 | At_50mM_NH4NO3_L-to-H_P | Tissue | Siliques |
| | 20001459 | At_50mM_NH4NO3_L-to-H_P | Treatment | 50 mM NH4NO3 vs. 100 mM Manitol |
| Viability | 20000530 | Zm_2-4D_YF_8-26-02_P | Organism | *Zea Mays* |
| | 20000530 | Zm_2-4D_YF_8-26-02_P | Timepoint (hr) | 48 |
| | 20000530 | Zm_2-4D_YF_8-26-02_P | Tissue | Aerial |
| | 20000530 | Zm_2-4D_YF_8-26-02_P | Treatment | 2,4-D vs. No Treatment |
| Guard Cells | 20000570 | At_Guard_Cells_JD_9-9-02_cDNA_P | Harvest Date | Jul. 19, 2002 |
| | 20000570 | At_Guard_Cells_JD_9-9-02_cDNA_P | Organism | Canola |
| | 20000570 | At_Guard_Cells_JD_9-9-02_cDNA_P | Tissue | Guard Cells vs. Leaves |

TABLE 10

MA_DIFF TABLE
RESULTS FOR DIFFERENTIAL EXPRESSION ANALYSIS

| Clone | cDNA | Biomaterial | Expt_Rep_ID | Short_Name | Value (average log ratio) | Differential | Differential (+/−) |
|---|---|---|---|---|---|---|---|
| 96 | 12323601 | 1580810 | 20000527 | At_10%_PEG_P | 1.554916476 | 1 | + |
| 96 | 12323601 | 1580810 | 20000573 | At_100uM_ABA_Mutants_P | 1.433853789 | 1 | + |
| 96 | 12323601 | 1580810 | 20000441 | At_1uM_BR-BRZ_P | −3.010706617 | −1 | − |
| 96 | 12323601 | 1580810 | 20000443 | At_1uM_BR-BRZ_P | −2.748840687 | −1 | − |
| 96 | 12323601 | 1580810 | 20000171 | At_42deg_Heat_P | 1.514139809 | 1 | + |

TABLE 10-continued

MA_DIFF TABLE
RESULTS FOR DIFFERENTIAL EXPRESSION ANALYSIS

| Clone | cDNA | Biomaterial | Expt_Rep_ID | Short_Name | Value (average log ratio) | Differential | Differential (+/−) |
|---|---|---|---|---|---|---|---|
| 96 | 12323601 | 1580810 | 20000173 | At_42deg_Heat_P | −1.71925392 | −1 | − |
| 96 | 12323601 | 23030 | 108577 | At_42deg_Heat_cDNA_P | −3.338050794 | −1 | − |
| 96 | 12323601 | 1580810 | 20000213 | At_4deg_Cold_P | 2.813628804 | 1 | + |
| 96 | 12323601 | 23030 | 108579 | At_4deg_Cold_cDNA_P | 3.999311124 | 1 | + |
| 96 | 12323601 | 1580810 | 20001459 | At_50mM_NH4NO3_L-to-H_P | −1.715098188 | −1 | − |
| 96 | 12323601 | 1580810 | 20000437 | At_Drought_P | 4.220227281 | 1 | + |
| 96 | 12323601 | 1580810 | 20001247 | At_Far-red-induction_P | −4.634953394 | −1 | − |
| 96 | 12323601 | 1580810 | 20001248 | At_Far-red-induction_P | 5.592598825 | 1 | + |
| 96 | 12323601 | 1580810 | 20001450 | At_Far-red-induction_P | 1.649915315 | 1 | + |
| 96 | 12323601 | 1580810 | 20000180 | At_Germinating_Seeds_P | −2.680555133 | −1 | − |
| 96 | 12323601 | 1580810 | 20000495 | At_Guard_Cells_P | −3.247865708 | −1 | − |
| 96 | 12323601 | 1580810 | 20000264 | At_Open_Flower_P | −2.752089532 | −1 | − |
| 96 | 12323601 | 1580810 | 20000185 | At_Roots_P | −4.966099796 | −1 | − |
| 96 | 12323601 | 1580810 | 20000439 | At_Roots_P | −4.736820319 | −1 | − |
| 96 | 12323601 | 1580810 | 20000438 | At_Shoots_P | −4.72150623 | −1 | − |
| 96 | 12323601 | 1580810 | 20000234 | At_Siliques_P | −2.874162085 | −1 | − |
| 96 | 12323601 | 1580810 | 20000235 | At_Siliques_P | −2.246390758 | −1 | − |
| 96 | 12323601 | 1580810 | 20000236 | At_Siliques_P | −2.46053553 | −1 | − |
| 8161 | 12321174 | 19239 | 108569 | At_0.001%_MeJA_cDNA_P | −1.173013726 | −1 | − |
| 8161 | 12321174 | 1580012 | 20000527 | At_10%_PEG_P | 1.259078847 | 1 | + |
| 8161 | 12321174 | 19239 | 20000069 | At_100uM_ABA_Mutants_cDNA_P | 4.740481926 | 1 | + |
| 8161 | 12321174 | 19239 | 20000070 | At_100uM_ABA_Mutants_cDNA_P | 3.670069907 | 1 | + |
| 8161 | 12321174 | 19239 | 20000071 | At_100uM_ABA_Mutants_cDNA_P | 3.608787472 | 1 | + |
| 8161 | 12321174 | 19239 | 20000086 | At_100uM_ABA_Mutants_cDNA_P | 3.027039775 | 1 | + |
| 8161 | 12321174 | 19239 | 20000087 | At_100uM_ABA_Mutants_cDNA_P | 2.423296688 | 1 | + |
| 8161 | 12321174 | 19239 | 20000088 | At_100uM_ABA_Mutants_cDNA_P | 2.856206036 | 1 | + |
| 8161 | 12321174 | 19239 | 20000117 | At_100uM_ABA_Mutants_cDNA_P | 3.485993547 | 1 | + |
| 8161 | 12321174 | 19239 | 108614 | At_100uM_ABA_Mutants_cDNA_P | −1.365108521 | −1 | − |
| 8161 | 12321174 | 19239 | 108622 | At_100uM_ABA_Mutants_cDNA_P | −1.321545662 | −1 | − |
| 8161 | 12321174 | 1580012 | 20000441 | At_1uM_BR-BRZ_P | −2.735405149 | −1 | − |
| 8161 | 12321174 | 1580012 | 20000443 | At_1uM_BR-BRZ_P | −2.242959206 | −1 | − |
| 8161 | 12321174 | 19239 | 20000090 | At_2mM_SA_CS3726-Columbia_cDNA_P | 2.729191739 | 1 | + |
| 8161 | 12321174 | 19239 | 108668 | At_2mM_SA_cDNA_P | −1.508606549 | −1 | − |
| 8161 | 12321174 | 1580012 | 20000182 | At_2mM_SA_P | −1.704743738 | −1 | − |
| 8161 | 12321174 | 19239 | 20000111 | At_42deg_Heat_cDNA_P | −2.464590235 | −1 | − |
| 8161 | 12321174 | 19239 | 20000113 | At_42deg_Heat_cDNA_P | −1.876879573 | −1 | − |
| 8161 | 12321174 | 1580012 | 20000173 | At_42deg_Heat_P | −2.821092623 | −1 | − |
| 8161 | 12321174 | 1580012 | 20000213 | At_4deg_Cold_P | 4.599973491 | 1 | + |
| 8161 | 12321174 | 19239 | 108579 | At_4deg_Cold_cDNA_P | 3.707962628 | 1 | + |
| 8161 | 12321174 | 19239 | 108488 | At_50mM_NH4NO3_L-to-H_Rosette_cDNA_P | −1.429425437 | −1 | − |
| 8161 | 12321174 | 1580012 | 20001459 | At_50mM_NH4NO3_L-to-H_P | −2.78961071 | −1 | − |
| 8161 | 12321174 | 19239 | 108473 | At_Drought_Flowers_cDNA_P | 1.708925799 | 1 | + |
| 8161 | 12321174 | 1580012 | 20000437 | At_Drought_P | 4.822027774 | 1 | + |
| 8161 | 12321174 | 1580012 | 20001247 | At_Far-red-induction_P | −4.212204824 | −1 | − |
| 8161 | 12321174 | 1580012 | 20001248 | At_Far-red-induction_P | 6.169999757 | 1 | + |
| 8161 | 12321174 | 1580012 | 20001450 | At_Far-red-induction_P | 1.763281094 | 1 | + |
| 8161 | 12321174 | 1580012 | 20001451 | At_Far-red-induction_P | 1.395085228 | 1 | + |
| 8161 | 12321174 | 1580012 | 20000179 | At_Germinating_Seeds_P | −1.441537409 | −1 | − |
| 8161 | 12321174 | 1580012 | 20000180 | At_Germinating_Seeds_P | −3.147732829 | −1 | − |
| 8161 | 12321174 | 19239 | 108461 | At_Germinating_Seeds_cDNA_P | −1.646872266 | −1 | − |
| 8161 | 12321174 | 19239 | 108462 | At_Germinating_Seeds_cDNA_P | −1.665185357 | −1 | − |
| 8161 | 12321174 | 19239 | 108463 | At_Germinating_Seeds_cDNA_P | −1.426993122 | −1 | − |
| 8161 | 12321174 | 19239 | 108464 | At_Germinating_Seeds_cDNA_P | −1.828990435 | −1 | − |
| 8161 | 12321174 | 1580012 | 20000495 | At_Guard_Cells_P | −2.920579386 | −1 | − |
| 8161 | 12321174 | 19239 | 20000570 | At_Guard_Cells_cDNA_P | −1.49484136 | −1 | − |
| 8161 | 12321174 | 19239 | 107881 | At_Herbicide_v2_cDNA_P | −1.761216284 | −1 | − |
| 8161 | 12321174 | 19239 | 107891 | At_Herbicide_v2_cDNA_P | −2.164326634 | −1 | − |
| 8161 | 12321174 | 19239 | 108465 | At_Herbicide_v3_1_cDNA_P | 4.557494714 | 1 | + |
| 8161 | 12321174 | 19239 | 108629 | At_Herbicide_v3_1_cDNA_P | 1.998365625 | 1 | + |
| 8161 | 12321174 | 19239 | 108594 | At_Ler-rhl_Root_cDNA_P | 1.196805915 | 1 | + |
| 8161 | 12321174 | 1580012 | 20000264 | At_Open_Flower_P | −3.159834613 | −1 | − |
| 8161 | 12321174 | 1580012 | 20000265 | At_Open_Flower_P | −2.481345749 | −1 | − |
| 8161 | 12321174 | 1580012 | 20000286 | At_Open_Flower_P | −2.087635814 | −1 | − |
| 8161 | 12321174 | 1580012 | 20000794 | At_Petals_P | −1.300481698 | −1 | − |
| 8161 | 12321174 | 19239 | 108434 | At_Root_Tips_cDNA_P | −2.458487785 | −1 | − |
| 8161 | 12321174 | 1580012 | 20000185 | At_Roots_P | −5.279075251 | −1 | − |
| 8161 | 12321174 | 1580012 | 20000439 | At_Roots_P | −5.030661468 | −1 | − |
| 8161 | 12321174 | 19239 | 108480 | At_Shoot_Apices_cDNA_P | −2.309034231 | −1 | − |
| 8161 | 12321174 | 19239 | 108481 | At_Shoot_Apices_cDNA_P | −1.817142133 | −1 | − |
| 8161 | 12321174 | 1580012 | 20000184 | At_Shoots_P | −5.762449008 | −1 | − |
| 8161 | 12321174 | 1580012 | 20000438 | At_Shoots_P | −5.999883819 | −1 | − |

TABLE 10-continued

MA_DIFF TABLE
RESULTS FOR DIFFERENTIAL EXPRESSION ANALYSIS

| Clone | cDNA | Biomaterial | Expt_Rep_ID | Short_Name | Value (average log ratio) | Differential | Differential (+/−) |
|---|---|---|---|---|---|---|---|
| 8161 | 12321174 | 1580012 | 20000234 | At_Siliques_P | −3.209042334 | −1 | − |
| 8161 | 12321174 | 1580012 | 20000235 | At_Siliques_P | −3.022090865 | −1 | − |
| 8161 | 12321174 | 1580012 | 20000236 | At_Siliques_P | −2.340846461 | −1 | − |
| 8161 | 12321174 | 19239 | 108435 | At_stm_Mutants_cDNA_P | −2.665998172 | −1 | − |
| 8161 | 12321174 | 19239 | 108437 | At_Tissue_Specific_Expression_cDNA_P | −1.916511208 | −1 | − |
| 8161 | 12321174 | 19239 | 108438 | At_Tissue_Specific_Expression_cDNA_P | −1.518965097 | −1 | − |
| 8490 | 13491409 | 1580810 | 20000527 | At_10%_PEG_P | 1.554916476 | 1 | + |
| 8490 | 13491409 | 19237 | 20000070 | At_100uM_ABA_Mutants_cDNA_P | 5.066668574 | 1 | + |
| 8490 | 13491409 | 19237 | 20000072 | At_100uM_ABA_Mutants_cDNA_P | 4.640392336 | 1 | + |
| 8490 | 13491409 | 19237 | 20000086 | At_100uM_ABA_Mutants_cDNA_P | 3.798180577 | 1 | + |
| 8490 | 13491409 | 19237 | 20000087 | At_100uM_ABA_Mutants_cDNA_P | 3.425132193 | 1 | + |
| 8490 | 13491409 | 19237 | 20000088 | At_100uM_ABA_Mutants_cDNA_P | 3.271355571 | 1 | + |
| 8490 | 13491409 | 1580810 | 20000573 | At_100uM_ABA_Mutants_P | 1.433853789 | 1 | + |
| 8490 | 13491409 | 1580810 | 20000441 | At_1uM_BR-BRZ_P | −3.010706617 | −1 | − |
| 8490 | 13491409 | 1580810 | 20000443 | At_1uM_BR-BRZ_P | −2.748840687 | −1 | − |
| 8490 | 13491409 | 19237 | 20000090 | At_2mM_SA_CS3726-Columbia_cDNA_P | 3.600372905 | 1 | + |
| 8490 | 13491409 | 19237 | 20000111 | At_42deg_Heat_cDNA_P | −2.04796601 | −1 | − |
| 8490 | 13491409 | 1580810 | 20000171 | At_42deg_Heat_P | 1.514139809 | 1 | + |
| 8490 | 13491409 | 1580810 | 20000173 | At_42deg_Heat_P | −1.71925392 | −1 | − |
| 8490 | 13491409 | 1580810 | 20000213 | At_4deg_Cold_P | 2.813628804 | 1 | + |
| 8490 | 13491409 | 1580810 | 20001459 | At_50mM_NH4NO3_L-to-H_P | −1.715098188 | −1 | − |
| 8490 | 13491409 | 19237 | 108473 | At_Drought_Flowers_cDNA_P | 1.214971498 | 1 | + |
| 8490 | 13491409 | 1580810 | 20000437 | At_Drought_P | 4.220227281 | 1 | + |
| 8490 | 13491409 | 19237 | 20000638 | At_Drought_cDNA_P | 1.707634838 | 1 | + |
| 8490 | 13491409 | 1580810 | 20001247 | At_Far-red-induction_P | −4.634953394 | −1 | − |
| 8490 | 13491409 | 1580810 | 20001248 | At_Far-red-induction_P | 5.592598825 | 1 | + |
| 8490 | 13491409 | 1580810 | 20001450 | At_Far-red-induction_P | 1.649915315 | 1 | + |
| 8490 | 13491409 | 1580810 | 20000180 | At_Germinating_Seeds_P | −2.680555133 | −1 | − |
| 8490 | 13491409 | 19237 | 108461 | At_Germinating_Seeds_cDNA_P | −2.458568535 | −1 | − |
| 8490 | 13491409 | 19237 | 108462 | At_Germinating_Seeds_cDNA_P | −2.330805635 | −1 | − |
| 8490 | 13491409 | 19237 | 108463 | At_Germinating_Seeds_cDNA_P | −2.324720192 | −1 | − |
| 8490 | 13491409 | 19237 | 108464 | At_Germinating_Seeds_cDNA_P | −2.37426655 | −1 | − |
| 8490 | 13491409 | 1580810 | 20000495 | At_Guard_Cells_P | −3.247865708 | −1 | − |
| 8490 | 13491409 | 19237 | 107881 | At_Herbicide_v2_cDNA_P | −3.271686652 | −1 | − |
| 8490 | 13491409 | 19237 | 107891 | At_Herbicide_v2_cDNA_P | −2.602710336 | −1 | − |
| 8490 | 13491409 | 19237 | 108465 | At_Herbicide_v3_1_cDNA_P | 4.904232807 | 1 | + |
| 8490 | 13491409 | 19237 | 108629 | At_Herbicide_v3_1_cDNA_P | 1.945047545 | 1 | + |
| 8490 | 13491409 | 19237 | 108630 | At_Herbicide_v3_1_cDNA_P | 1.421005702 | 1 | + |
| 8490 | 13491409 | 1580810 | 20000264 | At_Open_Flower_P | −2.752089532 | −1 | − |
| 8490 | 13491409 | 19237 | 108434 | At_Root_Tips_cDNA_P | −2.359223661 | −1 | − |
| 8490 | 13491409 | 1580810 | 20000185 | At_Roots_P | −4.966099796 | −1 | − |
| 8490 | 13491409 | 1580810 | 20000439 | At_Roots_P | −4.736820319 | −1 | − |
| 8490 | 13491409 | 19237 | 108480 | At_Shoot_Apices_cDNA_P | −2.408359482 | −1 | − |
| 8490 | 13491409 | 19237 | 108481 | At_Shoot_Apices_cDNA_P | −3.133713759 | −1 | − |
| 8490 | 13491409 | 1580810 | 20000438 | At_Shoots_P | −4.72150623 | −1 | − |
| 8490 | 13491409 | 1580810 | 20000234 | At_Sillques_P | −2.874162085 | −1 | − |
| 8490 | 13491409 | 1580810 | 20000235 | At_Sillques_P | −2.246390758 | −1 | − |
| 8490 | 13491409 | 1580810 | 20000236 | At_Sillques_P | −2.46053553 | −1 | − |
| 8490 | 13491409 | 19237 | 108435 | At_stm_Mutants_cDNA_P | −2.551559281 | −1 | − |
| 8490 | 13491409 | 19237 | 108429 | At_Tissue_Specific_Expression_cDNA_P | −1.022462895 | −1 | − |
| 8490 | 13491409 | 19237 | 108437 | At_Tissue_Specific_Expression_cDNA_P | −1.501818945 | −1 | − |
| 8490 | 13491409 | 19237 | 108438 | At_Tissue_Specific_Expression_cDNA_P | −1.739999423 | −1 | − |
| 8490 | 13491409 | 1609791 | 108439 | At_Tissue_Specific_Expression_cDNA_P | −2.657664047 | −1 | − |
| 305463 | 12355477 | 1609791 | 20000478 | Zm_5mM_SA_P | 1.626535585 | 1 | + |
| 305463 | 12355477 | 1609791 | 20000629 | Zm_Herbicide-Treaments_P | 1.058894478 | 1 | + |
| 305463 | 12355477 | 1609791 | 20000493 | Zm_Hybrid_Seed_Dev_P | 1.987652422 | 1 | + |
| 305463 | 12355477 | 1609791 | 108543 | Zm_Imbibed_Embryo_Endosperm_P | −1.733891996 | −1 | − |
| 305463 | 12355477 | 1609791 | 108528 | Zm_Imbibed_Seeds_P | 1.608201864 | 1 | + |
| 305463 | 12355477 | 1609791 | 108530 | Zm_Imbibed_Seeds_P | 1.26990335 | 1 | + |
| 305463 | 12355477 | 1608109 | 108546 | Zm_Imbibed_Seeds_P | 1.460500636 | 1 | + |
| 486033 | 12436299 | 1608109 | 20000530 | Zm_2-4D_P | 1.265765889 | 1 | + |
| 486033 | 12436299 | 1608109 | 108523 | Zm_42deg_Heat_P | −1.154793559 | −1 | − |
| 486033 | 12436299 | 1608109 | 108687 | Zm_Embryos_Flowers_P | 1.691512498 | 1 | + |
| 486033 | 12436299 | 1608109 | 108688 | Zm_Embryos_Flowers_P | −2.071866621 | −1 | − |

What is claimed is:

1. A method of modulating the flowering time or size of a plant, or the size or number of rosette leaves of a plant comprising transforming a plant cell with a nucleic acid molecule which encodes an amino acid sequence exhibiting at least 95% sequence identity to SEQ ID NO:36; generating from said plant cell a transformed plant in which said nucleic acid molecule is overexpressed; and selecting from a plurality of said transformed plants a plant having at least one trait selected from the group consisting of delayed flowering time, an increase in plant height, an increase in inflorescence size, an increase in inflorescence thickness, an increase in the size of the rosette and an increase in rosette leaf number as compared to a control plant that does not comprise said nucleic acid molecule.

2. A method of increasing the size of a plant comprising transforming a plant cell with a nucleic acid molecule which encodes an amino acid sequence exhibiting at least 95% sequence identity to SEQ ID NO:36; generating from said plant cell a transformed plant in which said nucleic acid molecule is overexpressed;
and selecting from a plurality of said transformed plants a plant having at least one trait selected from the group consisting of an increase in plant height, an increase in inflorescence size, an increase in inflorescence thickness, an increase in the size of the rosette and an increase in rosette leaf number as compared to a control plant that does not comprise said nucleic acid molecule.

3. A method of increasing the size or number of rosette leaves of a plant comprising transforming a plant with a nucleic acid molecule which encodes an amino acid sequence exhibiting at least 95% sequence identity to SEQ ID NO:36; generating from said plant cell a transformed plant in which said nucleic acid molecule is overexpressed; and selecting from a plurality of said transformed plants a plant having at least one trait selected from the group consisting of an increase in the size of the rosette leaves and an increase in rosette leaf number as compared to a control plant that does not comprise said nucleic acid molecule.

4. A plant, plant cell, plant material or seed of a plant obtained according to the method of claim 1, wherein said plant, plant cell, plant material or plant seed contains the nucleic acid molecule which encodes an amino acid sequence exhibiting at least 95% sequence identity to SEQ ID NO:36.

5. A plant, plant cell, plant material or seed of a plant obtained according to the method of claim 2, wherein said plant, plant cell, plant material or plant seed contains the nucleic acid molecule which encodes an amino acid sequence exhibiting at least 95% sequence identity to SEQ ID NO:36.

6. A plant, plant cell, plant material or seed of a plant obtained according to the method of claim 3, wherein said plant, plant cell, plant material or plant seed contains the nucleic acid molecule which encodes an amino acid sequence exhibiting at least 95% sequence identity to SEQ ID NO:36.

7. The method according to any one of claims 1-3, wherein said nucleic acid molecule encodes SEQ ID NO:36.

8. The method according to any one of claims 1-3, wherein said nucleic acid molecule is SEQ ID NO:35.

9. The plant, plant cell, plant material or seed of a plant according to any one of claims 4-6, wherein said nucleic acid molecule encodes SEQ ID NO:36.

* * * * *

SEQUENCE LISTING

<160> NUMBER OF SEQ ID NOS: 50

<210> SEQ ID NO 1
<211> LENGTH: 1453
<212> TYPE: DNA
<213> ORGANISM: Zea mays subsp. mays
<220> FEATURE:
<221> NAME/KEY: misc_feature
<222> LOCATION: (1)..(1453)
<223> OTHER INFORMATION: ceres Seq. ID no. 12355477

<400> SEQUENCE: 1

| | | |
|---|---|---|
| aatccctcgc ctgcaactgg ctctctgtcc ccttctgctc ccccacggt tccccagagc | 60 |
| ccgagccaaa tctaggggct tccttcatcc gagcgtggtt tcaattctag gggtagtcac | 120 |
| ctcacctgaa ttccgcccaa ataaattcgt cgctgccttg tgatccttgg ggtttccttg | 180 |
| gttcttgagt tgcgatcttc tgctggttcg tgtcccccaa tccgtaatca atccggcgtc | 240 |
| taggaaacca attgctgctc agttctctta tttgctcctc gccttccttc ctccagcctg | 300 |
| gttaaaatat cgaaggggga ttttttttta aaaatctgct catcgaggaa cagggaaga | 360 |
| caagaattgt tgcatcggat aaaggtcggg tgaaaataca agcaaatcct gggaactcgc | 420 |
| gtcccttgc taggtggttc tttcctgata caaagaacac aatgggcgat gtgtccttga | 480 |
| acggacccat taaggctgct gagccaggtg ccggtggcat tgccaagggc aatcaagttc | 540 |
| tggacacgat gtccgccggg tggacagacg agagacacag gctgtatata agctctatgg | 600 |
| aggcctcttt cgtcgatcaa ctgtacaacc acgggagccg tccgcgcaac gcaaacggca | 660 |
| ccgccttcaa ggctctccgc agggagtacg tcgagtatga aagaccgat gctcctgtgc | 720 |
| gaaggggggc taagtgctgc ggcgttcctg caaatccttg gatgcagcat ttcaggccac | 780 |
| gtagtgatgg cggtaataac gcgcgaggcg atgggctcgg ggattctgtg ggcgatcttg | 840 |
| aatctggcac tgaggcaaac cggaagagcc tctcagcgtc tcatggaagg gaacgggacg | 900 |
| cttgtgaggg agaaccccag cttctccatg aaagtagaga ggtctctgat caaaattttg | 960 |
| ctgacgacga ggctgaagct gaaacagaat caatgaaagc atacaagaaa aggagattaa | 1020 |
| gcaggacaat gatcaactaa atttgcaggg tcaattagct tagcctgttg caggaattga | 1080 |
| gatgactgtc ctaaaaggag gcagtaagat gatgggacat gtcttacgaa attttcagct | 1140 |
| gttgcctctt ggtagccaag gcactttgaa tccgaaggaa ggtgttgaag ggtagttgtt | 1200 |
| agtgatcttg tgatgatata acgagctctg gagcagttag catcggcatt ttagtggatt | 1260 |
| atgttcttgt tatgtgtatc tgtctatttt tcagtcctca tcggtagtgc tgcatagtac | 1320 |
| ctcgctctct cgtcagaagg atattaggct aggtcactgt tattaaattt ttcaataaca | 1380 |
| gtgaagtgta catgtgtttg ccaaatggtg agaatcatta ttgatttcca attcacaaac | 1440 |
| tattctttat gcc | 1453 |

<210> SEQ ID NO 2
<211> LENGTH: 576
<212> TYPE: DNA
<213> ORGANISM: Zea mays subsp. mays

<400> SEQUENCE: 2

| | | |
|---|---|---|
| atgggcgatg tgtccttgaa cggacccatt aaggctgctg agccaggtgc cggtggcatt | 60 |
| gccaagggca atcaagttct ggacacgatg tccgccgggt ggacagacga gagacacagg | 120 |
| ctgtatataa gctctatgga ggcctctttc gtcgatcaac tgtacaacca cgggagccgt | 180 |

```
ccgcgcaacg caaacggcac cgccttcaag gctctccgca gggagtacgt cgagtatgag    240
aagaccgatg ctcctgtgcg aagggggct aagtgctgcg gcgttcctgc aaatccttgg     300
atgcagcatt tcaggccacg tagtgatggc ggtaataacg cgcgaggcga tgggctcggg    360
gattctgtgg gcgatcttga atctggcact gaggcaaacc ggaagagcct ctcagcgtct    420
catggaaggg aacgggacgc ttgtgaggga aaccccagc ttctccatga agtagagag      480 gtctctgatc aaattttgc tgacgacgag gctgaagctg aaacagaatc aatgaaagca    540
tacaagaaaa ggagattaag caggacaatg atcaac                             576
```

<210> SEQ ID NO 3
<211> LENGTH: 192
<212> TYPE: PRT
<213> ORGANISM: Zea mays subsp. mays
<220> FEATURE:
<221> NAME/KEY: peptide
<222> LOCATION: (1)..(192)
<223> OTHER INFORMATION: ceres Seq. ID no. 12355478

<400> SEQUENCE: 3

```
Met Gly Asp Val Ser Leu Asn Gly Pro Ile Lys Ala Ala Glu Pro Gly
1               5                   10                  15

Ala Gly Gly Ile Ala Lys Gly Asn Gln Val Leu Asp Thr Met Ser Ala
            20                  25                  30

Gly Trp Thr Asp Glu Arg His Arg Leu Tyr Ile Ser Ser Met Glu Ala
        35                  40                  45

Ser Phe Val Asp Gln Leu Tyr Asn His Gly Ser Arg Pro Arg Asn Ala
    50                  55                  60

Asn Gly Thr Ala Phe Lys Ala Leu Arg Arg Glu Tyr Val Glu Tyr Glu
65                  70                  75                  80

Lys Thr Asp Ala Pro Val Arg Arg Gly Ala Lys Cys Cys Gly Val Pro
                85                  90                  95

Ala Asn Pro Trp Met Gln His Phe Arg Pro Arg Ser Asp Gly Gly Asn
            100                 105                 110

Asn Ala Arg Gly Asp Gly Leu Gly Asp Ser Val Gly Asp Leu Glu Ser
        115                 120                 125

Gly Thr Glu Ala Asn Arg Lys Ser Leu Ser Ala Ser His Gly Arg Glu
    130                 135                 140

Arg Asp Ala Cys Glu Gly Glu Pro Gln Leu Leu His Glu Ser Arg Glu
145                 150                 155                 160

Val Ser Asp Gln Asn Phe Ala Asp Asp Glu Ala Glu Ala Glu Thr Glu
                165                 170                 175

Ser Met Lys Ala Tyr Lys Lys Arg Arg Leu Ser Arg Thr Met Ile Asn
            180                 185                 190
```

<210> SEQ ID NO 4
<211> LENGTH: 489
<212> TYPE: DNA
<213> ORGANISM: Zea mays subsp. mays

<400> SEQUENCE: 4

```
atgtccgccg ggtggacaga cgagagacac aggctgtata taagctctat ggaggcctct    60
ttcgtcgatc aactgtacaa ccacgggagc cgtccgcgca acgcaaacgg caccgccttc   120
aaggctctcc gcaggagta cgtcgagtat gagaagaccg atgctcctgt gcgaaggggg    180
gctaagtgct gcggcgttcc tgcaaatcct tggatgcagc atttcaggcc acgtagtgat   240
ggcggtaata acgcgcgagg cgatgggctc gggattctg tgggcgatct tgaatctggc    300
```

```
actgaggcaa accggaagag cctctcagcg tctcatggaa gggaacggga cgcttgtgag    360
ggagaacccc agcttctcca tgaaagtaga gaggtctctg atcaaaattt tgctgacgac    420
gaggctgaag ctgaaacaga atcaatgaaa gcatacaaga aaaggagatt aagcaggaca    480
atgatcaac                                                            489
```

<210> SEQ ID NO 5
<211> LENGTH: 163
<212> TYPE: PRT
<213> ORGANISM: Zea mays subsp. mays
<220> FEATURE:
<221> NAME/KEY: peptide
<222> LOCATION: (1)..(163)
<223> OTHER INFORMATION: ceres Seq. ID no. 12355479

<400> SEQUENCE: 5

```
Met Ser Ala Gly Trp Thr Asp Glu Arg His Arg Leu Tyr Ile Ser Ser
1               5                   10                  15

Met Glu Ala Ser Phe Val Asp Gln Leu Tyr Asn His Gly Ser Arg Pro
            20                  25                  30

Arg Asn Ala Asn Gly Thr Ala Phe Lys Ala Leu Arg Arg Glu Tyr Val
        35                  40                  45

Glu Tyr Glu Lys Thr Asp Ala Pro Val Arg Arg Gly Ala Lys Cys Cys
    50                  55                  60

Gly Val Pro Ala Asn Pro Trp Met Gln His Phe Arg Pro Arg Ser Asp
65                  70                  75                  80

Gly Gly Asn Asn Ala Arg Gly Asp Gly Leu Gly Asp Ser Val Gly Asp
                85                  90                  95

Leu Glu Ser Gly Thr Glu Ala Asn Arg Lys Ser Leu Ser Ala Ser His
            100                 105                 110

Gly Arg Glu Arg Asp Ala Cys Glu Gly Glu Pro Gln Leu Leu His Glu
        115                 120                 125

Ser Arg Glu Val Ser Asp Gln Asn Phe Ala Asp Asp Glu Ala Glu Ala
    130                 135                 140

Glu Thr Glu Ser Met Lys Ala Tyr Lys Lys Arg Arg Leu Ser Arg Thr
145                 150                 155                 160

Met Ile Asn
```

<210> SEQ ID NO 6
<211> LENGTH: 441
<212> TYPE: DNA
<213> ORGANISM: Zea mays subsp. mays

<400> SEQUENCE: 6

```
atggaggcct ctttcgtcga tcaactgtac aaccacggga gccgtccgcg caacgcaaac     60
ggcaccgcct tcaaggctct ccgcagggag tacgtcgagt atgagaagac cgatgctcct    120
gtgcgaaggg gggctaagtg ctgcggcgtt cctgcaaatc cttggatgca gcatttcagg    180
ccacgtagtg atggcggtaa taacgcgcga ggcgatgggc tcggggattc tgtgggcgat    240
cttgaatctg gcactgaggc aaaccggaag agcctctcag cgtctcatgg aagggaacgg    300
gacgcttgtg agggagaacc ccagcttctc catgaaagta gagaggtctc tgatcaaaat    360
tttgctgacg acgaggctga agctgaaaca gaatcaatga agcatacaa gaaaggaga    420 ttaagcagga caatgatcaa c                                              441
```

```
<210> SEQ ID NO 7
<211> LENGTH: 147
<212> TYPE: PRT
<213> ORGANISM: Zea mays subsp. mays
<220> FEATURE:
<221> NAME/KEY: peptide
<222> LOCATION: (1)..(147)
<223> OTHER INFORMATION: ceres Seq. ID no. 12355480

<400> SEQUENCE: 7

Met Glu Ala Ser Phe Val Asp Gln Leu Tyr Asn His Gly Ser Arg Pro
1               5                   10                  15

Arg Asn Ala Asn Gly Thr Ala Phe Lys Ala Leu Arg Arg Glu Tyr Val
            20                  25                  30

Glu Tyr Glu Lys Thr Asp Ala Pro Val Arg Arg Gly Ala Lys Cys Cys
        35                  40                  45

Gly Val Pro Ala Asn Pro Trp Met Gln His Phe Arg Pro Arg Ser Asp
    50                  55                  60

Gly Gly Asn Asn Ala Arg Gly Asp Gly Leu Gly Asp Ser Val Gly Asp
65                  70                  75                  80

Leu Glu Ser Gly Thr Glu Ala Asn Arg Lys Ser Leu Ser Ala Ser His
                85                  90                  95

Gly Arg Glu Arg Asp Ala Cys Glu Gly Glu Pro Gln Leu Leu His Glu
            100                 105                 110

Ser Arg Glu Val Ser Asp Gln Asn Phe Ala Asp Glu Ala Glu Ala
        115                 120                 125

Glu Thr Glu Ser Met Lys Ala Tyr Lys Lys Arg Arg Leu Ser Arg Thr
    130                 135                 140

Met Ile Asn
145

<210> SEQ ID NO 8
<211> LENGTH: 1494
<212> TYPE: DNA
<213> ORGANISM: Zea mays subsp. mays
<220> FEATURE:
<221> NAME/KEY: misc_feature
<222> LOCATION: (1)..(1494)
<223> OTHER INFORMATION: ceres Seq. ID no. 12410516

<400> SEQUENCE: 8
gtgtttcatt tttaatgacc attctctcat ctgctgctgg ctgcggctat ataccccct      60 ctctctgtct ctctatctcc ttctgttctt agacgtttct ccatagcctg agccaaatct   120
agggggcttg cttcatctgc tgtccgatcg tggtttggtt tctcggggct ggcgcggtca   180
agagcgcacc tgaattccac cgaaatccgc cacggtagtt cttgcctagg tgtgtcgttg   240
gtcgttgcct tgtgaccctt gcggattttc ttgtttcttt ttgagttgcg atctttgcag   300
gttagtctcc cccccaatcc gtaatcatcc ggcgtctagg aaactgcagt ccagtttct    360 tatttgttcg tctcgtgcct tctccccatc ctggttagaa agaatatcgg aaggggatt    420 ttttttttg cctgttcgta gaggaagcag tgaagacata attgttgcat ctgataaagc    480
tcgggcgaaa tacacgcaaa tccttggaat tttgcatccc tttgctggct cttttctgat   540
tcagagaacc caatggggga tgtgtccttg aatcgacccg ttaaggccga gccaactgcc   600
ggtggcattg ccaaggaaaa ccgagttctg acacgatgt ccgccgggtg gacggacgag    660
agacacatgc tgtatataag ctccatggag gcttcttttg tcgatcagct atacaaccat   720
ggaaaccatc cgcacgacgc aaatggcgct ggcttcaagg ttctccgcag gggggtgtgg   780
gagtacatcg agtatgagaa gaccagtgcc cctgtgcgaa gtggggctaa atgctgcgtc   840
```

```
cctgcaaatc cttggatccg gcatttcagg ccacgtgact gcggtagtaa cgcacagagt    900
gacgcggtcg aggcctcagt gggcgaccat gagtcgggta ctcaggcaag ccgcaagagc    960
ccttcagtgt ctcatggaag ggaacgggga gcttgtaagg gagaacccca gattctacat   1020
gaaagtacag aggtctctga tcaaaatttt gctgacgatg aggctgaagc tgaaacagaa   1080
tcaatgaaag catgcaagaa aaggagacta agcagggctt tgcactccgg tgctgaatga   1140
tcaagtaaat tcgcaggaac aattagctta gcctgttgca agaatcgata tgatttatcc   1200
taaaagaagg tgttaagatg atgggacatg gctttcaaaa ctttcagctg ttgcctgctg   1260
gtagccaaga cacactgaat ccgaaggaag gcgttaaggg tagctgtta gtgattttgt    1320 gatataaaga gtactggggc agttagcatc ggcattttta gcggatttaa gttcttgtta   1380
tgtatatctg tcttctgtct tcatcagtag tgctgcttag tacctcactc tctcgtcagc   1440
aggatatttc tatatattgt ctgtacttgg tagatatatg tattggttga tccg          1494

<210> SEQ ID NO 9
<211> LENGTH: 585
<212> TYPE: DNA
<213> ORGANISM: Zea mays subsp. mays

<400> SEQUENCE: 9
atgggggatg tgtccttgaa tcgacccgtt aaggccgagc caactgccgg tggcattgcc     60
aagggaaacc gagttctgga cacgatgtcc gccgggtgga cggacgagag acacatgctg    120
tatataagct ccatggaggc ttctttttgtc gatcagctat acaaccatgg aaaccatccg    180
cacgacgcaa atggcgctgg cttcaaggtt ctccgcaggg gggtgtggga gtacatcgag    240
tatgagaaga ccagtgcccc tgtgcgaagt ggggctaaat gctgcgtccc tgcaaatcct    300
tggatccggc atttcaggcc acgtgactgc ggtagtaacg cacagagtga cgcggtcgag    360
gcctcagtgg gcgaccatga gtcgggtact caggcaagcc gcaagagccc ttcagtgtct    420 catgaaggg acggggagc ttgtaaggga gaaccccaga ttctacatga agtacagag     480 gtctctgatc aaaattttgc tgacgatgag gctgaagctg aaacagaatc aatgaaagca    540
tgcaagaaaa ggagactaag cagggctttg cactccggtg ctgaa                    585

<210> SEQ ID NO 10
<211> LENGTH: 195
<212> TYPE: PRT
<213> ORGANISM: Zea mays subsp. mays
<220> FEATURE:
<221> NAME/KEY: peptide
<222> LOCATION: (1)..(195)
<223> OTHER INFORMATION: ceres Seq. ID no. 12410517

<400> SEQUENCE: 10

Met Gly Asp Val Ser Leu Asn Arg Pro Val Lys Ala Glu Pro Thr Ala
1               5                   10                  15

Gly Gly Ile Ala Lys Gly Asn Arg Val Leu Asp Thr Met Ser Ala Gly
            20                  25                  30

Trp Thr Asp Glu Arg His Met Leu Tyr Ile Ser Ser Met Glu Ala Ser
        35                  40                  45

Phe Val Asp Gln Leu Tyr Asn His Gly Asn His Pro His Asp Ala Asn
    50                  55                  60

Gly Ala Gly Phe Lys Val Leu Arg Arg Gly Val Trp Glu Tyr Ile Glu
65                  70                  75                  80

Tyr Glu Lys Thr Ser Ala Pro Val Arg Ser Gly Ala Lys Cys Cys Val
                85                  90                  95
```

```
Pro Ala Asn Pro Trp Ile Arg His Phe Arg Pro Arg Asp Cys Gly Ser
                100                 105                 110

Asn Ala Gln Ser Asp Ala Val Glu Ala Ser Val Gly Asp His Glu Ser
            115                 120                 125

Gly Thr Gln Ala Ser Arg Lys Ser Pro Ser Val Ser His Gly Arg Glu
        130                 135                 140

Arg Gly Ala Cys Lys Gly Glu Pro Gln Ile Leu His Glu Ser Thr Glu
145                 150                 155                 160

Val Ser Asp Gln Asn Phe Ala Asp Asp Glu Ala Glu Ala Glu Thr Glu
                165                 170                 175

Ser Met Lys Ala Cys Lys Lys Arg Arg Leu Ser Arg Ala Leu His Ser
            180                 185                 190

Gly Ala Glu
        195

<210> SEQ ID NO 11
<211> LENGTH: 501
<212> TYPE: DNA
<213> ORGANISM: Zea mays subsp. mays

<400> SEQUENCE: 11
atgtccgccg gtggacgga cgagagacac atgctgtata taagctccat ggaggcttct    60
tttgtcgatc agctatacaa ccatggaaac catccgcacg acgcaaatgg cgctggcttc   120
aaggttctcc gcaggggggt gtgggagtac atcgagtatg agaagaccag tgcccctgtg   180
cgaagtgggg ctaaatgctg cgtccctgca atccttgga tccggcattt caggccacgt    240
gactgcggta gtaacgcaca gagtgacgcg gtcgaggcct cagtgggcga ccatgagtcg   300
ggtactcagg caagccgcaa gagcccttca gtgtctcatg gagggaacg gggagcttgt   360 aagggagaac cccagattct acatgaaagt acagaggtct ctgatcaaaa ttttgctgac   420
gatgaggctg aagctgaaac agaatcaatg aaagcatgca agaaaaggag actaagcagg   480
gctttgcact ccggtgctga a                                            501

<210> SEQ ID NO 12
<211> LENGTH: 167
<212> TYPE: PRT
<213> ORGANISM: Zea mays subsp. mays
<220> FEATURE:
<221> NAME/KEY: peptide
<222> LOCATION: (1)..(167)
<223> OTHER INFORMATION: ceres Seq. ID no. 12410518

<400> SEQUENCE: 12

Met Ser Ala Gly Trp Thr Asp Glu Arg His Met Leu Tyr Ile Ser Ser
1               5                   10                  15

Met Glu Ala Ser Phe Val Asp Gln Leu Tyr Asn His Gly Asn His Pro
            20                  25                  30

His Asp Ala Asn Gly Ala Gly Phe Lys Val Leu Arg Arg Gly Val Trp
        35                  40                  45

Glu Tyr Ile Glu Tyr Glu Lys Thr Ser Ala Pro Val Arg Ser Gly Ala
    50                  55                  60

Lys Cys Cys Val Pro Ala Asn Pro Trp Ile Arg His Phe Arg Pro Arg
65                  70                  75                  80

Asp Cys Gly Ser Asn Ala Gln Ser Asp Ala Val Glu Ala Ser Val Gly
                85                  90                  95

Asp His Glu Ser Gly Thr Gln Ala Ser Arg Lys Ser Pro Ser Val Ser
            100                 105                 110
```

His Gly Arg Glu Arg Gly Ala Cys Lys Gly Glu Pro Gln Ile Leu His
            115                 120                 125

Glu Ser Thr Glu Val Ser Asp Gln Asn Phe Ala Asp Asp Glu Ala Glu
        130                 135                 140

Ala Glu Thr Glu Ser Met Lys Ala Cys Lys Lys Arg Arg Leu Ser Arg
145                 150                 155                 160

Ala Leu His Ser Gly Ala Glu
                165

<210> SEQ ID NO 13
<211> LENGTH: 471
<212> TYPE: DNA
<213> ORGANISM: Zea mays subsp. mays

<400> SEQUENCE: 13

```
atgctgtata taagctccat ggaggcttct tttgtcgatc agctatacaa ccatggaaac      60
catccgcacg acgcaaatgg cgctggcttc aaggttctcc gcagggggt gtgggagtac      120 atcgagtatg agaagaccag tgcccctgtg cgaagtgggg ctaaatgctg cgtccctgca     180
aatccttgga tccggcattt caggccacgt gactgcggta gtaacgcaca gagtgacgcg     240
gtcgaggcct cagtgggcga ccatgagtcg ggtactcagg caagccgcaa gagcccttca     300
gtgtctcatg aagggaacg gggagcttgt aagggagaac cccagattct acatgaaagt     360
acagaggtct ctgatcaaaa ttttgctgac gatgaggctg aagctgaaac agaatcaatg     420
aaagcatgca agaaaaggag actaagcagg gctttgcact ccggtgctga a              471
```

<210> SEQ ID NO 14
<211> LENGTH: 157
<212> TYPE: PRT
<213> ORGANISM: Zea mays subsp. mays
<220> FEATURE:
<221> NAME/KEY: peptide
<222> LOCATION: (1)..(157)
<223> OTHER INFORMATION: ceres Seq. ID no. 12410519

<400> SEQUENCE: 14

Met Leu Tyr Ile Ser Ser Met Glu Ala Ser Phe Val Asp Gln Leu Tyr
1               5                   10                  15

Asn His Gly Asn His Pro His Asp Ala Asn Gly Ala Gly Phe Lys Val
            20                  25                  30

Leu Arg Arg Gly Val Trp Glu Tyr Ile Glu Tyr Glu Lys Thr Ser Ala
        35                  40                  45

Pro Val Arg Ser Gly Ala Lys Cys Cys Val Pro Ala Asn Pro Trp Ile
    50                  55                  60

Arg His Phe Arg Pro Arg Asp Cys Gly Ser Asn Ala Gln Ser Asp Ala
65                  70                  75                  80

Val Glu Ala Ser Val Gly Asp His Glu Ser Gly Thr Gln Ala Ser Arg
                85                  90                  95

Lys Ser Pro Ser Val Ser His Gly Arg Glu Arg Gly Ala Cys Lys Gly
            100                 105                 110

Glu Pro Gln Ile Leu His Glu Ser Thr Glu Val Ser Asp Gln Asn Phe
        115                 120                 125

Ala Asp Asp Glu Ala Glu Ala Glu Thr Glu Ser Met Lys Ala Cys Lys
    130                 135                 140

Lys Arg Arg Leu Ser Arg Ala Leu His Ser Gly Ala Glu
145                 150                 155

<210> SEQ ID NO 15
<211> LENGTH: 409
<212> TYPE: DNA
<213> ORGANISM: Brassica napus
<220> FEATURE:
<221> NAME/KEY: misc_feature
<222> LOCATION: (1)..(409)
<223> OTHER INFORMATION: ceres Seq. ID no. 4788142

<400> SEQUENCE: 15

```
tttttttcttt tcaccttct cctcctcctt ctctcctttc ttctgatatt ttcctctctc      60
tagtcttaac aagatagata ggtagcaaat ggttggtgac tacagagaga actatagccc     120
aagctccgac gattcttctt ctgtagggga agagacgact tcttcaatgt attctgcgag     180
gaatgaagat acgcctacag aatggaccga tgagaagcat agtttgtatc ttaaatcaat     240
ggaagcttcc ttcgttgatc agctgtacaa ctccctcggt gcgctcggct ccaaaaacaa     300
caaggatact gtcggaccat cgagaaggtt cggtgatggt ggaaaaacctt ctgaagaaca     360 ggtatgaata ggacactttc ccctgtcttt ttccatgtgc gatgttgtg                409
```

<210> SEQ ID NO 16
<211> LENGTH: 276
<212> TYPE: DNA
<213> ORGANISM: Brassica napus

<400> SEQUENCE: 16

```
atggttggtg actacagaga gaactatagc ccaagctccg acgattcttc ttctgtaggg      60
gaagagacga cttcttcaat gtattctgcg aggaatgaag atacgcctac agaatggacc     120
gatgagaagc atagtttgta tcttaaatca atggaagctt ccttcgttga tcagctgtac     180
aactccctcg gtgcgctcgg ctccaaaaac aacaaggata ctgtcggacc atcgagaagg     240
ttcggtgatg gtggaaaaac cttctgaaga acaggta                              276
```

<210> SEQ ID NO 17
<211> LENGTH: 92
<212> TYPE: PRT
<213> ORGANISM: Brassica napus
<220> FEATURE:
<221> NAME/KEY: peptide
<222> LOCATION: (1)..(92)
<223> OTHER INFORMATION: ceres Seq. ID no. 4788143

<400> SEQUENCE: 17

```
Met Val Gly Asp Tyr Arg Glu Asn Tyr Ser Pro Ser Ser Asp Asp Ser
  1               5                  10                  15

Ser Ser Val Gly Glu Glu Thr Thr Ser Ser Met Tyr Ser Ala Arg Asn
                 20                  25                  30

Glu Asp Thr Pro Thr Glu Trp Thr Asp Glu Lys His Ser Leu Tyr Leu
             35                  40                  45

Lys Ser Met Glu Ala Ser Phe Val Asp Gln Leu Tyr Asn Ser Leu Gly
         50                  55                  60

Ala Leu Gly Ser Lys Asn Asn Lys Asp Thr Val Gly Pro Ser Arg Arg
 65                  70                  75                  80

Phe Gly Asp Gly Gly Lys Pro Ser Glu Glu Gln Val
                 85                  90
```

<210> SEQ ID NO 18
<211> LENGTH: 198
<212> TYPE: DNA
<213> ORGANISM: Brassica napus -continued

<400> SEQUENCE: 18

```
atgtattctg cgaggaatga agatacgcct acagaatgga ccgatgagaa gcatagtttg    60
tatcttaaat caatggaagc ttccttcgtt gatcagctgt acaactccct cggtgcgctc   120
ggctccaaaa acaacaagga tactgtcgga ccatcgagaa ggttcggtga tggtggaaaa   180
ccttctgaag aacaggta                                                 198
```

<210> SEQ ID NO 19
<211> LENGTH: 66
<212> TYPE: PRT
<213> ORGANISM: Brassica napus
<220> FEATURE:
<221> NAME/KEY: peptide
<222> LOCATION: (1)..(66)
<223> OTHER INFORMATION: ceres Seq. ID no. 4788144

<400> SEQUENCE: 19

Met Tyr Ser Ala Arg Asn Glu Asp Thr Pro Thr Glu Trp Thr Asp Glu
1               5                   10                  15

Lys His Ser Leu Tyr Leu Lys Ser Met Glu Ala Ser Phe Val Asp Gln
            20                  25                  30

Leu Tyr Asn Ser Leu Gly Ala Leu Gly Ser Lys Asn Asn Lys Asp Thr
        35                  40                  45

Val Gly Pro Ser Arg Arg Phe Gly Asp Gly Gly Lys Pro Ser Glu Glu
    50                  55                  60

Gln Val
65

<210> SEQ ID NO 20
<211> LENGTH: 186
<212> TYPE: DNA
<213> ORGANISM: Brassica napus

<400> SEQUENCE: 20

```
atgaagatac gcctacagaa tggaccgatg agaagcatag tttgtatctt aaatcaatgg    60
aagcttcctt cgttgatcag ctgtacaact ccctcggtgc gctcggctcc aaaaacaaca   120
aggatactgt cggaccatcg agaaggttcg gtgatggtgg aaaaccttct gaagaacagg   180
tatgaa                                                              186
```

<210> SEQ ID NO 21
<211> LENGTH: 62
<212> TYPE: PRT
<213> ORGANISM: Brassica napus
<220> FEATURE:
<221> NAME/KEY: peptide
<222> LOCATION: (1)..(62)
<223> OTHER INFORMATION: ceres Seq. ID no. 4788145

<400> SEQUENCE: 21

Met Lys Ile Arg Leu Gln Asn Gly Pro Met Arg Ser Ile Val Cys Ile
1               5                   10                  15

Leu Asn Gln Trp Lys Leu Pro Ser Leu Ile Ser Cys Thr Thr Pro Ser
            20                  25                  30

Val Arg Ser Ala Pro Lys Thr Thr Arg Ile Leu Ser Asp His Arg Glu
        35                  40                  45

Gly Ser Val Met Val Glu Asn Leu Leu Lys Asn Arg Tyr Glu
    50                  55                  60

<210> SEQ ID NO 22
<211> LENGTH: 486
<212> TYPE: DNA
<213> ORGANISM: Brassica napus
<220> FEATURE:
<221> NAME/KEY: misc_feature
<222> LOCATION: (1)..(486)
<223> OTHER INFORMATION: ceres Seq. ID no. 4796909

<400> SEQUENCE: 22

```
tttccgtctt tcttttcac cttctcctcc tccttctctc ctttcttctg atatttcct      60
ctctctagtc ttaacaagat agataggtag caaatggttg gtgactacag agagaactat   120
agcccaagct ccgacgattc ttcttctgta ggggaagaga cgacttcttc aatgtattct   180
gcgaggaatg aagatacgcc tacagaatgg accgatgaga agcatagttt gtatcttaaa   240
tcaatggaag cttccttcgt tgatcagctg tacaactccc tcggtgcgct cggctccaaa   300
aacaacaagg atactgtcgg accatcgaga aggttcggtg atggtggaaa accttctgaa   360
gaacagaaga tgaatgtgag gcagcctgag tatcgtctca atggaagaca cggtcgtcgc   420
tctcacgagt ttcttaggag tccatggatc aagcactata agccttcacc aaagtcccta   480
acagat                                                              486
```

<210> SEQ ID NO 23
<211> LENGTH: 393
<212> TYPE: DNA
<213> ORGANISM: Brassica napus

<400> SEQUENCE: 23

```
atggttggtg actacagaga gaactatagc ccaagctccg acgattcttc ttctgtaggg    60
gaagagacga cttcttcaat gtattctgcg aggaatgaag atacgcctac agaatggacc   120
gatgagaagc atagtttgta tcttaaatca atggaagctt ccttcgttga tcagctgtac   180
aactccctcg gtgcgctcgg ctccaaaaac aacaaggata ctgtcggacc atcgagaagg   240
ttcggtgatg gtggaaaacc ttctgaagaa cagaagatga atgtgaggca gcctgagtat   300
cgtctcaatg gaagacacgg tcgtcgctct cacgagtttc ttaggagtcc atggatcaag   360
cactataagc cttcaccaaa gtccctaaca gat                                393
```

<210> SEQ ID NO 24
<211> LENGTH: 131
<212> TYPE: PRT
<213> ORGANISM: Brassica napus
<220> FEATURE:
<221> NAME/KEY: peptide
<222> LOCATION: (1)..(131)
<223> OTHER INFORMATION: ceres Seq. ID no. 4796910

<400> SEQUENCE: 24

```
Met Val Gly Asp Tyr Arg Glu Asn Tyr Ser Pro Ser Ser Asp Asp Ser
1               5                   10                  15

Ser Ser Val Gly Glu Glu Thr Thr Ser Ser Met Tyr Ser Ala Arg Asn
            20                  25                  30

Glu Asp Thr Pro Thr Glu Trp Thr Asp Glu Lys His Ser Leu Tyr Leu
        35                  40                  45

Lys Ser Met Glu Ala Ser Phe Val Asp Gln Leu Tyr Asn Ser Leu Gly
    50                  55                  60

Ala Leu Gly Ser Lys Asn Asn Lys Asp Thr Val Gly Pro Ser Arg Arg
65                  70                  75                  80

Phe Gly Asp Gly Gly Lys Pro Ser Glu Glu Gln Lys Met Asn Val Arg
                85                  90                  95
```

```
Gln Pro Glu Tyr Arg Leu Asn Gly Arg His Gly Arg Arg Ser His Glu
                100                 105                 110

Phe Leu Arg Ser Pro Trp Ile Lys His Tyr Lys Pro Ser Pro Lys Ser
            115                 120                 125

Leu Thr Asp
    130

<210> SEQ ID NO 25
<211> LENGTH: 315
<212> TYPE: DNA
<213> ORGANISM: Brassica napus

<400> SEQUENCE: 25
atgtattctg cgaggaatga agatacgcct acagaatgga ccgatgagaa gcatagtttg     60
tatcttaaat caatggaagc ttccttcgtt gatcagctgt acaactccct cggtgcgctc    120
ggctccaaaa acaacaagga tactgtcgga ccatcgagaa ggttcggtga tggtggaaaa    180
ccttctgaag aacagaagat gaatgtgagg cagcctgagt atcgtctcaa tggaagacac    240
ggtcgtcgct ctcacgagtt tcttaggagt ccatggatca agcactataa gccttcacca    300
aagtccctaa cagat                                                     315

<210> SEQ ID NO 26
<211> LENGTH: 105
<212> TYPE: PRT
<213> ORGANISM: Brassica napus
<220> FEATURE:
<221> NAME/KEY: peptide
<222> LOCATION: (1)..(105)
<223> OTHER INFORMATION: ceres Seq. ID no. 4796911

<400> SEQUENCE: 26

Met Tyr Ser Ala Arg Asn Glu Asp Thr Pro Thr Glu Trp Thr Asp Glu
1               5                   10                  15

Lys His Ser Leu Tyr Leu Lys Ser Met Glu Ala Ser Phe Val Asp Gln
                20                  25                  30

Leu Tyr Asn Ser Leu Gly Ala Leu Gly Ser Lys Asn Asn Lys Asp Thr
            35                  40                  45

Val Gly Pro Ser Arg Arg Phe Gly Asp Gly Lys Pro Ser Glu Glu
    50                  55                  60

Gln Lys Met Asn Val Arg Gln Pro Glu Tyr Arg Leu Asn Gly Arg His
65                  70                  75                  80

Gly Arg Arg Ser His Glu Phe Leu Arg Ser Pro Trp Ile Lys His Tyr
                85                  90                  95

Lys Pro Ser Pro Lys Ser Leu Thr Asp
                100                 105

<210> SEQ ID NO 27
<211> LENGTH: 243
<212> TYPE: DNA
<213> ORGANISM: Brassica napus

<400> SEQUENCE: 27
atggaagctt ccttcgttga tcagctgtac aactccctcg gtgcgctcgg ctccaaaaac     60
aacaaggata ctgtcggacc atcgagaagg ttcggtgatg gtggaaaacc ttctgaagaa    120
cagaagatga atgtgaggca gcctgagtat cgtctcaatg gaagacacgg tcgtcgctct    180
cacgagtttc ttaggagtcc atggatcaag cactataagc cttcaccaaa gtccctaaca    240
gat                                                                  243
```

-continued

```
<210> SEQ ID NO 28
<211> LENGTH: 81
<212> TYPE: PRT
<213> ORGANISM: Brassica napus
<220> FEATURE:
<221> NAME/KEY: peptide
<222> LOCATION: (1)..(81)
<223> OTHER INFORMATION: ceres Seq. ID no. 4796912

<400> SEQUENCE: 28
```

Met Glu Ala Ser Phe Val Asp Gln Leu Tyr Asn Ser Leu Gly Ala Leu
1               5                   10                  15

Gly Ser Lys Asn Asn Lys Asp Thr Val Gly Pro Ser Arg Arg Phe Gly
            20                  25                  30

Asp Gly Gly Lys Pro Ser Glu Glu Gln Lys Met Asn Val Arg Gln Pro
        35                  40                  45

Glu Tyr Arg Leu Asn Gly Arg His Gly Arg Arg Ser His Glu Phe Leu
    50                  55                  60

Arg Ser Pro Trp Ile Lys His Tyr Lys Pro Ser Pro Lys Ser Leu Thr
65                  70                  75                  80

Asp

```
<210> SEQ ID NO 29
<211> LENGTH: 1014
<212> TYPE: DNA
<213> ORGANISM: Arabidopsis thaliana
<220> FEATURE:
<221> NAME/KEY: misc_feature
<222> LOCATION: (1)..(1014)
<223> OTHER INFORMATION: ceres Seq. ID no. 12321174

<400> SEQUENCE: 29
ctctctctct taaagctctc ttctttggct ctttcgaaga agaaccattt ttatttccta      60
agagagacga cggagttctt ttctaaagca ccggagagga ggagaagcaa cgatggagaa     120
tgattgcacg gtgaatattg tctctctgga gaaggatcgc gatgtttcgg aggcgtcggc     180
tgaatctcag agcgagtcga ctctttcgaa ctcgctcgat tccggtgtta cggctgagac     240
ctctcgttct gatgctgatt ccaaactgga tgaatgtact gcttggacga atgagaaaca     300
caactcatat cttgattatt tagagagctc gtttgttagg caattatact ccttgcttgg     360
aggtgggact cagagacttt ctagaactcg tgatgtgcag tctaactctc ataaatcagc     420
tgatcagttt accgtcctac aaaatggttg ctggcagaag gttaactttg aaagaaaaca     480
atcttgtttg gagacttcat ctgagtttcg ttttcacaga aattcattga gaaataagcc     540
tgaaaattcc aacggaaatt acaccatggg aactactgtc caaggagatg tgttatgtca     600
tgacgaaacc aaacactcag aggcgtcagg gcagaatttc agagaagaag aagaagaaga     660
agagaaggga gaggtgagca aaaaacgaga agagaagca aataacgatg atagttcatt      720
gaaggaggat caggttgtgc cggtaaggat ggtgaagccc agaacgtgaa agcattagga     780
agtgtagatg aaatactatg aatagagata agaaataga agaaggtgtg gttacgaatg     840
tggagagggt tttgtttgtt gtatagcgtg aggctaaaga gagccttcct tataaaggga     900
tccaatggga tatggaaata ggattggtgt ttgttttcgt taaattttgt ctaatgttaa     960
ctaggggaaa agttatctga tagtattagc atcttatggc aatttttattc tttt          1014

<210> SEQ ID NO 30
<211> LENGTH: 654
<212> TYPE: DNA
<213> ORGANISM: Arabidopsis thaliana
```

```
<400> SEQUENCE: 30
atggagaatg attgcacggt gaatattgtc tctctggaga aggatcgcga tgtttcggag    60
gcgtcggctg aatctcagag cgagtcgact ctttcgaact cgctcgattc cggtgttacg   120
gctgagacct ctcgttctga tgctgattcc aaactggatg aatgtactgc ttggacgaat   180
gagaaacaca actcatatct tgattattta gagagctcgt tgttaggca attatactcc   240 ttgcttggag gtgggactca gagctttct agaactcgtg atgtgcagtc taactctcat   300
aaatcagctg atcagtttac cgtcctacaa atggttgct ggcagaaggt taactttgga   360
aagaaacaat cttgtttgga gacttcatct gagtttcgtt ttcacagaaa ttcattgaga   420
aataagcctg aaaattccaa cggaaattac accatgggaa ctactgtcca aggagatgtg   480
ttatgtcatg acgaaaccaa acactcagag gcgtcagggc agaatttcag agaagaagaa   540
gaagaagaag agaagggaga ggtgagcaaa aaacgagaaa gagaagcaaa taacgatgat   600
agttcattga aggaggatca ggttgtgccg gtaaggatgg tgaagcccag aacg           654
```

<210> SEQ ID NO 31
<211> LENGTH: 218
<212> TYPE: PRT
<213> ORGANISM: Arabidopsis thaliana
<220> FEATURE:
<221> NAME/KEY: peptide
<222> LOCATION: (1)..(218)
<223> OTHER INFORMATION: ceres Seq. ID no. 12321175

<400> SEQUENCE: 31

```
Met Glu Asn Asp Cys Thr Val Asn Ile Val Ser Leu Glu Lys Asp Arg
1               5                   10                  15

Asp Val Ser Glu Ala Ser Ala Glu Ser Gln Ser Glu Ser Thr Leu Ser
            20                  25                  30

Asn Ser Leu Asp Ser Gly Val Thr Ala Glu Thr Ser Arg Ser Asp Ala
        35                  40                  45

Asp Ser Lys Leu Asp Glu Cys Thr Ala Trp Thr Asn Glu Lys His Asn
    50                  55                  60

Ser Tyr Leu Asp Tyr Leu Glu Ser Ser Phe Val Arg Gln Leu Tyr Ser
65                  70                  75                  80

Leu Leu Gly Gly Gly Thr Gln Arg Leu Ser Arg Thr Arg Asp Val Gln
                85                  90                  95

Ser Asn Ser His Lys Ser Ala Asp Gln Phe Thr Val Leu Gln Asn Gly
            100                 105                 110

Cys Trp Gln Lys Val Asn Phe Gly Lys Lys Gln Ser Cys Leu Glu Thr
        115                 120                 125

Ser Ser Glu Phe Arg Phe His Arg Asn Ser Leu Arg Asn Lys Pro Glu
    130                 135                 140

Asn Ser Asn Gly Asn Tyr Thr Met Gly Thr Thr Val Gln Gly Asp Val
145                 150                 155                 160

Leu Cys His Asp Glu Thr Lys His Ser Glu Ala Ser Gly Gln Asn Phe
                165                 170                 175

Arg Glu Glu Glu Glu Glu Glu Lys Gly Val Ser Lys Lys Arg
            180                 185                 190

Glu Arg Glu Ala Asn Asn Asp Asp Ser Ser Leu Lys Glu Asp Gln Val
        195                 200                 205

Val Pro Val Arg Met Val Lys Pro Arg Thr
    210                 215
```

```
<210> SEQ ID NO 32
<211> LENGTH: 1027
<212> TYPE: DNA
<213> ORGANISM: Arabidopsis thaliana
<220> FEATURE:
<221> NAME/KEY: misc_feature
<222> LOCATION: (1)..(1027)
<223> OTHER INFORMATION: ceres Seq. ID no. 12323601

<400> SEQUENCE: 32
agatattttg tttctctctt tctctctgat attttcatt ttcttcttct tctctctctc    60
tctccacaaa gataagccaa caatggttgg tgattacaga ggacgcttta gtagccgtcg   120
tttctccgac gactctgacg attcttccga cgatgcttct tccgtggagg gagagaccac   180
ttcttccatg tactctgcgg ggaaagagta tatggaaaca gaatggacta atgagaagca   240
tagtttatat cttaaatcta tggaagcttc attcgtagat cagttatata ctcgctcgg    300 agctctcggg aagaacgaga atgtatccga atcaacgagg ttcggtagcg gtagaaaacc   360
gtctcaagaa cagttcaagg ttcttcatga tggtttctgg cagaagatta atgtgaaaca   420
acctgaacat cggattaacg gaaggcacgg tggtaattct catgagtttc ttaggagtcc   480
atggattaag cattataaac ctttagtaaa gacacaaatc ccggtaacgg atgagcccga   540
aaatcaagtt gttagcagct ctaatgggaa gagggaata tgcagctctg gctcagcctc    600
tagtctcaag cagctaagct ctcattcgcg tgaccacgac caaatcagcg ttggagaagc   660
agaggtatcg gatcagaact tgttaacga aggaataaaa ggcgaaaacg gaagctcgaa    720
gaagatgaag acggtgatga tgagtgaatc gtcgagtacc gatcaggttg ttccactcaa   780
taagctcttg caacatgacg taaatttgaa gtctgttct tgagaggtca gatggtgaag    840
ctttatatga ggagagaatt ttgtaatgta tatatatttg cataacttat aagtcaaatt    900
tactatcctt agttacaagt ttcttcatca tatatccta actataaata tattatatg     960 ctcatgtgag tggattcatt tgtactgtaa aaccctttaga aagacgtcaa attagtattt   1020
gatggtc                                                             1027

<210> SEQ ID NO 33
<211> LENGTH: 819
<212> TYPE: DNA
<213> ORGANISM: Arabidopsis thaliana

<400> SEQUENCE: 33
gatattttgt ttctctcttt ctctctgata tttttcattt tcttcttctt ctctctctct    60
ctccacaaag ataagccaac aatggttggt gattacagag gacgctttag tagccgtcgt   120
ttctccgacg actctgacga ttcttccgac gatgcttctt ccgtggaggg agagaccact   180
tcttccatgt actctgcggg gaaagagtat atggaaacag aatggactaa tgagaagcat   240
agtttatatc ttaaatctat ggaagcttca ttcgtagatc agttatataa ctcgctcgga   300
gctctcggga agaacgagaa tgtatccgaa tcaacgaggt tcggtagcgg tagaaaaccg   360
tctcaagaac agttcaaggt tcttcatgat ggtttctggc agaagattaa tgtgaaacaa   420
cctgaacatc ggattaacgg aaggcacggt ggtaattctc atgagtttct taggagtcca   480
tggattaagc attataaacc tttagtaaag acacaaatcc cggtaacgga tgagcccgaa   540 atcaagttg ttagcagctc taatgggaag aagggaatat gcagctctgg ctcagcctct    600
agtctcaagc agctaagctc tcattcgcgt gaccacgacc aaatcagcgt tggagaagca   660
gaggtatcgg atcagaactt gttaacgaag gaataaaag gcgaaaacgg aagctcgaag    720
```

```
aagatgaaga cggtgatgat gagtgaatcg tcgagtaccg atcaggttgt tccactcaat      780
aagctcttgc aacatgacgt aaatttgaag tctgtttct                             819
```

<210> SEQ ID NO 34
<211> LENGTH: 273
<212> TYPE: PRT
<213> ORGANISM: Arabidopsis thaliana
<220> FEATURE:
<221> NAME/KEY: peptide
<222> LOCATION: (1)..(273)
<223> OTHER INFORMATION: ceres Seq. ID no. 12323602

<400> SEQUENCE: 34

```
Asp Ile Leu Phe Leu Ser Phe Ser Leu Ile Phe Phe Ile Phe Phe Phe
1               5                   10                  15

Phe Ser Leu Ser Leu His Lys Asp Lys Pro Thr Met Val Gly Asp Tyr
            20                  25                  30

Arg Gly Arg Phe Ser Ser Arg Arg Phe Ser Asp Asp Ser Asp Asp Ser
        35                  40                  45

Ser Asp Asp Ala Ser Ser Val Glu Gly Glu Thr Thr Ser Ser Met Tyr
    50                  55                  60

Ser Ala Gly Lys Glu Tyr Met Glu Thr Glu Trp Thr Asn Glu Lys His
65                  70                  75                  80

Ser Leu Tyr Leu Lys Ser Met Glu Ala Ser Phe Val Asp Gln Leu Tyr
                85                  90                  95

Asn Ser Leu Gly Ala Leu Gly Lys Asn Glu Asn Val Ser Glu Ser Thr
            100                 105                 110

Arg Phe Gly Ser Gly Arg Lys Pro Ser Gln Glu Gln Phe Lys Val Leu
        115                 120                 125

His Asp Gly Phe Trp Gln Lys Ile Asn Val Lys Gln Pro Glu His Arg
    130                 135                 140

Ile Asn Gly Arg His Gly Gly Asn Ser His Glu Phe Leu Arg Ser Pro
145                 150                 155                 160

Trp Ile Lys His Tyr Lys Pro Leu Val Lys Thr Gln Ile Pro Val Thr
                165                 170                 175

Asp Glu Pro Glu Asn Gln Val Val Ser Ser Asn Gly Lys Lys Gly
            180                 185                 190

Ile Cys Ser Ser Gly Ser Ala Ser Ser Leu Lys Gln Leu Ser Ser His
        195                 200                 205

Ser Arg Asp His Asp Gln Ile Ser Val Gly Glu Ala Glu Val Ser Asp
    210                 215                 220

Gln Asn Phe Val Asn Glu Gly Ile Lys Gly Glu Asn Gly Ser Ser Lys
225                 230                 235                 240

Lys Met Lys Thr Val Met Met Ser Glu Ser Ser Thr Asp Gln Val
                245                 250                 255

Val Pro Leu Asn Lys Leu Leu Gln His Asp Val Asn Leu Lys Ser Val
            260                 265                 270

Ser
```

<210> SEQ ID NO 35
<211> LENGTH: 738
<212> TYPE: DNA
<213> ORGANISM: Arabidopsis thaliana

<400> SEQUENCE: 35

```
atggttggtg attacagagg acgctttagt agccgtcgtt tctccgacga ctctgacgat      60
tcttccgacg atgcttcttc cgtggaggga gagaccactt cttccatgta ctctgcgggg    120
```

```
aaagagtata tggaaacaga atggactaat gagaagcata gtttatatct taaatctatg    180
gaagcttcat tcgtagatca gttatataac tcgctcggag ctctcgggaa gaacgagaat    240
gtatccgaat caacgaggtt cggtagcggt agaaaaccgt ctcaagaaca gttcaaggtt    300
cttcatgatg gtttctggca gaagattaat gtgaaacaac ctgaacatcg gattaacgga    360
aggcacggtg gtaattctca tgagtttctt aggagtccat ggattaagca ttataaacct    420
ttagtaaaga cacaaatccc ggtaacggat gagcccgaaa atcaagttgt tagcagctct    480
aatgggaaga agggaatatg cagctctggc tcagcctcta gtctcaagca gctaagctct    540
cattcgcgtg accacgacca aatcagcgtt ggagaagcag aggtatcgga tcagaacttt    600
gttaacgaag gaataaaagg cgaaaacgga agctcgaaga gatgaagac ggtgatgatg    660 agtgaatcgt cgagtaccga tcaggttgtt ccactcaata agctcttgca acatgacgta    720
aatttgaagt ctgtttct                                                  738
```

<210> SEQ ID NO 36
<211> LENGTH: 246
<212> TYPE: PRT
<213> ORGANISM: Arabidopsis thaliana
<220> FEATURE:
<221> NAME/KEY: peptide
<222> LOCATION: (1)..(246)
<223> OTHER INFORMATION: ceres Seq. ID no. 12323603

<400> SEQUENCE: 36

```
Met Val Gly Asp Tyr Arg Gly Arg Phe Ser Ser Arg Arg Phe Ser Asp
1               5                   10                  15

Asp Ser Asp Ser Ser Asp Asp Ala Ser Ser Val Glu Gly Glu Thr
            20                  25                  30

Thr Ser Ser Met Tyr Ser Ala Gly Lys Glu Tyr Met Glu Thr Glu Trp
        35                  40                  45

Thr Asn Glu Lys His Ser Leu Tyr Leu Lys Ser Met Glu Ala Ser Phe
    50                  55                  60

Val Asp Gln Leu Tyr Asn Ser Leu Gly Ala Leu Gly Lys Asn Glu Asn
65                  70                  75                  80

Val Ser Glu Ser Thr Arg Phe Gly Ser Gly Arg Lys Pro Ser Gln Glu
                85                  90                  95

Gln Phe Lys Val Leu His Asp Gly Phe Trp Gln Lys Ile Asn Val Lys
            100                 105                 110

Gln Pro Glu His Arg Ile Asn Gly Arg His Gly Asn Ser His Glu
        115                 120                 125

Phe Leu Arg Ser Pro Trp Ile Lys His Tyr Lys Pro Leu Val Lys Thr
    130                 135                 140

Gln Ile Pro Val Thr Asp Glu Pro Glu Asn Gln Val Val Ser Ser Ser
145                 150                 155                 160

Asn Gly Lys Lys Gly Ile Cys Ser Ser Gly Ser Ala Ser Ser Leu Lys
                165                 170                 175

Gln Leu Ser Ser His Ser Arg Asp His Asp Gln Ile Ser Val Gly Glu
            180                 185                 190

Ala Glu Val Ser Asp Gln Asn Phe Val Asn Glu Gly Ile Lys Gly Glu
        195                 200                 205

Asn Gly Ser Ser Lys Lys Met Lys Thr Val Met Met Ser Glu Ser Ser
    210                 215                 220
```

```
Ser Thr Asp Gln Val Val Pro Leu Asn Lys Leu Leu Gln His Asp Val
225                 230                 235                 240

Asn Leu Lys Ser Val Ser
            245
```

<210> SEQ ID NO 37
<211> LENGTH: 633
<212> TYPE: DNA
<213> ORGANISM: Arabidopsis thaliana

<400> SEQUENCE: 37

```
atgtactctg cggggaaaga gtatatggaa acagaatgga ctaatgagaa gcatagttta    60
tatcttaaat ctatggaagc ttcattcgta gatcagttat ataactcgct cggagctctc   120
gggaagaacg agaatgtatc cgaatcaacg aggttcggta gcggtagaaa accgtctcaa   180
gaacagttca aggttcttca tgatggtttc tggcagaaga ttaatgtgaa acaacctgaa   240
catcggatta cgaaggca cggtggtaat tctcatgagt ttcttaggag tccatggatt   300
aagcattata aacctttagt aaagacacaa atcccggtaa cggatgagcc cgaaaatcaa   360
gttgttagca gctctaatgg gaagaaggga atatgcagct ctggctcagc ctctagtctc   420
aagcagctaa gctctcattc gcgtgaccac gaccaaatca gcgttggaga agcagaggta   480
tcggatcaga actttgttaa cgaaggaata aaaggcgaaa acggaagctc gaagaagatg   540
aagacggtga tgatgagtga atcgtcgagt accgatcagg ttgttccact caataagctc   600
ttgcaacatg acgtaaattt gaagtctgtt tct                                633
```

<210> SEQ ID NO 38
<211> LENGTH: 211
<212> TYPE: PRT
<213> ORGANISM: Arabidopsis thaliana
<220> FEATURE:
<221> NAME/KEY: peptide
<222> LOCATION: (1)..(211)
<223> OTHER INFORMATION: ceres Seq. ID no. 12323604

<400> SEQUENCE: 38

```
Met Tyr Ser Ala Gly Lys Glu Tyr Met Glu Thr Glu Trp Thr Asn Glu
1               5                  10                  15

Lys His Ser Leu Tyr Leu Lys Ser Met Glu Ala Ser Phe Val Asp Gln
            20                  25                  30

Leu Tyr Asn Ser Leu Gly Ala Leu Gly Lys Asn Glu Asn Val Ser Glu
        35                  40                  45

Ser Thr Arg Phe Gly Ser Gly Arg Lys Pro Ser Gln Glu Gln Phe Lys
    50                  55                  60

Val Leu His Asp Gly Phe Trp Gln Lys Ile Asn Val Lys Gln Pro Glu
65                  70                  75                  80

His Arg Ile Asn Gly Arg His Gly Asn Ser His Glu Phe Leu Arg
                85                  90                  95

Ser Pro Trp Ile Lys His Tyr Lys Pro Leu Val Lys Thr Gln Ile Pro
                100                 105                 110

Val Thr Asp Glu Pro Glu Asn Gln Val Val Ser Ser Asn Gly Lys
            115                 120                 125

Lys Gly Ile Cys Ser Ser Gly Ser Ala Ser Ser Leu Lys Gln Leu Ser
        130                 135                 140

Ser His Ser Arg Asp His Asp Gln Ile Ser Val Gly Glu Ala Glu Val
145                 150                 155                 160

Ser Asp Gln Asn Phe Val Asn Glu Gly Ile Lys Gly Glu Asn Gly Ser
                165                 170                 175
```

```
Ser Lys Lys Met Lys Thr Val Met Met Ser Glu Ser Ser Thr Asp
            180                 185                 190

Gln Val Val Pro Leu Asn Lys Leu Leu Gln His Asp Val Asn Leu Lys
        195                 200                 205

Ser Val Ser
    210

<210> SEQ ID NO 39
<211> LENGTH: 960
<212> TYPE: DNA
<213> ORGANISM: Arabidopsis thaliana
<220> FEATURE:
<221> NAME/KEY: misc_feature
<222> LOCATION: (1)..(960)
<223> OTHER INFORMATION: ceres Seq. ID no. 13491409

<400> SEQUENCE: 39 attttttgttt ctctctttct ctctgatatt tttcattttc ttcttcttct ctctctctct      60
ccacaaagat aagccaacaa tggttggtga ttacagagga cgctttagta gccgtcgttt     120
ctccgatgac tctgacgatt cttccgacga tgcttcttcc gtggagggag agaccacttc     180
ttccatgtac tctgcgggga aagagtatat ggaaacagaa tggactaatg agaagcatag     240
tttatatctt aaatctatgg aagcttcatt cgtagatcag ttatataact cgctcggagc     300
tctcgggaag aacgagaatg tatccgaatc aacgaggttc ggtagcggta gaaaaccgtc     360
tcaagaacag ttcaaggttc ttcatgatgg tttctggcag aagattaatg tgaaacaacc     420
tgaacatcgg attaacggaa ggcacggtgg taattctcat gagtttctta ggagtccatg     480
gattaagcat tataaacctt tagtaaagac acaaatcccg gtaacggatg agcccgaaaa     540
tcaagttgtt agcagctcta atgggaagaa gggaatatgc agctctggct cagcctctag     600
tctcaagcag ctaagctctc attcgcgtga ccacgaccaa atcagcgttg agaagcaga     660 ggtatcggat cagaactttg ttaacgaagg aataaaaggc gaaaacggaa gctcgaagaa     720
gatgaagacg gtgatgatga gtgaatcgtc gagtaccgat caggttgttc cactcaataa     780
actcttgcaa catgacgtaa atttgaagtc tgtttcttga gaggtcagat ggtgaagctt     840
tatatgagga gagaattttg taatgtatat atatttgcat aacttataag tcaaatttac     900
tatccttagt tacaagtttc ttcatcatat atccctaact ataaatatat ttatatgccc     960

<210> SEQ ID NO 40
<211> LENGTH: 816
<212> TYPE: DNA
<213> ORGANISM: Arabidopsis thaliana

<400> SEQUENCE: 40
tttttgtttc tctctttctc tctgatattt ttcattttct tcttcttctc tctctctc       60 cacaaagata agccaacaat ggttggtgat tacagaggac gctttagtag ccgtcgtttc     120
tccgatgact ctgacgattc ttccgacgat gcttcttccg tggagggaga gaccacttct     180
tccatgtact ctgcggggaa agagtatatg gaaacagaat ggactaatga agcatagt     240 ttatatctta aatctatgga agcttcattc gtagatcagt tatataactc gctcggagct     300
ctcgggaaga acgagaatgt atccgaatca acgaggttcg gtagcggtag aaaaccgtct     360
caagaacagt tcaaggttct tcatgatggt ttctggcaga agattaatgt gaaacaacct     420
gaacatcgga ttaacggaag gcacggtggt aattctcatg agtttcttag gagtccatgg     480
attaagcatt ataaaccttt agtaaagaca caaatcccgg taacggatga gcccgaaaat     540
caagttgtta gcagctctaa tgggaagaag ggaatatgca gctctggctc agcctctagt     600
```

-continued

```
ctcaagcagc taagctctca ttcgcgtgac cacgaccaaa tcagcgttgg agaagcagag      660
gtatcggatc agaactttgt taacgaagga ataaaaggcg aaaacggaag ctcgaagaag      720
atgaagacgg tgatgatgag tgaatcgtcg agtaccgatc aggttgttcc actcaataaa      780
ctcttgcaac atgacgtaaa tttgaagtct gtttct                                816
```

```
<210> SEQ ID NO 41
<211> LENGTH: 272
<212> TYPE: PRT
<213> ORGANISM: Arabidopsis thaliana
<220> FEATURE:
<221> NAME/KEY: peptide
<222> LOCATION: (1)..(272)
<223> OTHER INFORMATION: ceres Seq. ID no. 13491410
```

<400> SEQUENCE: 41

```
Phe Leu Phe Leu Ser Phe Ser Leu Ile Phe Phe Ile Phe Phe Phe
1               5                   10                  15

Ser Leu Ser Leu His Lys Asp Lys Pro Thr Met Val Gly Asp Tyr Arg
                20                  25                  30

Gly Arg Phe Ser Ser Arg Arg Phe Ser Asp Asp Ser Asp Ser Ser
            35                  40                  45

Asp Asp Ala Ser Ser Val Glu Gly Glu Thr Thr Ser Ser Met Tyr Ser
    50                  55                  60

Ala Gly Lys Glu Tyr Met Glu Thr Glu Trp Thr Asn Glu Lys His Ser
65                  70                  75                  80

Leu Tyr Leu Lys Ser Met Glu Ala Ser Phe Val Asp Gln Leu Tyr Asn
                85                  90                  95

Ser Leu Gly Ala Leu Gly Lys Asn Glu Asn Val Ser Glu Ser Thr Arg
            100                 105                 110

Phe Gly Ser Gly Arg Lys Pro Ser Gln Glu Gln Phe Lys Val Leu His
        115                 120                 125

Asp Gly Phe Trp Gln Lys Ile Asn Val Lys Gln Pro Glu His Arg Ile
    130                 135                 140

Asn Gly Arg His Gly Gly Asn Ser His Glu Phe Leu Arg Ser Pro Trp
145                 150                 155                 160

Ile Lys His Tyr Lys Pro Leu Val Lys Thr Gln Ile Pro Val Thr Asp
                165                 170                 175

Glu Pro Glu Asn Gln Val Val Ser Ser Asn Gly Lys Lys Gly Ile
            180                 185                 190

Cys Ser Ser Gly Ser Ala Ser Ser Leu Lys Gln Leu Ser Ser His Ser
        195                 200                 205

Arg Asp His Asp Gln Ile Ser Val Gly Glu Ala Glu Val Ser Asp Gln
    210                 215                 220

Asn Phe Val Asn Glu Gly Ile Lys Gly Glu Asn Gly Ser Ser Lys Lys
225                 230                 235                 240

Met Lys Thr Val Met Met Ser Glu Ser Ser Thr Asp Gln Val Val
                245                 250                 255

Pro Leu Asn Lys Leu Leu Gln His Asp Val Asn Leu Lys Ser Val Ser
            260                 265                 270
```

```
<210> SEQ ID NO 42
<211> LENGTH: 738
<212> TYPE: DNA
<213> ORGANISM: Arabidopsis thaliana
```

-continued

```
<400> SEQUENCE: 42
atggttggtg attacagagg acgctttagt agccgtcgtt tctccgatga ctctgacgat      60
tcttccgacg atgcttcttc cgtggaggga gagaccactt cttccatgta ctctgcgggg     120
aaagagtata tggaaacaga atggactaat gagaagcata gtttatatct taaatctatg     180
gaagcttcat tcgtagatca gttatataac tcgctcggag ctctcgggaa gaacgagaat     240
gtatccgaat caacgaggtt cggtagcggt agaaaaccgt ctcaagaaca gttcaaggtt     300
cttcatgatg gtttctggca aagattaat gtgaaacaac ctgaacatcg gattaacgga      360
aggcacggtg gtaattctca tgagtttctt aggagtccat ggattaagca ttataaacct     420
ttagtaaaga cacaaatccc ggtaacggat gagcccgaaa atcaagttgt tagcagctct     480
aatgggaaga agggaatatg cagctctggc tcagcctcta gtctcaagca gctaagctct     540
cattcgcgtg accacgacca atcagcgtt ggagaagcag aggtatcgga tcagaacttt      600
gttaacgaag aataaaagg cgaaaacgga agctcgaaga agatgaagac ggtgatgatg       660
agtgaatcgt cgagtaccga tcaggttgtt ccactcaata aactcttgca acatgacgta     720
aatttgaagt ctgtttct                                                   738

<210> SEQ ID NO 43
<211> LENGTH: 246
<212> TYPE: PRT
<213> ORGANISM: Arabidopsis thaliana
<220> FEATURE:
<221> NAME/KEY: peptide
<222> LOCATION: (1)..(246)
<223> OTHER INFORMATION: ceres Seq. ID no. 13491411

<400> SEQUENCE: 43

Met Val Gly Asp Tyr Arg Gly Arg Phe Ser Ser Arg Arg Phe Ser Asp
1               5                   10                  15

Asp Ser Asp Asp Ser Ser Asp Asp Ala Ser Ser Val Glu Gly Glu Thr
            20                  25                  30

Thr Ser Ser Met Tyr Ser Ala Gly Lys Glu Tyr Met Glu Thr Glu Trp
        35                  40                  45

Thr Asn Glu Lys His Ser Leu Tyr Leu Lys Ser Met Glu Ala Ser Phe
    50                  55                  60

Val Asp Gln Leu Tyr Asn Ser Leu Gly Ala Leu Gly Lys Asn Glu Asn
65                  70                  75                  80

Val Ser Glu Ser Thr Arg Phe Gly Ser Gly Arg Lys Pro Ser Gln Glu
                85                  90                  95

Gln Phe Lys Val Leu His Asp Gly Phe Trp Gln Lys Ile Asn Val Lys
            100                 105                 110

Gln Pro Glu His Arg Ile Asn Gly Arg His Gly Gly Asn Ser His Glu
        115                 120                 125

Phe Leu Arg Ser Pro Trp Ile Lys His Tyr Lys Pro Leu Val Lys Thr
    130                 135                 140

Gln Ile Pro Val Thr Asp Glu Pro Glu Asn Gln Val Val Ser Ser
145                 150                 155                 160

Asn Gly Lys Lys Gly Ile Cys Ser Ser Gly Ser Ala Ser Ser Leu Lys
                165                 170                 175

Gln Leu Ser Ser His Ser Arg Asp His Asp Gln Ile Ser Val Gly Glu
            180                 185                 190

Ala Glu Val Ser Asp Gln Asn Phe Val Asn Glu Gly Ile Lys Gly Glu
        195                 200                 205
```

```
Asn Gly Ser Ser Lys Lys Met Lys Thr Val Met Met Ser Glu Ser Ser
            210                 215                 220

Ser Thr Asp Gln Val Val Pro Leu Asn Lys Leu Leu Gln His Asp Val
225                 230                 235                 240

Asn Leu Lys Ser Val Ser
                245

<210> SEQ ID NO 44
<211> LENGTH: 633
<212> TYPE: DNA
<213> ORGANISM: Arabidopsis thaliana

<400> SEQUENCE: 44
atgtactctg cggggaaaga gtatatggaa acagaatgga ctaatgagaa gcatagttta      60
tatcttaaat ctatggaagc ttcattcgta gatcagttat ataactcgct cggagctctc     120
gggaagaacg agaatgtatc cgaatcaacg aggttcggta gcggtagaaa accgtctcaa     180
gaacagttca aggttcttca tgatggtttc tggcagaaga ttaatgtgaa acaacctgaa     240
catcggatta acggaaggca cggtggtaat tctcatgagt tccttaggag tccatggatt     300
aagcattata aacctttagt aaagacacaa atcccggtaa cggatgagcc cgaaaatcaa     360
gttgttagca gctctaatgg aagaagggaa atatgcagct ctggctcagc ctctagtctc     420
aagcagctaa gctctcattc gcgtgaccac gaccaaatca gcgttggaga agcagaggta     480
tcggatcaga actttgttaa cgaaggaata aaaggcgaaa acggaagctc gaagaagatg     540
aagacggtga tgatgagtga atcgtcgagt accgatcagg ttgttccact caataaactc     600
ttgcaacatg acgtaaattt gaagtctgtt tct                                  633

<210> SEQ ID NO 45
<211> LENGTH: 211
<212> TYPE: PRT
<213> ORGANISM: Arabidopsis thaliana
<220> FEATURE:
<221> NAME/KEY: peptide
<222> LOCATION: (1)..(211)
<223> OTHER INFORMATION: ceres Seq. ID no. 13491412

<400> SEQUENCE: 45

Met Tyr Ser Ala Gly Lys Glu Tyr Met Glu Thr Glu Trp Thr Asn Glu
1               5                   10                  15

Lys His Ser Leu Tyr Leu Lys Ser Met Glu Ala Ser Phe Val Asp Gln
            20                  25                  30

Leu Tyr Asn Ser Leu Gly Ala Leu Gly Lys Asn Glu Asn Val Ser Glu
        35                  40                  45

Ser Thr Arg Phe Gly Ser Gly Arg Lys Pro Ser Gln Glu Gln Phe Lys
    50                  55                  60

Val Leu His Asp Gly Phe Trp Gln Lys Ile Asn Val Lys Gln Pro Glu
65                  70                  75                  80

His Arg Ile Asn Gly Arg His Gly Gly Asn Ser His Glu Phe Leu Arg
                85                  90                  95

Ser Pro Trp Ile Lys His Tyr Lys Pro Leu Val Lys Thr Gln Ile Pro
            100                 105                 110

Val Thr Asp Glu Pro Glu Asn Gln Val Val Ser Ser Asn Gly Lys
        115                 120                 125

Lys Gly Ile Cys Ser Ser Gly Ser Ala Ser Ser Leu Lys Gln Leu Ser
    130                 135                 140
```

```
Ser His Ser Arg Asp His Asp Gln Ile Ser Val Gly Glu Ala Glu Val
145                 150                 155                 160

Ser Asp Gln Asn Phe Val Asn Glu Gly Ile Lys Gly Glu Asn Gly Ser
                165                 170                 175

Ser Lys Lys Met Lys Thr Val Met Met Ser Glu Ser Ser Thr Asp
            180                 185                 190

Gln Val Val Pro Leu Asn Lys Leu Leu Gln His Asp Val Asn Leu Lys
        195                 200                 205

Ser Val Ser
    210

<210> SEQ ID NO 46
<211> LENGTH: 1031
<212> TYPE: DNA
<213> ORGANISM: Artificial Sequence
<220> FEATURE:
<223> OTHER INFORMATION: clone nucleotide 486033
<220> FEATURE:
<221> NAME/KEY: misc_feature
<222> LOCATION: (609)..(609)
<223> OTHER INFORMATION: n is a, c, g, or t

<400> SEQUENCE: 46
agttcgcttt ggcctccgct tgccccctcc ctctcgcgtc tctatacatc gccgctgttg      60
tgttgcagtt cagtttgcat cctgagctct tcctggacc agccgagatt tctctctctg     120
cgcatctcta attcatcttc gtcgagagga gctgttcctc ttctttgccg cctcgaatct    180
gggactggtc ggttttctgg atccctgctg cctgtcgggt tctcgagagg tgtaaaatcc   240
aatggagggt gtgtcatcgt tgaaccagcc gttgatcaac gacgaccggc agcccgtgcc   300
cagcagtatc gccaagggtg atcaaatcca aggcctgttg tcgggtgaat ggacaaatga   360
gcggcacagc tcgtacataa gctccatgga ggcatctttc gtggagcaac tccgtagtgg   420
ttccaaggcc atccaggagg gcttgtgcca gagcatgagg attccgaggg atgatgctcg   480
cagccatgac gtccctgaga gtccgtgggt ggtggtgagg cgtttcaggc cacgcggtgt   540
ccaccatggc gatggaatgg aagtggaacc tttggtcgat ggttatggat caggtactga   600
cacggcccng agagaaggtc cggacccacg caagatagcg aaggcttctg ctattattga   660
agtcacggac cagaattttc ctgaggaggg gattcaatcc agtaacggtg catgcaagag   720
acagaaatct actcctggca atgcatcaaa tggccagggt acttaacaag atagtggaag   780
ccaagccatg ccctctctga agccttcagg aggccatggg ggaaacgaga cttgtctgca   840
gtactacgtg atgacaggtc gtgctgcagc tgcaagtagt ttggcttacc aaaatatgat   900
atcgtcgtcc tttctgcggt gtggagagta gaatatgcat atccacatct gcagagagca   960
ccggttctct tcttcttgtt gctgttacta ttttgtgcca tggagcaaat ttatttggta   1020
aatttgagct g                                                       1031

<210> SEQ ID NO 47
<211> LENGTH: 174
<212> TYPE: PRT
<213> ORGANISM: Artificial Sequence
<220> FEATURE:
<223> OTHER INFORMATION: clone peptide 486033
<220> FEATURE:
<221> NAME/KEY: misc_feature
<222> LOCATION: (123)..(123)
<223> OTHER INFORMATION: Xaa can be any naturally occurring amino acid
```

-continued

```
<400> SEQUENCE: 47

Met Glu Gly Val Ser Ser Leu Asn Gln Pro Leu Ile Asn Asp Asp Arg
1               5                   10                  15

Gln Pro Val Pro Ser Ser Ile Ala Lys Gly Asp Gln Ile Gln Gly Leu
            20                  25                  30

Leu Ser Gly Glu Trp Thr Asn Glu Arg His Ser Ser Tyr Ile Ser Ser
        35                  40                  45

Met Glu Ala Ser Phe Val Glu Gln Leu Arg Ser Gly Ser Lys Ala Ile
    50                  55                  60

Gln Glu Gly Leu Cys Gln Ser Met Arg Ile Pro Arg Asp Asp Ala Arg
65                  70                  75                  80

Ser His Asp Val Pro Glu Ser Pro Trp Val Val Arg Arg Phe Arg
                85                  90                  95

Pro Arg Gly Val His His Gly Asp Gly Met Glu Val Glu Pro Leu Val
                100                 105                 110

Asp Gly Tyr Gly Ser Gly Thr Asp Thr Ala Xaa Arg Glu Gly Pro Asp
            115                 120                 125

Pro Arg Lys Ile Ala Lys Ala Ser Ala Ile Ile Glu Val Thr Asp Gln
        130                 135                 140

Asn Phe Pro Glu Glu Gly Ile Gln Ser Ser Asn Gly Ala Cys Lys Arg
145                 150                 155                 160

Gln Lys Ser Thr Pro Gly Asn Ala Ser Asn Gly Gln Gly Thr
                165                 170

<210> SEQ ID NO 48
<211> LENGTH: 210
<212> TYPE: PRT
<213> ORGANISM: Artificial Sequence
<220> FEATURE:
<223> OTHER INFORMATION: Consensus sequence derived from various
      organisms
<220> FEATURE:
<221> NAME/KEY: misc_feature
<222> LOCATION: (2)..(2)
<223> OTHER INFORMATION: Xaa is Glu or Lys
<220> FEATURE:
<221> NAME/KEY: misc_feature
<222> LOCATION: (3)..(3)
<223> OTHER INFORMATION: Xaa is a tiny amino acid, specifically,
      alanine, glycine, serine or threonine
<220> FEATURE:
<221> NAME/KEY: misc_feature
<222> LOCATION: (5)..(5)
<223> OTHER INFORMATION: Xaa is Thr or Pro
<220> FEATURE:
<221> NAME/KEY: misc_feature
<222> LOCATION: (7)..(8)
<223> OTHER INFORMATION: Xaa is a tiny amino acid, specifically,
      alanine, glycine, serine or threonine
<220> FEATURE:
<221> NAME/KEY: misc_feature
<222> LOCATION: (9)..(9)
<223> OTHER INFORMATION: Xaa is Met or Gly
<220> FEATURE:
<221> NAME/KEY: misc_feature
<222> LOCATION: (10)..(10)
<223> OTHER INFORMATION: Xaa is Tyr or Ile
<220> FEATURE:
<221> NAME/KEY: misc_feature
<222> LOCATION: (11)..(11)
<223> OTHER INFORMATION: Xaa is a tiny amino acid, specifically,
      alanine, glycine, serine or threonine
<220> FEATURE:
<221> NAME/KEY: misc_feature
<222> LOCATION: (12)..(12)
<223> OTHER INFORMATION: Xaa is Ala or Lys
```

```
<220> FEATURE:
<221> NAME/KEY: misc_feature
<222> LOCATION: (14)..(14)
<223> OTHER INFORMATION: Xaa is Lys or Asn
<220> FEATURE:
<221> NAME/KEY: misc_feature
<222> LOCATION: (15)..(15)
<223> OTHER INFORMATION: Xaa is Glu or Arg
<220> FEATURE:
<221> NAME/KEY: misc_feature
<222> LOCATION: (16)..(16)
<223> OTHER INFORMATION: Xaa is Tyr or Val
<220> FEATURE:
<221> NAME/KEY: misc_feature
<222> LOCATION: (17)..(17)
<223> OTHER INFORMATION: Xaa is an aliphatic residue, specifically,
      isoleucine, valine, leucine, or methionine
<220> FEATURE:
<221> NAME/KEY: misc_feature
<222> LOCATION: (18)..(18)
<223> OTHER INFORMATION: Xaa is any amino acid
<220> FEATURE:
<221> NAME/KEY: misc_feature
<222> LOCATION: (19)..(19)
<223> OTHER INFORMATION: Xaa is a tiny amino acid, specifically,
      alanine, glycine, serine or threonine
<220> FEATURE:
<221> NAME/KEY: misc_feature
<222> LOCATION: (20)..(23)
<223> OTHER INFORMATION: At least 1 but as many as 4 of the Xaa amino
      acids can be present; Xaa is any amino acid
<220> FEATURE:
<221> NAME/KEY: misc_feature
<222> LOCATION: (26)..(26)
<223> OTHER INFORMATION: Xaa is Asn or Asp
<220> FEATURE:
<221> NAME/KEY: misc_feature
<222> LOCATION: (28)..(28)
<223> OTHER INFORMATION: Xaa is a positively charged residue,
      specifically, lysine, arginine, or histidine
<220> FEATURE:
<221> NAME/KEY: misc_feature
<222> LOCATION: (30)..(30)
<223> OTHER INFORMATION: Xaa is any amino acid
<220> FEATURE:
<221> NAME/KEY: misc_feature
<222> LOCATION: (31)..(31)
<223> OTHER INFORMATION: Xaa is Leu or Ser
<220> FEATURE:
<221> NAME/KEY: misc_feature
<222> LOCATION: (33)..(33)
<223> OTHER INFORMATION: Xaa is an aliphatic residue, specifically,
      isoleucine, valine, leucine, or methionine
<220> FEATURE:
<221> NAME/KEY: misc_feature
<222> LOCATION: (34)..(34)
<223> OTHER INFORMATION: Xaa is Lys or Ser
<220> FEATURE:
<221> NAME/KEY: misc_feature
<222> LOCATION: (42)..(42)
<223> OTHER INFORMATION: Xaa is any negatively charged amino acid,
      specifically, aspartic acid or glutamic acid
<220> FEATURE:
<221> NAME/KEY: misc_feature
<222> LOCATION: (45)..(74)
<223> OTHER INFORMATION: Any one or all of the Xaa amino acids can
      either be present or absent; Xaa is any amino acid
<220> FEATURE:
<221> NAME/KEY: misc_feature
<222> LOCATION: (76)..(76)
<223> OTHER INFORMATION: Xaa is Val or Ala
<220> FEATURE:
<221> NAME/KEY: misc_feature
<222> LOCATION: (77)..(77)
<223> OTHER INFORMATION: Xaa is an aliphatic residue, specifically,
      isoleucine, valine, leucine, or methionine
<220> FEATURE:
<221> NAME/KEY: misc_feature
<222> LOCATION: (78)..(79)
<223> OTHER INFORMATION: Xaa is any amino acid
```

```
<220> FEATURE:
<221> NAME/KEY: misc_feature
<222> LOCATION: (80)..(80)
<223> OTHER INFORMATION: Xaa is Gly or Glu
<220> FEATURE:
<221> NAME/KEY: misc_feature
<222> LOCATION: (81)..(82)
<223> OTHER INFORMATION: Xaa is any amino acid
<220> FEATURE:
<221> NAME/KEY: misc_feature
<222> LOCATION: (83)..(83)
<223> OTHER INFORMATION: Xaa is Gln or Glu
<220> FEATURE:
<221> NAME/KEY: misc_feature
<222> LOCATION: (84)..(102)
<223> OTHER INFORMATION: At least 9 but as many as 19 of the Xaa
      amino acids can be present; Xaa is any amino acid
<220> FEATURE:
<221> NAME/KEY: misc_feature
<222> LOCATION: (103)..(103)
<223> OTHER INFORMATION: Xaa is His or Cys
<220> FEATURE:
<221> NAME/KEY: misc_feature
<222> LOCATION: (104)..(104)
<223> OTHER INFORMATION: Xaa is any amino acid
<220> FEATURE:
<221> NAME/KEY: misc_feature
<222> LOCATION: (105)..(105)
<223> OTHER INFORMATION: Xaa is Phe or Val
<220> FEATURE:
<221> NAME/KEY: misc_feature
<222> LOCATION: (106)..(106)
<223> OTHER INFORMATION: Xaa is Leu or Pro
<220> FEATURE:
<221> NAME/KEY: misc_feature
<222> LOCATION: (107)..(107)
<223> OTHER INFORMATION: Xaa is any amino acid
<220> FEATURE:
<221> NAME/KEY: misc_feature
<222> LOCATION: (108)..(108)
<223> OTHER INFORMATION: Xaa is Ser or Asn
<220> FEATURE:
<221> NAME/KEY: misc_feature
<222> LOCATION: (111)..(112)
<223> OTHER INFORMATION: Any one or 11 of the Xaa amino acids can
      either be present or absent; Xaa is any amino acid
<220> FEATURE:
<221> NAME/KEY: misc_feature
<222> LOCATION: (113)..(113)
<223> OTHER INFORMATION: Xaa is an aliphatic residue, specifically,
      isoleucine, valine, leucine, or methionine
<220> FEATURE:
<221> NAME/KEY: misc_feature
<222> LOCATION: (114)..(114)
<223> OTHER INFORMATION: Xaa is any amino acid
<220> FEATURE:
<221> NAME/KEY: misc_feature
<222> LOCATION: (115)..(115)
<223> OTHER INFORMATION: Xaa is a positively charged residue,
      specifically, lysine, arginine, or histidine
<220> FEATURE:
<221> NAME/KEY: misc_feature
<222> LOCATION: (116)..(116)
<223> OTHER INFORMATION: Xaa is any aromatic residue, specifically,
      phenylalanine, tyrosine, or tryptophan
<220> FEATURE:
<221> NAME/KEY: misc_feature
<222> LOCATION: (117)..(117)
<223> OTHER INFORMATION: Xaa is a positively charged residue,
      specifically, lysine, arginine, or histidine
<220> FEATURE:
<221> NAME/KEY: misc_feature
<222> LOCATION: (119)..(126)
<223> OTHER INFORMATION: Any one or all of the Xaa amino acids can
      either be present or absent; Xaa is any amino acid
<220> FEATURE:
<221> NAME/KEY: misc_feature
<222> LOCATION: (127)..(127)
<223> OTHER INFORMATION: Xaa is a tiny amino acid, specifically,
      alanine, glycine, serine or threonine
```

```
<220> FEATURE:
<221> NAME/KEY: misc_feature
<222> LOCATION: (129)..(130)
<223> OTHER INFORMATION: Xaa is any amino acid
<220> FEATURE:
<221> NAME/KEY: misc_feature
<222> LOCATION: (131)..(131)
<223> OTHER INFORMATION: Xaa is Glu or Asn
<220> FEATURE:
<221> NAME/KEY: misc_feature
<222> LOCATION: (132)..(139)
<223> OTHER INFORMATION: Xaa is any amino acid
<220> FEATURE:
<221> NAME/KEY: misc_feature
<222> LOCATION: (140)..(140)
<223> OTHER INFORMATION: Xaa is Gly
<220> FEATURE:
<221> NAME/KEY: misc_feature
<222> LOCATION: (141)..(146)
<223> OTHER INFORMATION: Any one or all of the Xaa amino acids can
      either be present or absent; Xaa is any amino acid
<220> FEATURE:
<221> NAME/KEY: misc_feature
<222> LOCATION: (148)..(148)
<223> OTHER INFORMATION: Xaa is Gly or Pro
<220> FEATURE:
<221> NAME/KEY: misc_feature
<222> LOCATION: (149)..(149)
<223> OTHER INFORMATION: Xaa is a tiny amino acid, specifically,
      alanine, glycine, serine or threonine
<220> FEATURE:
<221> NAME/KEY: misc_feature
<222> LOCATION: (150)..(150)
<223> OTHER INFORMATION: Xaa is any amino acid
<220> FEATURE:
<221> NAME/KEY: misc_feature
<222> LOCATION: (151)..(151)
<223> OTHER INFORMATION: Xaa is a tiny amino acid, specifically,
      alanine, glycine, serine or threonine
<220> FEATURE:
<221> NAME/KEY: misc_feature
<222> LOCATION: (152)..(153)
<223> OTHER INFORMATION: Xaa is any amino acid
<220> FEATURE:
<221> NAME/KEY: misc_feature
<222> LOCATION: (154)..(154)
<223> OTHER INFORMATION: Xaa is a positively charged residue,
      specifically, lysine, arginine, or histidine
<220> FEATURE:
<221> NAME/KEY: misc_feature
<222> LOCATION: (155)..(171)
<223> OTHER INFORMATION: At least 6 but as many as 17 of the Xaa
      amino acids can be present; Xaa is any amino acid
<220> FEATURE:
<221> NAME/KEY: misc_feature
<222> LOCATION: (172)..(172)
<223> OTHER INFORMATION: Xaa is Gln or Lys
<220> FEATURE:
<221> NAME/KEY: misc_feature
<222> LOCATION: (173)..(173)
<223> OTHER INFORMATION: Xaa is an aliphatic residue, specifically,
      isoleucine, valine, leucine, or methionine
<220> FEATURE:
<221> NAME/KEY: misc_feature
<222> LOCATION: (174)..(176)
<223> OTHER INFORMATION: Xaa is any amino acid
<220> FEATURE:
<221> NAME/KEY: misc_feature
<222> LOCATION: (177)..(177)
<223> OTHER INFORMATION: Xaa is Glu or Ser
<220> FEATURE:
<221> NAME/KEY: misc_feature
<222> LOCATION: (178)..(180)
<223> OTHER INFORMATION: At least 1 but as many as 3 of the Xaa amino
      acids can be present; Xaa is any amino acid
<220> FEATURE:
<221> NAME/KEY: misc_feature
<222> LOCATION: (183)..(183)
<223> OTHER INFORMATION: Xaa is a tiny amino acid, specifically,
      alanine, glycine, serine or threonine
```

```
-continued

<220> FEATURE:
<221> NAME/KEY: misc_feature
<222> LOCATION: (188)..(189)
<223> OTHER INFORMATION: Xaa is any amino acid
<220> FEATURE:
<221> NAME/KEY: misc_feature
<222> LOCATION: (190)..(190)
<223> OTHER INFORMATION: Xaa is any negatively charged amino acid,
      specifically, aspartic acid or glutamic acid
<220> FEATURE:
<221> NAME/KEY: misc_feature
<222> LOCATION: (191)..(191)
<223> OTHER INFORMATION: Xaa is Gly or Glu
<220> FEATURE:
<221> NAME/KEY: misc_feature
<222> LOCATION: (192)..(192)
<223> OTHER INFORMATION: Xaa is Ile or Ala
<220> FEATURE:
<221> NAME/KEY: misc_feature
<222> LOCATION: (193)..(193)
<223> OTHER INFORMATION: Xaa is any amino acid
<220> FEATURE:
<221> NAME/KEY: misc_feature
<222> LOCATION: (194)..(194)
<223> OTHER INFORMATION: Xaa is a tiny amino acid, specifically,
      alanine, glycine, serine or threonine
<220> FEATURE:
<221> NAME/KEY: misc_feature
<222> LOCATION: (195)..(195)
<223> OTHER INFORMATION: Xaa is Glu or Ser
<220> FEATURE:
<221> NAME/KEY: misc_feature
<222> LOCATION: (196)..(196)
<223> OTHER INFORMATION: Xaa is Asn or Thr
<220> FEATURE:
<221> NAME/KEY: misc_feature
<222> LOCATION: (197)..(197)
<223> OTHER INFORMATION: Xaa is Gly or Glu
<220> FEATURE:
<221> NAME/KEY: misc_feature
<222> LOCATION: (198)..(198)
<223> OTHER INFORMATION: Xaa is a tiny amino acid, specifically,
      alanine, glycine, serine or threonine
<220> FEATURE:
<221> NAME/KEY: misc_feature
<222> LOCATION: (199)..(199)
<223> OTHER INFORMATION: Xaa is any amino acid
<220> FEATURE:
<221> NAME/KEY: misc_feature
<222> LOCATION: (201)..(202)
<223> OTHER INFORMATION: Xaa is any amino acid
<220> FEATURE:
<221> NAME/KEY: misc_feature
<222> LOCATION: (204)..(204)
<223> OTHER INFORMATION: Xaa is any amino acid
<220> FEATURE:
<221> NAME/KEY: misc_feature
<222> LOCATION: (205)..(205)
<223> OTHER INFORMATION: Xaa is Val or Arg
<220> FEATURE:
<221> NAME/KEY: misc_feature
<222> LOCATION: (206)..(206)
<223> OTHER INFORMATION: Xaa is Met or Arg
<220> FEATURE:
<221> NAME/KEY: misc_feature
<222> LOCATION: (207)..(207)
<223> OTHER INFORMATION: Xaa is an aliphatic residue, specifically,
      isoleucine, valine, leucine, or methionine
<220> FEATURE:
<221> NAME/KEY: misc_feature
<222> LOCATION: (209)..(209)
<223> OTHER INFORMATION: Xaa is Glu or Arg
<220> FEATURE:
<221> NAME/KEY: misc_feature
<222> LOCATION: (210)..(210)
<223> OTHER INFORMATION: Xaa is a tiny amino acid, specifically,
      alanine, glycine, serine or threonine
```

```
<400> SEQUENCE: 48

Val Xaa Xaa Glu Xaa Thr Xaa Xaa Xaa Xaa Xaa Gly Xaa Xaa Xaa
1               5

-continued

```
<220> FEATURE:
<221> NAME/KEY: misc_feature
<222> LOCATION: (18)..(31)
<223> OTHER INFORMATION: At least 11 but as many as 14 of the Xaa
      amino acids can be present; Xaa is any amino acid
<220> FEATURE:
<221> NAME/KEY: misc_feature
<222> LOCATION: (34)..(34)
<223> OTHER INFORMATION: Xaa is Asn or Asp
<220> FEATURE:
<221> NAME/KEY: misc_feature
<222> LOCATION: (36)..(36)
<223> OTHER INFORMATION: Xaa is a positively charged residue,
      specifically, lysine, arginine, or histidine
<220> FEATURE:
<221> NAME/KEY: misc_feature
<222> LOCATION: (38)..(39)
<223> OTHER INFORMATION: Xaa is any amino acid
<220> FEATURE:
<221> NAME/KEY: misc_feature
<222> LOCATION: (41)..(41)
<223> OTHER INFORMATION: Xaa is an aliphatic residue, specifically,
      isoleucine, valine, leucine, or methionine
<220> FEATURE:
<221> NAME/KEY: misc_feature
<222> LOCATION: (42)..(42)
<223> OTHER INFORMATION: Xaa is any amino acid
<220> FEATURE:
<221> NAME/KEY: misc_feature
<222> LOCATION: (43)..(43)
<223> OTHER INFORMATION: Xaa is Ser or Tyr
<220> FEATURE:
<221> NAME/KEY: misc_feature
<222> LOCATION: (44)..(44)
<223> OTHER INFORMATION: Xaa is an aliphatic residue, specifically,
      isoleucine, valine, leucine, or methionine
<220> FEATURE:
<221> NAME/KEY: misc_feature
<222> LOCATION: (46)..(46)
<223> OTHER INFORMATION: Xaa is a tiny amino acid, specifically,
      alanine, glycine, serine or threonine
<220> FEATURE:
<221> NAME/KEY: misc_feature
<222> LOCATION: (50)..(50)
<223> OTHER INFORMATION: Xaa is any amino acid
<220> FEATURE:
<221> NAME/KEY: misc_feature
<222> LOCATION: (52)..(52)
<223> OTHER INFORMATION: Xaa is Lys or Ser
<220> FEATURE:
<221> NAME/KEY: misc_feature
<222> LOCATION: (53)..(135)
<223> OTHER INFORMATION: At least 8 but as many as 83 of the Xaa amino
      acids can be present; Xaa is any amino acid
<220> FEATURE:
<221> NAME/KEY: misc_feature
<222> LOCATION: (136)..(136)
<223> OTHER INFORMATION: Xaa is Pro or Glu
<220> FEATURE:
<221> NAME/KEY: misc_feature
<222> LOCATION: (137)..(137)
<223> OTHER INFORMATION: Xaa is any aromatic residue, specifically,
      phenylalanine, tyrosine, and tryptophan
<220> FEATURE:
<221> NAME/KEY: misc_feature
<222> LOCATION: (138)..(141)
<223> OTHER INFORMATION: At least 2 but as many as 4 of the Xaa amino
      acids can be present; Xaa is any amino acid
<220> FEATURE:
<221> NAME/KEY: misc_feature
<222> LOCATION: (142)..(142)
<223> OTHER INFORMATION: Xaa is a positively charged residue,
      specifically, lysine, arginine, or histidine
<220> FEATURE:
<221> NAME/KEY: misc_feature
<222> LOCATION: (143)..(231)
<223> OTHER INFORMATION: At least 9 but as many as 89 of the Xaa amino
      acids can be present; Xaa is any amino acid
```

```
<220> FEATURE:
<221> NAME/KEY: misc_feature
<222> LOCATION: (233)..(234)
<223> OTHER INFORMATION: Xaa is any amino acid
<220> FEATURE:
<221> NAME/KEY: misc_feature
<222> LOCATION: (235)..(235)
<223> OTHER INFORMATION: Xaa is Asp or Gly
<220> FEATURE:
<221> NAME/KEY: misc_feature
<222> LOCATION: (239)..(240)
<223> OTHER INFORMATION: Xaa is any amino acid
<220> FEATURE:
<221> NAME/KEY: misc_feature
<222> LOCATION: (241)..(241)
<223> OTHER INFORMATION: Xaa is any negatively charged amino acid,
      specifically, aspartic acid or glutamic acid

<400> SEQUENCE: 49

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Trp
            20                  25                  30

Thr Xaa Glu Xaa His Xaa Xaa Tyr Xaa Xaa Xaa Xaa Glu Xaa Ser Phe
        35                  40                  45

Val Xaa Gln Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Glu Xaa Xaa Xaa Gln Asn Phe Xaa Xaa
225                 230                 235                 240

Xaa

<210> SEQ ID NO 50
<211> LENGTH: 19
<212> TYPE: DNA
<213> ORGANISM: Artificial Sequence
<220> FEATURE:
<223> OTHER INFORMATION: Oligo primer used in the generation of labeled
      probes for hybridization from first-strand cDNA

<400> SEQUENCE: 50
tttttttttt ttttttttv                                              19
```